United States Patent
Mahour et al.

(10) Patent No.: US 11,767,546 B2
(45) Date of Patent: Sep. 26, 2023

(54) ENZYMATIC METHOD FOR PREPARATION OF UDP-GLCNAC

(71) Applicant: Max-Planck-Gesellschaft zur Förderung der Wissenschaften e.V., Munich (DE)

(72) Inventors: Reza Mahour, Leipzig (DE); Thomas F. T. Rexer, Magdeburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 17/755,653

(22) PCT Filed: Sep. 30, 2020

(86) PCT No.: PCT/EP2020/077383
§ 371 (c)(1),
(2) Date: May 4, 2022

(87) PCT Pub. No.: WO2021/089249
PCT Pub. Date: May 14, 2021

(65) Prior Publication Data
US 2022/0380820 A1    Dec. 1, 2022

(30) Foreign Application Priority Data

Nov. 5, 2019  (EP) .................... 19207017

(51) Int. Cl.
| | |
|---|---|
| *C12P 19/30* | (2006.01) |
| *C12N 9/12* | (2006.01) |
| *C12N 9/10* | (2006.01) |
| *C12N 9/14* | (2006.01) |
| *C12N 11/08* | (2020.01) |
| *C12N 11/087* | (2020.01) |
| *C12P 19/18* | (2006.01) |
| *C12P 21/00* | (2006.01) |

(52) U.S. Cl.
CPC .......... *C12P 19/305* (2013.01); *C12N 9/1077* (2013.01); *C12N 9/1205* (2013.01); *C12N 9/1241* (2013.01); *C12N 11/087* (2020.01); *C12Y 207/04014* (2013.01); *C12Y 207/07009* (2013.01)

(58) Field of Classification Search
None
See application file for complete search history.

(56) References Cited

PUBLICATIONS

Liu et al. "Combined biosynthetic pathway for de novo production of UDP-galactose: catalysis with multiple enzymes immobilized on agarose beads." ChemBioChem (2002) 3:348-355.*

Kulinich et al., "Human milk oligosaccharides: The role in the fine-tuning of innate immune responses" Carbohydrate Research (2016) 432:62-70.
Zhao et al., "Enzymatic route to preparative-scale synthesis of UDP-GlcNAc/GalNAc, their analogues and GDP-fucose" Nat. Protoc. (2010) 5(4):636-646.
Chen et al., "One-pot three-enzyme synthesis of UDP-GlcNAc derivatives" Chem. Commun. (2011) 47:10815-10817.
Gaberc-Porekar et al., "Potential for Using Histidine Tags in Purification of Proteins at Large Scale" Chem. Eng. Technol. (2005) 28(11):1306-1314.
Kokhan et al., "Detection and quantification of transition metal leaching in metal affinity chromatography with hydroxynaphthol blue" Analytical Biochemistry (2019) 582:113347.
Zdarta et al., "A General Overview of Support Materials for Enzyme Immobilization: Characteristics, Properties, Practical Utility" Catalysts (2018) 8:92.
Datta et al., "Enzyme immobilization: an overview on techniques and support material" Biotech, (2013) 3:1-9.
Yi et al., "Covalent immobilization of w-transaminase from Vibrio fluvialis JS17 on chitosan beads" Process Biochemistry, (2007) 42:895-898.
Martin et al., "Characterization of free and immobilized (S)-aminotransferase for acetophenone production" Appl. Microbiol. Biotechnol. (2007) 76:843-851.
Koszelewski et al., "Immobilization of ω-transaminases by encapsulation in a sol-gel/celite matrix" J. Mol. Catalysis B: Enzymatic (2010) 63:39-44.
Truppo et al., "Development of an Improved Immobilized CAL-B for the Enzymatic Resolution of a Key Intermediate to Odanacatib" Org. Process Res. Dev. (2011) 15:1033-1035.
Mateo et al., "Epoxy Sepabeads: A Novel Epoxy Support for Stabilization of Industrial Enzymes via Very Intense Multipoint Covalent Attachment" Biotechnology Progress (2002) 18: 629-634.
Liese et al., "Evaluation of immobilized enzymes for industrial applications" Chemical Society Reviews (2013) 15:6236-6249.
Mahour, et al., "Establishment of a five-enzyme cell-free cascade for the synthesis of uridine diphosphate N-acetylglucosamine" Journal of Biotechnology (2018) 283:120-129.
Mateo, et al., "Advances in the design of new epoxy supports for enzyme immobilization-stabilization" Biochemical Society Transactions (2007) 35(6):1593-1601.

(Continued)

*Primary Examiner* — Suzanne M Noakes
*Assistant Examiner* — Jae W Lee
(74) *Attorney, Agent, or Firm* — Knobbe Martens Olson & Bear LLP

(57) ABSTRACT

The present invention relates to an enzyme-catalyzed process for producing UDP-N-acetyl-α-D-glucosamine (UDP-GlcNAc) from low-cost substrates uridine monophosphate and N-acetyl-D glucosamine in a single reaction mixture with immobilized or preferably co-immobilized enzymes. Uridine may be used as starting material instead of uridine monophosphate as well. Further, the process may be adapted to produce GlcNAcylated molecules and biomolecules including saccharides, particularly human milk oligosaccharides (HMO), proteins, peptides, glycoproteins, particularly antibodies, or glycopeptides, and bioconjugates, particularly carbohydrate conjugate vaccines and antibody-drug conjugates.

16 Claims, 26 Drawing Sheets
Specification includes a Sequence Listing.

(56) References Cited

PUBLICATIONS

Rexer, et al., "One pot synthesis of GDP-mannose by a multi-enzyme cascade for enzymatic assembly of lipid-linked oligosaccharides" Biotechnology and Bioengineering (2018) 115:192-205.
Shao, et al., "Biocatalytic synthesis of uridine 5'-diphosphate N-acetylglucosamine by multiple enzymes co-immobilized on agarose beads" Chemical Communications (2002) 22:2586-2587.
Zuffi, et al., "Immobilized Biocatalysts for the Production of Nucleosides and Nucleoside Analogues by Enzymatic Transglycosylation Reactions" Biocatalysis and Biotransformation (2004) 22(1):25-33.
International Search Report dated Jan. 20, 2021 for PCT Application No. PCT/EP2020/077383, filed Sep. 30, 2020.

* cited by examiner

First cycle

Second cycle

ECR8285

Eupergit® CM

EC-HFA

ENZYMATIC METHOD FOR PREPARATION OF UDP-GLCNAC

The present application is the national phase entry of PCT Application No. PCT/EP2020/077383, filed Sep. 30, 2020, which claims priority to EP Application No. 19207017.5, filed Nov. 5, 2019, both of which are incorporated by reference in their entireties.

REFERENCE TO SEQUENCE LISTING

The present application is filed with a Sequence Listing in Electronic format. The Sequence Listing is provided as a file entitled ABK001023APC.txt, created Apr. 20, 2022, which is approximately 29 kb in size. The information in the electronic format of the sequence listing is incorporated herein by reference in its entirety.

FIELD OF THE INVENTION

The present invention relates to an enzyme-catalyzed process for producing UDP-N-acetyl-α-D-glucosamine (UDP-GlcNAc) from low-cost substrates uridine monophosphate and N-acetyl-D-glucosamine in a single reaction mixture with immobilized or preferably co-immobilized enzymes. Further, said process may be adapted to produce GlcNAcylated molecules and biomolecules including saccharides, particularly human milk oligosaccharides (HMO), proteins, peptides, glycoproteins, particularly antibodies, or glycopeptides, and bioconjugates, particularly carbohydrate conjugate vaccines and antibody-drug conjugates.

BACKGROUND OF THE INVENTION

Uridine 5'-diphospho-N-acetyl-α-D-glucosamine (UDP-GlcNAc) is a key substrate for a large number of biotechnological applications and food technology. UDP-GlcNAc is needed for the production of carbohydrate vaccines and in the growing field of personalized medicine, i.e. preparation of glyconanomaterials for drug delivery. Moreover, in order to in vitro build the core structure of monoclonal antibodies and other recombinant proteins UDP-GlcNAc is extensively needed. In infant food (human milk), N-acetylglucosamine functionalized oligosaccharides comprise an important component of human milk oligosaccharides and, thus, there is a high demand to include GlcNAcylated sugars in synthetically produced dairy products for infants (Carbohydrate Research 432 (2016) 62-70). However, in spite of the high demand for UDP-GlcNAc (in the order of tons per year), the availability of UDP-GlcNAc is very limited, even for researchers. Up to now, the price of low endotoxin UDP-GlcNAc is above 1,500 Euros per gram. Due to the high price of UDP-GlcNAc not only basic and applied research activities are hampered but also industrial applications are hindered.

Bioprocess engineering strategies to synthesize UDP-GlcNAc can be classified into in vivo and in vitro processes: Chemical synthesis of UDP-GlcNAc in a five-step process has reached a yield of only 15%. Microorganisms are metabolically engineered in order to produce UDP-GlcNAc, either intracellulary or extracellularly, as part of their metabolism. However, low yields, high levels of unwanted by-products, the required time for cell line design and the complicated scale up are drawbacks. Taking into account regulatory aspects, specifically for infant food, application of genetically modified organisms (GMOs) can severely delay the approval process.

Conversely, enzymatic synthesis has shown higher yields. For, example, Zhao et al. (Zhao, G., Guan, W., Cai, L., Wang, P. G., 2010, Enzymatic route to preparative-scale synthesis of UDP-GlcNAc/GalNAc, their analogues and GDP-fucose, Nat. Protoc. 5, 636) used three enzymes N-acetylhexosamine kinase (NahK), UDP-N-acetylglucosamine diphosphorylase (GlmU) and inorganic diphosphatase (PmPpA) to produce UDP-GlcNac/UDP-GalNAc and their derivatives at preparative scale with a yield of 10%-65%. Chen et al. (Chen, Y., Thon, V., Li, Y., Yu, H., Ding, L., Lau, K., Qu, J., Hie, L., Chen, X., 2011, One-pot three-enzym synthesis of UDP-GlcNAc derivatives, Chem. Commun. 47, 10815-10817) managed to obtain a yield of 81% with the same enzymes. Shao et al. (Shao, J., Zhang, J., Nahálka, J. Wang, P. G., 2002, Biocatalytic synthesis of uridine 5'diphosphate N-acetylglucosamine by multiple enzymes co-immobilized on agarose beads, Chem. Commun. 2586-2587) used five immobilized enzymes to produce UDP-GlcNAc with a maximum yield of 78%. In their study, AGX1 (the mammalian type of GlmU) and GlmU were used together to increase the yield of GlcNAc-1-phosphate to UDP-GlcNAc. The regeneration of ATP from ADP was conducted by pyruvate kinase using phosphoenolpyruvate. Those enzymes were co-immobilized on Ni-NTA agarose beads for the synthesis of uridine 5'-diphosphate N-acetylglucosamine. The enzyme loaded Ni-NTA agarose beads were used repeatedly, but however they lost enzymatic activities during the reactions. Only a 50% yield of product could be achieved after five 20 h reaction cycles. Further enzymatic assays revealed that GlcNAc phosphate mutase was the least stable enzyme on beads, thereby being the main reason for the observed decrease of overall yield. Addition of purified Agm1 in the reaction could partially restore the whole activity and increase the yield of UDP-GlcNAc to 78%.

Ni-NTA agarose beads are impractical for larger scale synthesis. The enzymes are weakly bound on the agarose beads and rapidly washed off in reaction mixtures of high ionic strength which are necessary for an optimal UDP-GlcNAc production. Leaching of enzymes can severely hamper validation processes, specifically for food and pharma applications and makes it necessary to recharge the beads after each use. Further, nickel ions, which are toxic in large amounts, are released from the beads to the solution; thereby making their use in the synthesis of HMOS most likely impossible. Although for Ni-NTA leaching is stated to be low, usually up to 1 ppm, large amount of toxic Ni is released into the waste waters during column regeneration and recharging. (Gaberc-Porekar et al, Chem. Eng. Technol. 2005, 28 (11). 1306-1314). Elution with moderately strong chelating agents enhances Ni-NTA leaching (Kokhan et al, Analytical Biochemistry 2019, 582, 113347). Therefore, toxicity of Ni(II) leaching from the solid support is a serious concern for large-scale applications. Since Ni agarose beads are prone to leach toxic Ni(II) the beads are not mechanically stable In addition, these beads are not mechanically stable due to their softness, which prohibits its use in stirred tank reactors since the high shear rates cause agarose beads to degrade, or in large scale column packing due to compression.

Epoxy-activated supports are able to chemically react with all nucleophile groups placed on the surface of enzymes: lysine, histidine, cysteine, tyrosine etc and thus are used for enzyme immobilization (*Biochem Soc Trans* 2007, 35 (6), 1593-1601) For example enzymes immobilized on epoxy-functionalized resins were used for the production of nucleoside analogues by transglycosylation reactions, for example the transglycosylation reaction of sugar donor β-D-arabinofuranosyl-uracil (Ara-U) to β-D-arabinofuranosyl-2-6-diaminopurine (Ara-DAMP) (*Biocatalysis Biotrans* 2004, 22 (1), 25-33).

C. Xiao (PhD Thesis, Georgia State University, 12 Oct. 2018 "Enzymatic Synthesis of Common Sugar Nucleotide and Therapeutic Oligosaccharides") reports on binding of enzymes NahK and AGX1 (alanine glyoxylate aminotransferase) on solid supports macroporous styrene, octadecyl, epoxy methacrylate and epoxy butyl functionalized solid supports. While enzyme binding was successful, no activity of the immobilized enzymes was observed.

There is a long-felt need for a method of producing UDP-GlcNAc in a cost-effective manner starting from low cost and readily available substrates.

Thus, it is the objective of the present invention to provide a cost-effective and efficient method for the preparation of UDP-GlcNAc.

The objective of the present invention is solved by the teaching of the independent claims. Further advantageous features, aspects and details of the invention are evident from the dependent claims, the description, the figures, and the examples of the present application.

DESCRIPTION OF THE INVENTION

In biochemistry nucleotide sugars are well known as active forms of monosaccharides and in glycosylation reactions nucleotide sugars are known to act as glycosyl donors. Glycosyltransferases (GTFs) are enzymes that catalyze the transfer of saccharide moieties from activated nucleotide sugars to nucleophilic glycosyl acceptor molecules. Thus, in biochemistry the glycosylation reactions are catalyzed by glycosyltransferases.

In order to act as glycosyl donors it is essential that the respective monosaccharides are present in a highly energetic form, like for example in form of nucleotide sugars, particularly nucleotide diphospho sugars derived from uridine diphosphate, guanosine diphosphate or cytosine diphosphate and so on. Examples of well known nucleotide sugars are UDP-glucose, UDP-galactose, UDP-GlcNAc, UDP-GalNAc, UDP-xylose, UDP-glucuronic acid, GDP-mannose and GDP-fucose. It is well known that the conversion of simple monosaccharides into activated nucleotide sugars can be achieved by enzyme catalyzed reaction of a nucleoside triphosphate (NTP) and a glycosyl monophosphate, wherein the glycosyl monophosphate contains a phosphate group at the anomeric carbon.

In order to obtain a nucleoside diphosphate (NDP)-monosaccharide the used monosaccharide needs to be converted into a glycosyl monophosphate derivative. In general, said reaction can be accomplished by applying specific enzymes like phosphotransferases and additionally phosphomutases, if required, to obtain the desired monosaccharide-1-phosphate. Phosphotransferases are enzymes classified under EC number 2.7 that catalyze phosphorylation reactions. Phosphotransferases are further classified according to their acceptor molecule. For example, phosphotransferases under EC 2.7.1 are phosphotransferases with an alcohol group as acceptor. Phosphomutases are isomerases, i.e. enzymes that can catalyze an internal transfer of a phosphate group. Phosphomutases are required in case the phosphorylation of the substrate via phosphotransferase results in a monosaccharide-6-phosphate, like in case of D-mannose or D-glucose for example mannose-6-phosphate and glucose-6-phosphate, respectively. The respective phosphomutase then catalyzes the internal transfer of the phosphate group which results in the conversion of mannose-6-phosphate into mannose-1-phosphate or glucose-6-phosphate into glucose-1-phosphate, respectively.

Kinases are enzymes which form a part of the family of the phosphotransferases. Kinases are enzymes that catalyze the transfer of phosphate groups from high-energy, phosphate-donating molecules to specific substrates. This process is known as phosphorylation, where the substrate gains a phosphate group and the high-energy adenosine triphosphate (ATP) molecule donates a phosphate group.

This transesterification produces a phosphorylated substrate and ADP. Thus, in order to obtain a monosaccharide-1-phosphate, suitable kinases like an N-acetylhexosamine kinase may be applied to obtain N-acetyl-glucosamine-1-phosphate from N-acetylglucosamine.

With the use of nucleotidyltransferases a nucleoside triphosphate (NTP) and a monosaccharide-1-phosphate can be converted to the respective nucleoside diphosphate (NDP)-monosaccharide. Nucleotidyltransferases are transferase enzymes of phosphorus-containing groups and are classified under EC number 2.7.7. For the different naturally occurring nucleotides nucleotide-specific nucleotidyltransferases are known in the art, e.g. uridylyltransferases transfer uridylyl-groups, adenylyltransferases transfer adenylyl-groups, guanylyl-transferases transfer guanylyl-groups, cytidylyltransferases transfer cytidylyl-groups and thymidilyl-transferases transfer thymidilyl groups. Thus, nucleotidyltransferases are suitable to catalyze the reaction of monosaccharide-1-phosphates with nucleoside triphosphates, e.g. N-acetylglucosamine 1-phosphate with uridine triphosphate (UTP) to obtain UDP-GlcNAc. In case of UDP-GlcNAc a uridylyltransferase is suitable for catalyzing the reaction with uridine triphosphate (UTP). Uridine diphosphate (UDP)-monosaccharides which relate to naturally occurring UDP-monosaccharides are UDP-galactose, UDP-GalNAc and UDP-GlcNAc.

Notwithstanding the aforementioned drawbacks of the UDP-GlcNAc syntheses described in the literature, a further disadvantage of the general reaction scheme to NTP-sugars is based on the fact that the starting materials, in particular the respective nucleoside triphosphates are very expensive and thus the synthesis pathway results in a cost-intensive synthesis of NDP-monosaccharides and in particular of UDP-N-acetyl-α-D-glucosamine. As already described above, for UDP-N-acetyl-α-D-glucosamine there is a need in the art to provide a cost effective and efficient method for preparation of nucleoside diphosphate monosaccharides, particularly of UDP-N-acetyl-α-D-glucosamine from low cost and readily available starting materials.

With regard to UDP-monosaccharides, UDP-GlcNAc relates to naturally occurring activated UDP-sugars in mammals. Therefore UMP has been identified as suitable nucleotide and N-acetylglucosamine has been identified as suitable monosaccharide for the preparation of UDP-GlcNAc. It should be clear that with regard to an enzyme-catalyzed reaction at least suitable enzymes must be provided. Therefore the inventors have identified UMP and readily available N-acetylglucosamine as suitable starting materials for the production of UDP-GlcNAc in an enzymatic one-pot cascade reaction.

In order to provide a cost-effective and efficient method for the preparation of UDP-GlcNAc, UMP (uridine monophosphate) and N-acetylglucosamine were identified as suitable starting materials for the production of UDP-GlcNAc in an enzymatic cascade reaction as depicted in FIG. 1 which consists of (a) the formation of N-acetylglucosamine 1-phosphate (GlcNAc-1-P) from N-acetyl-glucosamine and adenosine triphosphate (ATP; catalytic amount), (b) the formation of uridine diphosphate (UDP) from uridine monophosphate (UMP) and a uridine monophosphate kinase and the formation of uridine triphosphate (UTP) from UDP and polyphosphate, and (c) the reaction of N-acetylglucosamine 1-phosphate with uridine triphosphate (UTP) to UDP-GlcNAc. It was envisioned that UDP-GlcNAc can be produced directly from N-acetylglucosamine and uridine monophosphate in the presence of an N-acetylhexosamine kinase, a uridine monophosphate kinase, a polyphosphate kinase, and a glucose-1-phosphate uridylyltransferase, each enzyme being immobilized on a solid support.

Surprisingly, the inventors have found that the enzymes used in the preparation of UDP-GlcNAc can be covalently or adsorptively immobilized on a mechanically robust solid support such that they retain their activity, substrate specificity, stereoselectivity and/or other properties. Particularly, the robust solid support with covalently or adsorptively immobilized enzymes allows in general UDP-GlcNAc synthesis in more than 20 cycles. Covalent or adsorptive binding of the enzymes to the solid support minimizes washing off the enzymes, while maintaining their activity. A mechanically stable support inhibits degradation of the solid support and also does not leach toxic substances, such as Ni, during multiple reaction cycles.

The synthesis of UDP-GlcNAc in such a large number of cycles is a significant improvement of the process and has not been reported before in the prior art. Ni agarose beads or Ni NTA agarose resins of the prior art cannot be used in more than two cycles without losing significant amount of enzyme activity (see FIG. 33 and Example 4 for comparison). Enzymes are bound to Ni agarose beads by affinity binding (via histidine tag), which may be washed off due to Ni leaching. In addition, Ni NTA agarose resins are not mechanically stable due to their softness, which causes the agarose beads to degrade during reaction in stirred tank reactors.

Furthermore is has been found that the activity of all enzymes can even be increased, in particular when the enzymes used in the preparation of UDP-GlcNAc are covalently or adsorptively co-immobilized on a mechanically robust solid support. Surprisingly, it has been further found that the solid support loaded with said enzymes can be used for the production of UDP-GlcNAc multiple times in comparison to the prior art or continuously over a prolonged time. Surprisingly, it has been further found that the enzymes used in the preparation of UDP-GlcNAc can be co-immobilized from crude cell lysate or crude cell homogenate. Surprisingly, it has also been found that uridine can be used as starting material instead of uridine monophosphate in the preparation of UDP-GlcNAc.

Thus, the present invention is directed to a method for producing uridine 5'-diphospho-N-acetyl-α-D-glucosamine comprising the following steps:

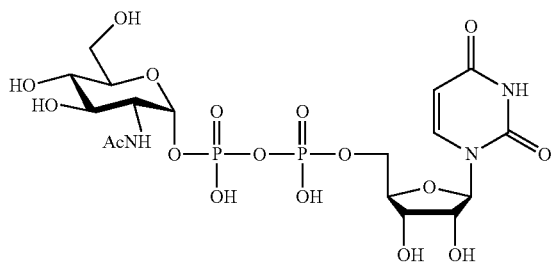

A) providing a solution comprising
(i) uridine monophosphate and N-acetyl-D-glucosamine represented by the following formulae

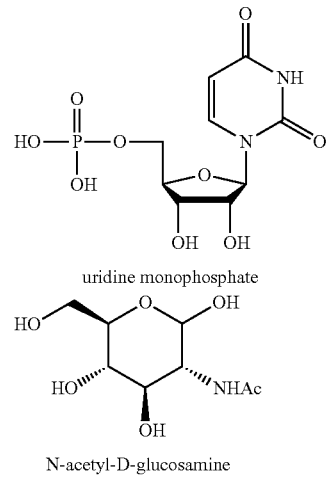

uridine monophosphate

N-acetyl-D-glucosamine (ii) polyphosphate, and adenosine triphosphate; and
providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

The production step B) of uridine 5'-diphospho-N-acetyl-α-D-glucosamine according to the invention comprises
(a) forming N-acetyl-D-glucosamine 1-phosphate (GlcNAc-1-P) from N-acetyl-D-glucosamine and adenosine triphosphate being catalyzed by an N-acetylhexosamine kinase,
(b) forming uridine triphosphate (UTP) from uridine monophosphate (UMP), adenosine triphosphate and polyphosphate being catalyzed by a polyphosphate kinase and a uridine monophosphate kinase; and
(c) reacting N-acetyl-D-glucosamine 1-phosphate with uridine triphosphate to UDP-N-acetyl-α-D-glucosamine in the presence of a glucose-1-phosphate uridylyltransferase.

Apparently, the steps (a) and (b) may be carried out simultaneously or successively. Also, their order may be reverted to (b)→(a)→(c).

Thus, the present invention is directed to a method for producing uridine 5'-diphospho-N-acetyl-α-D-glucosamine comprising the following steps:
A) providing a solution comprising
(i) uridine monophosphate and N-acetyl-D-glucosamine;
(ii) polyphosphate, and adenosine triphosphate; and
providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate by (a) forming N-acetyl-D-glucosamine 1-phosphate (GlcNAc-1-P) from N-acetyl-D-glucosamine and adenosine triphosphate being catalyzed by an N-acetylhexosamine kinase,
(b) forming uridine triphosphate (UTP) from uridine monophosphate (UMP), adenosine triphosphate and polyphosphate being catalyzed by a uridine monophosphate kinase and a polyphosphate kinase; and
(c) reacting N-acetyl-D-glucosamine 1-phosphate with uridine triphosphate to UDP-N-acetyl-D-glucosamine in the presence of a glucose-1-phosphate uridylyltransferase,
wherein the set of enzymes is covalently or adsorptively immobilized on a reusable, mechanically stable solid support.

More specifically, the production step B) of uridine 5'-diphospho-N-acetyl-α-D-glucosamine according to the invention comprises
(a) forming N-acetyl-D-glucosamine 1-phosphate (GlcNAc-1-P) from N-acetyl-D-glucosamine and adenosine triphosphate being catalyzed by an N-acetylhexosamine kinase,
(b1) forming uridine diphosphate (UDP) from uridine monophosphate and adenosine triphosphate being catalyzed by a uridine monophosphate kinase;
(b2) forming uridine triphosphate (UTP) from uridine diphosphate and polyphosphate being catalyzed by a polyphosphate kinase; and
(c) reacting N-acetyl-D-glucosamine 1-phosphate with uridine triphosphate to UDP-N-acetyl-D-glucosamine in the presence of a glucose-1-phosphate uridylyltransferase.

Apparently, the step (a) may be carried out before, simultaneously to or after step (b1) or (b2). Thus, the step order may also be reverted to (b1)→(b2)→(a)→(c).

Thus, the present invention is directed to a method for producing uridine 5'-diphospho-N-acetyl-α-D-glucosamine comprising the following steps:
A) providing a solution comprising
  (i) uridine monophosphate and N-acetylglucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate by
(a) forming N-acetylglucosamine 1-phosphate (GlcNAc-1-P) from N-acetyl-D-glucosamine and adenosine triphosphate being catalyzed by an N-acetylhexosamine kinase;
(b1) forming uridine diphosphate (UDP) from uridine monophosphate and adenosine triphosphate being catalyzed by a uridine monophosphate kinase;
(b2) forming uridine triphosphate (UTP) from uridine diphosphate and polyphosphate being catalyzed by a polyphosphate kinase; and
(c) reacting N-acetyl-D-glucosamine 1-phosphate with uridine triphosphate to UDP-N-acetyl-D-glucosamine in the presence of a glucose-1-phosphate uridylyltransferase,
wherein the set of enzymes is covalently or adsorptively immobilized on a reusable, mechanically stable solid support.

The inventive method for producing UDP-N-acetyl-α-D-glucosamine has the following significant advantages over the methods described in the prior art:
 significant cost reduction with respect to starting materials, i.e. no expensive UDP or UTP is required,
 the method can be performed in a continuous manner, thereby potentially allowing providing UDP-N-acetyl-α-D-glucosamine on a ton scale per year,
 cell-free process, thereby avoiding adverse GMO aspects (regulation, labelling),
 direct use of cell-free extracts, no costs for biocatalyst purification,
 solid support loaded with enzymes can be reused multiple times
 nearly quantitative yield with respect to N-acetyl-D-glucosamine,
 high scalability renders the inventive method useful for industrial applications.

In one embodiment the method for producing uridine 5'-diphospho-N-acetyl-α-D-glucosamine comprises the following steps:
A) providing a solution comprising
  (i) uridine monophosphate and N-acetyl-D-glucosamine
  (ii) polyphosphate, and adenosine triphosphate; and
  providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein at least one enzyme of the set of enzymes is immobilized on a reusable, mechanically stable solid support.

Covalent immobilization or covalent binding as used herein refers to the formation of a covalent chemical bond between the enzyme and a functional reactive group on the reusable, mechanically stable solid support such that the enzyme attaches to the solid support and retains large part of or increases its activity, substrate specificity, stereoselectivity and/or other properties. Covalent binding is characterized by forming a stable complex between the enzyme and the solid support, which hinders that the enzymes get washed off easily. Examples of covalent binding are given further below. Covalent enzyme immobilization can be achieved with any methods of enzyme immobilization known in the art as well as the methods described herein.

The enzymes can also be bound by adsorption to the reusable, mechanically stable solid support such that the enzyme attaches to the solid support and retains large part of or increases its activity, substrate specificity, stereoselectivity and/or other properties. Adsorption binding makes use of the physical interactions generated between the solid support and the enzyme that include van der Waals forces, ionic interactions and hydrogen bonding. Adsorption binding does not change the native structure of the enzyme, thereby preventing the active sites of the enzymes from disturbing and allowing the enzyme to retain its activity. Examples of adsorption binding are given further below. Adsorptive enzyme immobilization can be achieved with any methods of enzyme immobilization known in the art as well as the methods described herein.

However, in the inventive methods described herein, the enzymes are not immobilized by affinity binding to the reusable, mechanically stable solid support. Particularly, in the inventive methods described herein, the enzymes are not immobilized on Ni-NTA solid supports, such as Ni-NTA agarose beads.

Thus, in one embodiment the method for producing uridine 5'-diphospho-N-acetyl-α-D-glucosamine comprises the following steps:

A) providing a solution comprising
   (i) uridine monophosphate and N-acetyl-D-glucosamine
   (ii) polyphosphate, and adenosine triphosphate; and
   providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is not immobilized by affinity binding on a reusable, mechanically stable solid support.

Thus, in one embodiment the method for producing uridine 5'-diphospho-N-acetyl-α-D-glucosamine comprises the following steps:
A) providing a solution comprising
   (i) uridine monophosphate and N-acetyl-D-glucosamine
   (ii) polyphosphate, and adenosine triphosphate; and
   providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support, wherein the reusable, mechanically stable solid support is not a Ni agarose bead or a Ni NTA agarose resin.

Preferably, the set of enzymes is covalently or adsorptively co-immobilized on a reusable, mechanically stable solid support, thereby forming a robust solid enzyme preparation.

Thus, in the context of the present invention a reusable, mechanically stable solid support is a support which allows its multiple use within the inventive method for producing uridine 5'-diphospho-N-acetyl-α-D-glucosamine, as well as other inventive methods described herein, such that all enzymes covalently or adsorptively co-immobilized on the solid support retain large part of or increase their activity, substrate specificity, stereoselectivity and/or other properties, such that the enzymes are not washed off the solid support, and without significant degradation or abrasion of the solid support due to mechanical stress.

In one embodiment the method for producing uridine 5'-diphospho-N-acetyl-α-D-glucosamine comprises the following steps:
A) providing a solution comprising
   (i) uridine monophosphate and N-acetyl-D-glucosamine
   (ii) polyphosphate, and adenosine triphosphate; and
   providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently immobilized on a reusable, mechanically stable solid support.

In one embodiment the method for producing uridine 5'-diphospho-N-acetyl-α-D-glucosamine comprises the following steps:
A) providing a solution comprising
   (i) uridine monophosphate and N-acetyl-D-glucosamine
   (ii) polyphosphate, and adenosine triphosphate; and
   providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is adsorptively immobilized on a reusable, mechanically stable solid support.

In another embodiment the method for producing uridine 5'-diphospho-N-acetyl-α-D-glucosamine comprises the following steps:
A) providing a solution comprising
   (i) uridine monophosphate and N-acetyl-D-glucosamine
   (ii) polyphosphate, and adenosine triphosphate; and
   providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently co-immobilized on a reusable, mechanically stable solid support.

Further, the enzymes can be covalently or adsorptively co-immobilized directly from crude cell lysate or crude cell homogenate on the reusable, mechanically stable solid support and the solid support can be used in a large number of cycles (e.g. 20 batch cycles and more), or when the inventive methods described herein are run continuously, the reusable, mechanically stable solid support can be used over a prolonged time. The term "robust solid support" is used synonymously herein for a reusable, mechanically stable solid support that i) allows the co-immobilization of the set of enzymes from crude cell lysate or crude cell homogenate, ii) retains large parts of or increases the activity of all enzymes co-immobilized iii) allows the synthesis of the target product in a large number of cycles (e.g. 20 batch cycles and more), or when the inventive methods described herein are run continuously, the solid support can be used over a prolonged time.

Preferably, the reusable, mechanically stable solid supports can be used in at least 3 cycles, more preferably in at least 4 cycles, more preferably in at least 5 cycles, more preferably in at least 6 cycles, more preferably in at least 7 cycles, more preferably in at least 8 cycles, more preferably in at least 9 cycles, more preferably in at least 10 cycles, more preferably in at least 12 cycles, more preferably in at least 14 cycles, more preferably in at least 16 cycles, more preferably in at least 18 cycles, more preferably in at least 20 cycles, more preferably in at least 25 cycles, more preferably in at least 25 cycles, more preferably in at least 30 cycles, and most preferably in at least 50 cycles of the inventive method described herein.

A further aspect of the present invention is directed to the GlcNAcylation of molecules and biomolecules including saccharides, proteins, peptides, glycoproteins or glycopeptides, particularly human milk oligosaccharides (HMO) and (monoclonal) antibodies, comprising the steps of:
A) providing a solution comprising
   (i) uridine monophosphate and N-acetyl-D-glucosamine;
   (ii) polyphosphate, and adenosine triphosphate; and providing a set of enzymes comprising a glucose-1-phosphate uridylyl-transferase, an N-acetylhexosamine kinase, a polyphosphate kinase, and a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate; and D) producing a GlcNAcylated saccharide, GlcNAcylated glycopeptide, GlcNAcylated glycoprotein, GlcNAcylated protein, GlcNAcylated peptide or GlcNAcylated small molecule from uridine 5'-diphospho-N-acetyl-α-D-glucosamine and a saccharide, glycopeptide, glycoprotein, protein, peptide or small molecule by forming an O-glycosidic bond between uridine 5'-diphospho-N-acetyl-α-D-glucosamine and an available hydroxyl group of the saccharide, glycopeptide, glycoprotein, protein, peptide or small molecule in the presence of an N-acetylglucosaminyltransferase, wherein the set of enzymes is covalently or adsorptively immobilized on a reusable, mechanically stable solid support.

N-acetylglucosaminyltransferases are part of EC 2.4.1. subgroup. Examples include, but are not limited to: lipopolysaccharide N-acetylglucosaminyltransferase (LgtA) (EC 2.4.1.56); N-acetyllactosaminide beta-1,6-N-acetylglucosaminyl-transferase (GCNT2) (EC. 2.4.1.150); protein O-GlcNAc transferase (OGT) (EC 2.4.1.255); and alpha-1, 3-mannosyl-glycoprotein 2-beta-N-acetyl-glucosaminyl-transferase (EC 2.4.1.101)

In one embodiment of the inventive method for GlcNAcylation, UTP is regenerated from the side product UDP. Therefore, only catalytic amounts of UMP are required. Thus, the inventive method for GlcNAcylation comprises the steps of:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, and a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate; and D) producing a GlcNAcylated saccharide, GlcNAcylated glycopeptide, GlcNAcylated glycoprotein, GlcNAcylated protein, GlcNAcylated peptide or GlcNAcylated small molecule from uridine 5'-diphospho-N-acetyl-α-D-glucosamine and a saccharide, glycopeptide, glycoprotein, protein, peptide or small molecule by forming an O-glycosidic bond between uridine 5'-diphospho-N-acetyl-α-D-glucosamine and an available hydroxyl group of the saccharide, glycopeptide, glycoprotein, protein, peptide or small molecule in the presence of an N-acetylglucosaminyltransferase.

E) recycling of uridine diphosphate formed in step D) to obtain uridine triphosphate, wherein the set of enzymes is covalently or adsorptively immobilized on a reusable, mechanically stable solid support.

Preferably, the set of enzymes is co-immobilized on a reusable, mechanically stable solid support. Said reusable solid support can be for example functionalized with epoxy groups.

Therefore, a further aspect of the present invention is directed to a set of enzymes comprising a glucose-1-phosphate uridylyltransferase, an N-acetylhexosamine kinase, a polyphosphate kinase, and a uridine monophosphate kinase; wherein the set of enzymes is covalently or adsorptively co-immobilized on a reusable, mechanically stable solid support, preferably the set of enzymes is co-immobilized on a polymer functionalized with epoxy groups.

Preferably, a glycosyltransferase or N-acetylglucosaminyltransferase is covalently or adsorptively co-immobilized together with the set of enzymes on the reusable, mechanically stable solid support.

DETAILED DESCRIPTION OF THE INVENTION

Definitions

As used herein, the term "polyphosphate" refers to any salts containing several P—O—P bonds generated by corner sharing of six or more phosphate ($PO_4$) tetrahedral, leading to the formation of long chains. The term "$PolyP_n$" is synonymously used, wherein n represents average chain length of the number of phosphate residues, e.g. $PolyP_{25}$ refers to a polyphosphate having about 25 phosphate residues and $PolyP_{14}$ refers to a polyphosphate having about 14 phosphate residues.

As used herein, the term "uridine monophosphate kinase" or refers to a polypeptide having uridine monophosphate kinase activity, i.e. a uridine monophosphate kinase catalyzes the reaction of uridine monophosphate to uridine 5'-diphosphate in the presence of adenosine triphosphate. The uridine monophosphate kinase belongs to the EC class 2.7.4.14. The uridine monophosphate kinase catalyzes the following reaction:

$$UMP + ATP \rightleftharpoons UDP + ADP$$

As used herein, the term "uridine kinase" or refers to a polypeptide having uridine kinase activity, i.e. a uridine kinase catalyzes the reaction of uridine to uridine 5-monophosphate in the presence of adenosine triphosphate. The uridine kinase belongs to the EC class 2.7.1.48.

As used herein, the term "polyphosphate kinase" refers to a polypeptide having polyphosphate kinase activity, i.e. a polyphosphate kinase catalyzes the following reactions:

$$NMP + polyphosphate\ (n+1) \rightleftharpoons NDP + polyphosphate(n)$$

$$NDP + polyphosphate\ (n+1) \rightleftharpoons NTP + polyphosphate(n)$$

with N being a nucleotide such as guanosine, adenosine, uridine etc. and NMP being nucleoside monophosphate, NDP being nucleoside diphosphate and NTP being nucleoside triphosphate.

In case of uridine the polyphosphate kinase catalyzes the following reaction:

$$ADP + polyphosphate\ (n+1) \rightleftharpoons ATP + polyphosphate(n)$$

$$AMP + polyphosphate\ (n+1) \rightleftharpoons ADP + polyphosphate(n)$$

$$UDP + polyphosphate\ (n+1) \rightleftharpoons UTP + polyphosphate(n)$$

The polyphosphate kinase belongs to the EC class 2.7.4.1. Representatives of the polyphosphate kinase enzyme used in the inventive methods described herein include but are not limited to polyphosphate kinase 1 (PPK1), polyphosphate kinase 2 (PPK2), 2-domain polyphosphate kinase 2 (2D-PPK2) and 1-domain polyphosphate kinase 2 (1 D-PPK2) and polyphosphate kinase 3 (PPK3).

As used herein, the term "uridylyltransferase" refers to a polypeptide having a uridylyltransferase activity, e.g. a UTP:α-D-glucose-1-phosphate uridylyltransferase that catalyzes the following reaction:

Glc-1-P+UTP⇌UDP-Glc+PPi

Nucleotidyltransferases belong to the EC class 2.7.7. Examples of known uridylyltransferases include, but are not limited to hexosel-phosphate uridylyltransferase, which belongs to EC class 2.7.7.10, xylose-1-phosphate uridylyltransferase (GalT), which belongs to EC class 2.7.7.11, UDP-glucose hexose-1-phosphate uridylyltransferase (GalT), which belongs to EC class 2.7.7.12, and glucose 1-phosphate uridylyltransferase (GalU), which belongs to EC class 2.7.7.9. The glucose 1-phosphate uridylyltransferase also catalyzes the transfer of UTP to N-acetylhexosamine 1-phosphate:

GlcNAc-1-P+UTP⇌UDP-GlcNAc+PPi

As used herein, the term "pyrophosphatase" refers to a polypeptide having pyrophosphatase activity, i.e. a polypeptide that catalyzes the following reaction:

PPi+H₂O⇌2Pi wherein PPi refers to pyrophosphate and Pi to phosphate.

The pyrophosphatase belongs to EC classes 3.6.1.1. In this context, the term "diphosphatase" refers to a pyrophosphatase polypeptide which catalyzes the hydrolysis of diphosphate to phosphate.

As used herein, the term "N-acetylhexosamine kinase" refers to a polypeptide having kinase activity, i.e. a kinase that catalyzes the following phosphorylation to N-acetylhexosamine 1-phosphate:

GlcNAc+ATP⇌GlcNAc-1-P+ADP

The N-acetylhexosamine kinase belongs to the EC class 2.7.1.162.

As used herein, the term "uracil phosphoribosyltransferase" refers to a polypeptide having phosphoribosyltransferase activity, i.e. a transferase that catalyzes the following reaction:

uracil+PRPP⇌UMP+PPi wherein PRPP refers a phosphorylated pentose, preferably a phosphorylated ribose and most preferably to 5-phospho-α-D-ribose 1-diphosphate. Exemplarily, the transferase is, but not limited to, a uracil phosphoribosyltransferase belonging to EC class 2.4.2.9 or an AMP phosphorylase belonging to EC class 2.4.2.57, of which such a transferase activity is also known.

As used herein, the term "UMP synthase" refers to a polypeptide having uridine monophosphate synthetase activity, i.e. a synthase that catalyzes the following reaction:

OMP⇌UMP+CO₂ wherein OMP refers to orotidine 5-phosphate. The term UMP synthase is synonymously used for orotidine 5-phosphate decarboxylase and this enzyme belongs to EC class 4.1.1.23.

As used herein, the term "orotate phosphoribosyltransferase" refers to a polypeptide having orotate phosphoribosyltransferase activity, i.e. a transferase that catalyzes the following reaction:

orotic acid+PRPP⇌OMP+PPi

The transferase belongs to EC class 2.4.2.10.

As used herein, the term "glycosyltransferase" refers to polypeptide having glycosyltransferase activity, i.e. a polypeptide that catalyzes the transfer of a monosaccharide from NDP-monosaccharide to acceptor saccharides, such as glucose or N-acetylglucosamine.

As used herein, the term "N-acetylglucosaminyltransferase" refers to polypeptide having N-acetylglucosaminyltransferase activity, i.e. a polypeptide that catalyzes the transfer of an N-acetylglucosamine from NDP-GlcNAc to acceptor saccharides or proteins. N-acetylglucosaminyltransferases in general belong to the EC class 2.4.1. Examples include, but are not limited to lipopolysaccharide N-acetylglucosaminyltransferase (LgtA) (EC. 2.4.1.56); N-acetyllactosaminide beta-1,6-N-acetylglucosaminyltransferase (GCNT2) (EC. 2.4.1.150); protein O-GlcNAc transferase (OGT) (EC 2.4.1.255); alpha-1,3-mannosyl-glycoprotein 2-beta-N-acetylglucosaminyltransferase (EC 2.4.1.101); or ß-1,3-N-acetyl-glucosamine transferase (ß1, 3GlcNAcT) (EC 2.4.1.149).

As used herein, "saccharide" refers to but not restricted to monosaccharide, disaccharide, trisaccharide, tetrasaccharide, pentasaccharide, hexasaccharide, heptasaccharide, octasaccharide . . . , oligosaccharide, glycan and polysaccharide.

The saccharide comprises preferably monosaccharide units selected from: D-Arabinose, D-Lyxose, D-Ribose, D-Xylose, L-Arabinose, L-Lyxose, L-Ribose, L-Xylose, D-Ribulose, D-Xylulose, L-Ribulose, L-Xylulose, D-Deoxyribose, L-Deoxyribose, D-Erythrose, D-Threose, L-glycero-D-manno-Heptose, D-glycero-D-manno-Heptose, D-Allose, D-Altrose, D-Glucose, D-Mannose, D-Gulose, D-Idose, D-Galactose, D-Talose, D-psicose, D-fructose, D-sorbose, D-tagatose, 6-Deoxy-L-altrose, 6-Deoxy-D-talose, D-Fucose, L-Fucose, D-Rhamnose, L-Rhamnose, D-Quinovose, Olivose, Tyvelose, Ascarylose, Abequose, Paratose, Digitoxose, Colitose, D-Glucosamine, D-Galactosamine, D-Mannosamine, D-Allosamine, I-Altrosamine, D-Gulosamine, L-Idosamine, D-Talosamine, N-Acetyl-d-glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, D-Glucuronic acid, D-Galacturonic acid, D-Mannuronic acid, D-Alluronic acid, L-Altruronic acid, D-Guluronic acid, L-Guluronic acid, L-Iduronic acid, D-Taluronic acid, Neuraminic acid, N-Acetylneuraminic acid, N-Glycolylneuraminic acid, Apiose, Bacillosamine, Thevetose, Acofriose, Cymarose, Muramic acid, N-Acetylmuramic acid, N-Glycolylmuramic acid, 3-Deoxy-lyxo-heptulosaric acid, Ketodeoxyoctonic acid, and Ketodeoxynononic acid. Preferably the monosaccharide units belong to the following group of α- and β-D/L-carbohydrates comprising or consisting of:

α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

The saccharides are further optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

As used herein, the term "glycopeptide" refers to a peptide that contains carbohydrate moieties covalently attached to the side chains of the amino acid residues that constitute the peptide. The carbohydrate moieties form side chains and are either O-glycosidic connected to the hydroxy group of a serine or threonine residue or N-glycosidic connected to the amido nitrogen of an asparagine residue.

As used herein, the term "glycoprotein" refers to a polypeptide that contains carbohydrate moieties covalently attached to the side chains of the amino acid residues that constitute the polypeptide. The carbohydrate moieties form side chains and are either O-glycosidic connected to the hydroxy group of a serine or threonine residue or N-glycosidic connected to the amido nitrogen of an asparagine residue.

As used herein, the term "protein" refers to a polypeptide that contains or lacks of carbohydrate moieties covalently attached to the side chains of the amino acid residues that constitute the polypeptide including aglycosylated proteins and glycosylated proteins.

As used herein, the term "peptide" refers to a peptide that contains or lacks of carbohydrate moieties covalently attached to the side chains of the amino acid residues that constitute the peptide, including aglycosylated peptides and glycosylated peptides.

As used herein, the term "bioconjugate" refers to a molecular construct consisting of at least two molecules which are covalently bound to each other and wherein at least one of which is a biomolecule, i.e. a molecule present in organisms that are essential to one or more typically biological processes. Exemplarily bioconjugates are carbohydrate conjugate vaccines consisting of a carbohydrate antigen covalently coupled to a carrier protein, and antibody drug conjugates.

As used herein, the term "carbohydrate conjugate vaccine" refers to a conjugate containing a carbohydrate antigen covalently bound to an immunogenic carrier. The carbohydrate antigen can be, but is not limited to, a bacterial capsular saccharide, a saccharide of a viral glycoprotein, a saccharide antigen of sporozoa or parasites, a saccharide antigen of pathogenic fungi, or a saccharide antigen which is specific to cancer cells. The immunogenic carrier can be, but is not limited to, a carrier protein selected from toxoids, including tetanus toxoid (TT), diphtheria toxoid (DT), cross-reaction material 197 ($CRM_{197}$), protein D of non-typeable *H. influenzae*, outer membrane protein complexes of *Neisseria meningitidis* capsular group B (OMPCs), exotoxin A of *P. aeruginosa* (EPA), *C. difficile* toxin A (CDTA), pneumococcal proteins, such as pneumococcal surface protein A (PspA), pneumococcal histidine triad D (PhtD), detoxified pneumolysin (dPly), and spr96/2021, *S. aureus* a toxin and Shiga toxin 1 b.

The term "solid support" as used herein refers to an insoluble, functionalized, material to which enzymes or other reagents may be attached or immobilized, directly or via a linker bearing an anchoring group, allowing enzymes to be readily separated (by washing, filtration, centrifugation, etc.) from excess reagents, soluble reaction products, by-products, or solvents. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. A solid support can also consist of magnetic particles. For an overview of suitable support materials for enzyme immobilization see Zdarta et al. *Catalysts* 2018, 8, 92, and Datta et al. Biotech 2013 3:1-9.

The configuration of a solid support can be in the form of beads, monoliths, spheres, particles, a particle bed, a fiber mat, granules, a gel, a membrane, a hollow-fiber membrane, a mixed-matrix membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

The concentration of uridine monophosphate and N-acetyl-D-glucosamine in the solution provided in step A) is preferably in the range of 0.01 mM to 100,000 mM. More preferably, the concentration of uridine monophosphate and N-acetylglucosamine is preferably in the range of 0.05 mM to 50,000 mM. More preferably, the concentration of uridine monophosphate and N-acetylglucosamine is preferably in the range of 0.1 mM to 30,000 mM. More preferably, the concentration of uridine monophosphate and N-acetylglucosamine is preferably in the range of 0.2 mM to 15,000 mM.

Thus, the present invention is directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate;
wherein the concentration of uridine monophosphate and N-acetyl-D-glucosamine in the solution provided in step A) is in the range of 0.2 mM to 15,000 mM, and wherein the set of enzymes is covalently or adsorptively immobilized on a reusable, mechanically stable solid support. Preferably, the set of enzymes is covalently co-immobilized on a reusable, mechanically stable solid support, thereby increasing or retaining a large fraction of the activity of each enzyme.

Preferably, the concentration of the enzymes in the set of enzymes is between 0.000001 mg/mL and 100 mg/mL based on the total volume of the solution provided in step A).

As a side product in the reaction of N-acetylglucosamine-1-phosphate with uridine triphosphate to UDP-N-acetyl-α-D-glucosamine, pyrophosphate (PPi) is formed. Although pyrophosphate is unstable in aqueous solution, it only slowly hydrolyzes into inorganic phosphate (Pi). A high concentration of pyrophosphate may also inhibit the activity of the glucose-1-phosphate uridylyltransferase enzyme involved in the UDP-N-acetyl-α-D-glucosamine formation. In addition, pyrophosphate is known for its ability to inhibit uridylyl- and guanylyltransferases. The enzyme pyrophosphatase is able to catalyze the hydrolysis of pyrophosphate to phosphate, thereby effectively rendering the UDP-formation irreversible. Thus, in a preferred embodiment of the present invention the set of enzymes further comprises a pyrophosphatase.

Therefore, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, a uridine monophosphate kinase and a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support. Preferably, the set of enzymes is covalently co-immobilized on a reusable, mechanically stable solid support thereby increasing or retaining a large fraction of the activity of each enzyme.

Thus, the present invention is directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, a uridine monophosphate kinase and a pyrophosphatase;
B) producing uridine 5'-diphospho-N-acetylglucosamine from uridine monophosphate and N-acetylglucosamine in the presence of the set of enzymes, polyphosphate, and adenosine triphosphate by
  (a) forming N-acetylglucosamine 1-phosphate (GlcNAc-1-P) from N-acetylglucosamine and adenosine triphosphate being catalyzed by an N-acetylhexosamine kinase,
  (b) forming uridine triphosphate (UTP) from uridine monophosphate (UMP), adenosine triphosphate and polyphosphate being catalyzed by a uridine monophosphate kinase and a polyphosphate kinase; and
  (c') reacting N-acetylglucosamine 1-phosphate with uridine triphosphate to UDP-N-acetyl-α-D-glucosamine in the presence of a glucose-1-phosphate uridylyltransferase
  (c") converting pyrophosphate to phosphate in the presence of a pyrophosphatase, wherein the set of enzymes is covalently or adsorptively immobilized on a reusable, mechanically stable solid support Preferably, the set of enzymes is covalently co-immobilized on a reusable, mechanically stable solid support thereby increasing or retaining a large fraction of the activity of each enzyme.

Reworded, the inventive method for producing uridine 5'-diphospho-N-acetylglucosamine comprising the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, a uridine monophosphate kinase and a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate by
  (a) forming N-acetylglucosamine-1-phosphate from N-acetylglucosamine and adenosine triphosphate being catalyzed by an N-acetylhexosamine kinase,
  (b1) forming uridine diphosphate from uridine monophosphate and adenosine triphosphate being catalyzed by a uridine monophosphate kinase;
  (b2) forming uridine triphosphate from uridine diphosphate and polyphosphate being catalyzed by a polyphosphate kinase,
  (c') reacting N-acetylglucosamine-1-phosphate with uridine triphosphate to UDP-N-acetylglucosamine and pyrophosphate in the presence of glucose-1-phosphate uridylyltransferase; and
  (c") converting pyrophosphate to phosphate in the presence of a pyrophosphatase,
wherein the set of enzymes is covalently or adsorptively immobilized on a reusable, mechanically stable solid support. Preferably, the set of enzymes is covalently co-immobilized on a reusable, mechanically stable solid support thereby increasing or retaining a large fraction of the activity of each enzyme.

Preferably, the pyrophosphatase used in the inventive methods described herein is an inorganic pyrophosphatase. Preferably, the pyrophosphatase is an inorganic pyrophosphatase from *Pasteurella multocida* (PmPpA).

Polyphosphate is able to form stable, water-soluble complexes with metal ions (e.g. $Ca^{2+}$, $Mg^{2+}$, $Fe^{2+}$, $Fe^{2+/3+}$) which were initially dissolved in aqueous media. This effect is called sequestration and prevents the bound metal ions from participating in reactions, particularly enzymatic reactions. Therefore, the sequestered metal ions, particularly $Mg^{2+}$ and $Mn^{2+}$, cannot act as co-factor for the enzymes involved in the inventive methods described herein. As the ability of a particular polyphosphate to sequester a particular metal ion decreases with increasing chain length of the polyphosphate, long-chain polyphosphates are preferred in the present invention. More preferred are polyphosphates having at least 14 phosphate residues. Most preferred are polyphosphates having at least 25 phosphate residues.

Thus, the present invention is directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetylglucosamine in the presence of the set of enzymes, polyphosphate, and adenosine triphosphate,
wherein the polyphosphate is a long-chain polyphosphate having at least 25 phosphate residues, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the enzymes are present in a single reaction mixture with the other substrates. Thus, the uridine 5'-diphospho-N-acetyl-α-D-glucosamine is produced in a single reaction mixture according to a further aspect of the inventive method.

Thus, the method for producing uridine 5'-diphospho-N-acetyl-α-D-glucosamine comprising the following steps:
A) providing a mixture comprising
 (i) uridine monophosphate and N-acetyl-D-glucosamine;
 (ii) polyphosphate, and adenosine triphosphate; and
 providing a set of enzymes comprising a glucose-1-phosphate uridylyl-transferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetylglucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Also, the method for producing uridine 5'-diphospho-N-acetyl-α-D-glucosamine from uridine monophosphate and N-acetylglucosamine comprising the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Reworded, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) at least four enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the method for producing uridine 5'-diphospho-N-acetylglucosamine from uridine monophosphate and N-acetylglucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and optionally a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Polyphosphate serves as the only energy carrier in the inventive methods described herein and is used as a phosphate source in the regeneration of ATP from ADP using a polyphosphate kinase 3 (PPK3). The regeneration of ATP can be enhanced by adding a 1-domain polyphosphate kinase (1D-PPK), which also catalyzes the phosphorylation of ADP to ATP, preferably a 1-domain polyphosphate kinase 2 (1 D-PPK2) to the enzyme cascade of the inventive methods. Moreover, nucleoside phosphates, such as ADP are instable in aqueous media and tend to hydrolyze rapidly. To avoid the loss of ADP by hydrolysis to AMP, a 2-domain polyphosphate kinase (2D-PPK) which catalyzes the phosphorylation of AMP to ADP, preferably a 2-domain polyphosphate kinase 2 (2D-PPK2) can be added along with a 1 D-PPK or alone to the inventive enzyme cascade.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and a 1-domain polyphosphate kinase and/or a 2-domain polyphosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support without affecting the enzymatic activity of each enzyme. More preferably, the set of enzymes is co-immobilized on a reusable, mechanically stable solid support thereby increasing or retaining a large fraction of the activity of each enzyme.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and a 1-domain polyphosphate kinase and a 2-domain polyphosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and a 1-domain polyphosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and a 2-domain polyphosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support without affecting the enzymatic activity of each enzyme. More preferably, the set of enzymes is covalently co-immobilized on a reusable, mechanically stable solid support thereby increasing or retaining a large fraction of the activity of each enzyme.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate; and
 (iii) a set of enzymes comprising a glucose-1-phosphate uridylyltransferase, an N-acetylhexosamine kinase, a polyphosphate kinase, and a uridine monophosphate kinase and a 1-domain polyphosphate kinase and/or a 2-domain polyphosphate kinase and optionally a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

As ATP is continuously regenerated from ADP and polyphosphate in the inventive methods described herein, the production of UDP-GlcNAc can be performed with catalytic amount of ATP.

Preferably, the method for producing uridine 5'-diphospho-N-acetyl-α-D-glucosamine comprises the following steps:
A) providing a solution comprising
 (i) uridine monophosphate and N-acetyl-D-glucosamine;
 (ii) polyphosphate, and adenosine triphosphate in a catalytic amount; and
 (iii) a set of enzymes comprising a glucose-1-phosphate uridylyltransferase, an N-acetylhexosamine kinase, a polyphosphate kinase, and a uridine monophosphate kinase and a 1-domain polyphosphate kinase and/or a 2-domain polyphosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

The term "catalytic amount" refers herein to a substoichiometric amount of ATP, i.e. an amount of ATP which is less than the amount of N-acetyl-D-glucosamine used in the in inventive method. Preferably, a catalytic amount of ATP ranges from 0.001 to 0.99 moles per mole N-acetyl-D-glucosamine. More preferably, a catalytic amount of ATP ranges from 0.001 to 0.9 moles per mole N-acetyl-D-glucosamine. More preferably, a catalytic amount of ATP ranges from 0.005 to 0.95 moles per mole N-acetyl-D-glucosamine. More preferably, a catalytic amount of ATP ranges from 0.01 to 0.9 moles per mole N-acetyl-D-glucosamine.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate in a catalytic amount; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support; and
wherein in step A) adenosine triphosphate is added in an amount of 0.001 moles to 0.9 moles per mole N-acetyl-D-glucosamine, more preferably in an amount of 0.002 moles to 0.8 moles per mole N-acetyl-D-glucosamine, more preferably in an amount of 0.003 moles to 0.7 moles per mole N-acetyl-D-glucosamine, more preferably in an amount of 0.003 moles to 0.5 moles per mole N-acetyl-D-glucosamine, more preferably in an amount of 0.003 moles to 0.2 moles per mole N-acetyl-D-glucosamine, more preferably in an amount of 0.003 moles to 0.1 moles per mole N-acetyl-D-glucosamine, and most preferably in an amount of 0.005 moles to 0.05 moles per mole N-acetyl-D-glucosamine.

In one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate in a catalytic amount; and
  (iii) a set of enzymes comprising a glucose-1-phosphate uridylyltransferase, an N-acetylhexosamine kinase, a polyphosphate kinase, and a uridine monophosphate kinase and a 1-domain polyphosphate kinase and/or a 2-domain polyphosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support; and
wherein in step A) adenosine triphosphate is added in an amount of 0.001 moles to 0.9 moles per mole N-acetyl-D-glucosamine, more preferably in an amount of 0.002 moles to 0.8 moles per mole N-acetyl-D-glucosamine, more preferably in an amount of 0.003 moles to 0.7 moles per mole N-acetyl-D-glucosamine, more preferably in an amount of 0.003 moles to 0.5 moles per mole N-acetyl-D-glucosamine, more preferably in an amount of 0.003 moles to 0.2 moles per mole N-acetyl-D-glucosamine, more preferably in an amount of 0.003 moles to 0.1 moles per mole N-acetyl-D-glucosamine, and most preferably in an amount of 0.005 moles to 0.05 moles per mole N-acetyl-D-glucosamine.

Preferably, ATP is present in the solution provided in step A) in a concentration between 0.05 mM and 100 mM, more preferably between 0.1 mM and 90 mM, more preferably between 0.1 mM and 50 mM, more preferably between 0.2 mM and 20 mM, more preferably between 0.2 mM and 10 mM, more preferably between 0.2 mM and 5 mM, and most preferably between 0.5 mM and 3 mM. Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate in a catalytic amount; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support; and
wherein in step A) the concentration of adenosine triphosphate in the solution is in the range of 0.5 mM to 3 mM.

In an alternative embodiment, ADP or AMP can be used instead of ATP in the inventive methods described herein. ATP is generated from AMP or ADP and polyphosphate in situ, so that the production of UDP-galactose can be performed with ADP or AMP as starting materials as well.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively immobilized on a reusable, mechanically stable solid support;
wherein the adenosine triphosphate in the solution of step A) is formed in situ from adenosine monophosphate.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support;
wherein the adenosine triphosphate in the solution of step A) is formed in situ from adenosine diphosphate.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support;
wherein the adenosine triphosphate in the solution of step A) is formed in situ from adenosine monophosphate and adenosine diphosphate.

Reworded, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, adenosine monophosphate and/or adenosine diphosphate and/or adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

In an alternative embodiment, ATP is used in excess of N-acetyl-D-glucosamine in order to increase the space-time yield. Preferably the amount of ATP ranges from 1 to 100 moles per mole N-acetyl-D-glucosamine, more preferably the amount of ATP ranges from 1.2 to 50 moles per mole N-acetyl-D-glucosamine, more preferably the amount of ATP ranges from 1.5 to 20 moles per mole N-acetyl-D-glucosamine and most preferably the amount of ATP ranges from 2 to 10 moles per mole N-acetyl-D-glucosamine.

Preferably, in the method of the present invention, the resulting solution in step A) has a pH value in a range of 5.0-10.0, preferred 5.5-9.5, more preferred 6.0-9.0, still more preferred 6.5-9.0, still more preferred 7.0-9.0 and most preferred a pH value in the range of 7.5 to 8.5.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support; and
wherein the resulting solution in step A) has a pH value in the range of 7.5 to 8.5.

In one embodiment of the present invention, the solution provided in step A) comprises $Mg^{2+}$ ions as cofactor for the catalytic activity of the set of enzymes. Preferably, $Mg^{2+}$ ions are present in the solution provided in step A) in a concentration between 1 mM and 200 mM, more preferably between 1 mM and 150 mM, more preferably between 2 mM and 150 mM, more preferably between 5 mM and 100 mM, more preferably between 10 mM and 90 mM, more preferably between 15 mM and 80 mM, more preferably between 20 mM and 80 mM and most preferably between 20 mM and 50 mM.

Thus, in one embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, adenosine triphosphate; and
  (iii) a set of enzymes comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support; and
wherein the resulting solution in step A) has a $Mg^{2+}$ concentration in the range of 20 mM and 80 mM, preferably between 20 mM and 50 mM.

In an alternative embodiment, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, adenosine triphosphate; and (iii) a set of enzymes comprising a glucose-1-phosphate uridylyltransferase, an N-acetylhexosamine kinase, a polyphosphate kinase, and a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively immobilized on a reusable, mechanically stable solid support; and wherein the resulting solution in step A) has a $Mg^{2+}$ concentration in the range of 20 mM and 150 mM.

The inventive method for producing UDP-N-acetyl-α-D-glucosamine is carried out with a set of immobilized enzymes. The enzymes are then immobilized on a solid support such that they retain their activity, substrate specificity, stereoselectivity and/or other properties. Suitable solid supports are for instance beads, monoliths, spheres, particles, a particle bed, a fiber mat, granules, a gel, a membrane, a hollow-fiber membrane, a mixed-matrix membrane, a surface or other solid phase material. In one embodiment, each enzyme, i.e. the glucose-1-phosphate uridylyltransferase, the N-acetylhexosamine kinase, the polyphosphate kinase, the uridine monophosphate kinase and optionally the pyrophosphatase, is immobilized on a solid support.

In one embodiment, only some of the enzymes of the set of enzymes are immobilized on a solid support. At least one enzyme selected from the set of enzymes comprising the glucose-1-phosphate uridylyltransferase, the N-acetylhexosamine kinase, the uridine monophosphate kinase, the polyphosphate kinase, and optionally a pyrophosphatase is immobilized on a solid support.

Also described herein is that, at least one enzyme selected from the set of enzymes comprising a glucose-1-phosphate uridylyltransferase, an N-acetyl-hexosamine kinase, a polyphosphate kinase, a uridine monophosphate kinase and optionally a pyrophosphatase is immobilized on a solid support. Preferably, the polyphosphate kinase is immobilized on a solid support. Preferably, the uridine monophosphate kinase is immobilized on a solid support. Preferably, the glucose-1-phosphate uridylyltransferase is immobilized on a solid support. Preferably, the N-acetylhexosamine kinase is immobilized on a solid support. Preferably, the pyrophosphatase is immobilized on a solid support.

Surprisingly it has been found that co-immobilization of the set of enzymes results in a higher productivity in the production of uridine 5'-diphospho-N-acetyl-α-D-glucosamine (FIG. 3) in comparison to separate immobilization of the enzymes of the set of enzymes. Thus, preferably the enzymes used in the inventive methods described herein are covalently or adsorptively co-immobilized on a solid support. Preferably the enzymes used in the inventive methods described herein are covalently or adsorptively co-immobilized on a reusable, mechanically stable solid support. Preferably the enzymes used in the inventive methods described herein are covalently or adsorptively co-immobilized on a robust solid support. Immobilization of sequentially acting enzymes within a confined space increases catalytic efficiency of conversion due to dramatic reduction in the diffusion time of the substrate. In addition, the in-situ formation of substrates generates high local concentrations that lead to kinetic enhancements and can equate to substantial cost savings. Co-immobilization is usually achieved by mixing the enzymes prior immobilization on a solid support.

The present invention is further directed to a method for producing uridine 5'-diphospho-N-acetyl-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, and a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate.

The present invention is further directed to a method for producing uridine 5'-diphospho-N-acetyl-α-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, a uridine monophosphate kinase, and optionally a pyrophosphatase;

B) producing uridine 5'-diphospho-N-acetyl-α-D-glucosamine from uridine monophosphate and N-acetyl-D-glucosamine in the presence of the set of enzymes, polyphosphate, and adenosine triphosphate.

The present invention is further directed to a method for producing uridine 5'-diphospho-N-acetyl-α-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, and a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support has the form of beads, monoliths, spheres, particles, a particle bed, a fiber mat, granules, a gel, a membrane, a hollow-fiber membrane, a mixed-matrix membrane or a surface. Preferably, the solid support has the form of beads.

In such embodiments, the immobilized enzymes can facilitate the production of uridine 5'-diphospho-N-acetyl-α-D-glucosamine from uridine monophosphate and N-acetyl-D-glucosamine, and after the reaction is complete the immobilized enzymes are easily retained (e.g., by retaining beads on which the enzymes are immobilized) and then reused or recycled in subsequent runs. Such immobilized biocatalytic processes allow for further efficiency and cost reduction. In addition, the inventive method can be conducted in a continuous manner by passing the feed solution of step A) through a reactor containing the set of enzymes immobilized on a solid support.

The present invention is further directed to a method for producing uridine 5'-diphospho-N-acetyl-α-D-glucosamine comprising the following steps:
A) providing a feed solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, and a uridine monophosphate kinase, wherein the solid support comprising the set of immobilized enzymes is located in a chemical reactor;
B) producing uridine 5'-diphospho-N-acetyl-α-D-glucosamine from uridine monophosphate and N-acetyl-D-glucosamine in the presence of the set of enzymes, polyphosphate, and adenosine triphosphate by continuously passing the feed solution from step A) through the chemical reactor loaded with the solid support comprising the set of immobilized enzymes.

Preferably, the method for producing uridine 5'-diphospho-N-acetyl-α-D-glucosamine comprises the following steps:
A) providing a feed solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, a uridine monophosphate kinase and a pyrophosphatase, wherein the solid support comprising the set of immobilized enzymes is located in a chemical reactor;
B) producing uridine 5'-diphospho-N-acetyl-α-D-glucosamine from uridine monophosphate and N-acetyl-D-glucosamine in the presence of the set of enzymes, polyphosphate, and adenosine triphosphate by continuously passing the feed solution from step A) through the chemical reactor loaded with the solid support comprising the set of immobilized enzymes.

Preferably, the method for producing uridine 5'-diphospho-N-acetyl-α-D-glucosamine comprises the following steps:
A) providing a feed solution comprising
  (i) uridine monophosphate and N-acetyl-D-glucosamine;
  (ii) polyphosphate, and adenosine triphosphate; and
  providing a set of enzymes covalently or adsorptively co-immobilized on a solid support comprising a glucose-1-phosphate uridylyltransferase, an N-acetylhexosamine kinase, a polyphosphate kinase, and a uridine monophosphate kinase and optionally a pyrophosphatase, wherein the solid support comprising the set of immobilized enzymes is located in a chemical reactor;
B) producing uridine 5'-diphospho-N-acetyl-α-D-glucosamine from uridine monophosphate and N-acetyl-D-glucosamine in the presence of the set of enzymes, polyphosphate, and adenosine triphosphate by continuously passing the feed solution from step A) through the chemical reactor loaded with the solid support comprising the set of immobilized enzymes.

Methods of enzyme immobilization are well-known in the art. The enzymes can be bound non-covalently or covalently, such as adsorption, covalent binding, ionic binding, metal binding, crosslinking or crystallization. Various methods for conjugation and immobilization of enzymes to solid supports (e.g., resins, membranes, beads, glass, etc.) are well known in the art and described in e.g.: Yi et al., Process Biochemistry 2007, 42, 895; Martin et al., Applied Microbiology and Biotechnology 2007, 76, 843; Koszelewski et al., Journal of Molecular Catalysis B: Enzymatic, 2010, 63, 39; Truppo et al., Org. Process Res. Dev., 2011, 15, 1033; Hermanson, G. T., Bioconjugate Techniques, Second Edition, Academic Press (2008); Mateo et al., Biotechnology Progress, 2002, 18, 629; and Bioconjugation Protocols: Strategies and Methods, In Methods in Molecular Biology, C. M. Niemeyer ed., Humana Press (2004).

The enzymes used in the inventive methods described herein, namely glucose-1-phosphate uridylyltransferase, N-acetylhexosamine kinase, polyphosphate kinase, uridine monophosphate kinase, 1-domain polyphosphate kinase, 2-domain polyphosphate kinase, and pyrophosphatase are well known to the skilled person and can be obtained by any method well known to the skilled person in the art. Particularly, the enzymes can be overexpressed in, isolated from or prepared by recombinant methods from microbiological cultures comprising bacterial cultures, such as E. coli, virus and phage cultures and eukaryotic cell cultures. The inventive methods described herein are not restricted to enzymes from the sources described in the experimental section. Thus, the inventive method can be performed with the above listed enzymes obtained from various sources using common protein expression or isolation techniques. Further, it is well known to the skilled person to adapt the preparation of the enzymes to the specific applications in which the method is used. For instance, the above listed enzymes can be expressed in E. coli by using bacterial growth media of non-animal origin, such as a Luria-Bertani broth comprising tryptone from soy.

In one embodiment the glucose-1-phosphate uridylyltransferase comprises an amino acid sequence as set forth in SEQ ID NO: 4 or in SEQ ID NO: 10, or an amino acid sequence having at least 80% sequence identity to said sequence. In one embodiment the N-acetylhexosamine kinase comprises an amino acid sequence as set forth in SEQ ID NO: 1, or an amino acid sequence having at least 80% sequence identity to said sequence. In one embodiment the polyphosphate kinase comprises an amino acid sequence as set forth in SEQ ID NO: 3, or an amino acid sequence having at least 80% sequence identity to said sequence. In one embodiment the uridine monophosphate kinase comprises an amino acid sequence as set forth in SEQ ID NO: 2, or an amino acid sequence having at least 80% sequence identity to said sequence. In one embodiment the 1-domain polyphosphate kinase comprises an amino acid sequence as set forth in SEQ ID NO: 6, or an amino acid sequence having at least 80% sequence identity to said sequence. In one embodiment the 2-domain polyphosphate kinase comprises an amino acid sequence as set forth in SEQ ID NO: 7, or an amino acid sequence having at least 80% sequence identity to said sequence. In one embodiment the pyrophosphatase comprises an amino acid sequence as set forth in SEQ ID NO: 5, or an amino acid sequence having at least 80% sequence identity to said sequence.

Thus, in one embodiment the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, a uridine monophosphate kinase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, the glucose-1-phosphate uridylyltransferase comprises an amino acid sequence as set forth in SEQ ID NO: 4, or an amino acid sequence having at least 80% sequence identity to said sequence; wherein the N-acetylhexosamine kinase comprises an amino acid sequence as set forth in SEQ ID NO: 1, or an amino acid sequence having at least 80% sequence identity to said sequence. Wherein the polyphosphate kinase comprises an amino acid sequence as set forth in SEQ ID NO: 3, or an amino acid sequence having at least 80% sequence identity to said sequence, wherein the uridine monophosphate kinase comprises an amino acid sequence as set forth in SEQ ID NO: 2, or an amino acid sequence having at least 80% sequence identity to said sequence; wherein the 1-domain polyphosphate kinase comprises an amino acid sequence as set forth in SEQ ID NO: 6, or an amino acid sequence having at least 80% sequence identity to said sequence; wherein the 2-domain polyphosphate kinase comprises an amino acid sequence as set forth in SEQ ID NO: 7, or an amino acid sequence having at least 80% sequence identity to said sequence; wherein the pyrophosphatase comprises an amino acid sequence as set forth in SEQ ID NO: 5, or an amino acid sequence having at least 80% sequence identity to said sequence; and wherein the set of enzymes is covalently or adsorptively immobilized on a reusable, mechanically stable solid support.

The enzyme-containing solutions obtained from fermentation process, cell homogenization or cell lysis, which are usually centrifuged and filtered to remove cell debris, can be directly used for immobilizing the enzymes on a solid support. Thus, no further purification step or isolation step is required and the the fermentation broth, (crude or purified) cell lysate or cell homogenate can be used for immobilizing the enzymes on a solid support such that they retain their activity, substrate specificity, stereoselectivity and/or other properties.

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support from fermentation broth, crude cell lysate, purified cell lysate or cell homogenate.

Preferably, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is immobilized on a reusable, mechanically stable solid support from crude cell lysate or cell homogenate.

Preferably, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support from fermentation broth without prior purification.

Reworded, the method for producing uridine 5'-diphospho-N-acetyl-α-D-glucosamine comprises the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support from fermentation supernatant without prior purification.

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently co-immobilized on a reusable, mechanically stable solid support from cell lysate or cell homogenate.

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyltransferase, an N-acetylhexosamine kinase, a polyphosphate kinase, a uridine monophosphate kinase and a pyrophosphatase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively immobilized on a reusable, mechanically stable solid support from cell lysate or cell homogenate.

Thus, the present invention is further directed to a method for producing uridine 5'-diphospho-N-acetyl-α-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes immobilized on a solid support comprising a glucose-1-phosphate uridylyl-transferase, an N-acetylhexosamine kinase, a polyphosphate kinase, a uridine monophosphate kinase and optionally a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively co-immobilized on a reusable, mechanically stable solid support from cell lysate or cell homogenate.

Thus, the present invention is further directed to a method for producing uridine 5'-diphospho-N-acetyl-α-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyl-transferase, an N-acetylhexosamine kinase, a polyphosphate kinase, a uridine monophosphate kinase, a 1-domain polyphosphate kinase and/or a 2-domain polyphosphate kinase, and optionally a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the set of enzymes is covalently or adsorptively co-immobilized on a reusable, mechanically stable solid support from cell lysate or cell homogenate.

Solid supports useful for immobilizing the enzymes used in the method of the present invention include but are not limited to beads, monoliths, spheres, particles, a particle bed, a fiber mat, granules, a gel, a membrane, a hollow-fiber membrane, a mixed-matrix membrane or a surface. Preferably, the solid support has the form of beads.

Preferred are solid supports that allow for covalent immobilization of enzymes and/or adsorptive immobilization of enzymes. Covalent immobilization or covalent binding as used herein refers to the formation of a covalent chemical bond between the enzyme and a functional reactive group on the reusable, mechanically stable solid support such that the enzyme attaches to the solid support and retains large part of or increases its activity, substrate specificity, stereoselectivity and/or other properties. Therefore, solid supports that allow for covalent immobilization of enzymes exhibit a functional reactive group (e.g. chloride, epoxide, vinyl groups, carboxylic groups, etc.) that binds to a reactive group present on a side chain of the amino acids, either directly or via a bivalent linker molecule.

Particularly preferred are solid supports for covalent binding that are functionalized with epoxide functional groups. Further preferred solid supports include, but are not limited to solid supports with ethylenediamine functional groups, with epoxy functional groups and further functionalized with a hydrophobic group, such as butyl, octyl, methyl, phenyl, for example with epoxide functional groups and butyl functional groups, with amino C2 spacer functional groups, with amino C6 spacer functional groups, or other amino spacer such as amino C3 spacer, amino C4 spacer, amino C5 spacer, amino C7 spacer, with epoxy functional groups, with anionic/amino C6 spacer functional groups, with anionic/tertiary amine functional groups, anionic/quaternary amine functional groups, with cationic/sulphonic functional groups, with carboxylic ester functional groups, with phenyl functional groups, with octadecyl functional groups, with styrene/methyl functional groups, macroporous resins or beads.

The solid support may consist of a polymeric material, non-polymeric material, e.g. silica gel. The solid support may consists of a polymeric material including, but not limited to polymethacrylate, polyacrylic acid, acrylic polymer, polystyrene, styrene, styrene/methacrylate and mixtures thereof.

Examples of solid supports useful for immobilizing the enzymes used in the method of the present invention include but are not limited to beads or resins comprising polymethacrylate with epoxide functional groups, polymethacrylate with amino epoxide functional groups, polymethacrylate with ethylenediamine functional groups, polymethacrylate with epoxide functional groups and further functionalized with a hydrophobic group, such as butyl, octyl, methyl, phenyl, for example polymethacrylate with epoxide functional groups and butyl functional groups, polymethacrylate with amino C2 spacer functional groups, polymethacrylate with amino C6 spacer functional groups, polyacrylic acid with epoxy functional groups, acrylic polymer with epoxy functional groups polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, magnetic silica particles with Ni-NTA functional group, or magnetic nanoparticles with a core of magnetite and a dextran shell with Ni-NTA functional group, macroporous resins or beads of macroporous styrene or styrene/methacrylate. While, in principle, any suitable solid support known in the art can be used in the inventive method, Ni agarose beads or Ni NTA agarose resins are not preferred for the reasons as set forth above.

Thus, the present invention is further directed to a method for producing uridine 5'-diphospho-N-acetyl-α-D-glucosamine comprising the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the immobilized set of enzymes, polyphosphate, and adenosine triphosphate, wherein the set of enzymes is covalently immobilized on a reusable, mechanically stable solid support selected from polymethacrylate with epoxide functional groups, polymethacrylate with amino epoxide functional groups, polymethacrylate with ethylenediamine functional groups, polymethacrylate with epoxide functional groups and further functionalized with a hydrophobic group, such as butyl, octyl, methyl, phenyl, for example polymethacrylate with epoxide functional groups and butyl functional groups, polymethacrylate with amino C2 spacer functional groups, polymethacrylate with amino C6 spacer functional groups, polyacrylic acid with epoxy functional groups, acrylic polymer with epoxy functional groups polyacrylic acid with anionic/amino C6 spacer functional groups, polyacrylic acid with anionic/tertiary amine functional groups, polystyrene with anionic/quaternary amine functional groups, polystyrene with cationic/sulphonic functional groups, polyacrylic acid with carboxylic ester functional groups, polystyrene with phenyl functional groups, polymethacrylate with octadecyl functional groups, polystyrene with styrene/methyl functional groups, and macroporous resins or beads of macroporous styrene or styrene/methacrylate.

Exemplary solid supports useful for immobilizing the enzymes used in the inventive method include, but are not limited to, Sepabeads/ReliZyme (Resindion): EC-EP, including EC-EP/S and EC-EP/M, EP112/S, EP112/M, EP113/S, EP113/M, EP403/M, EP403/S, HFA403M, HFA403S, HG403, EP400/SS EC-HG, EC-HFA, EC-EA/M, EA403/S and EC-HA including EC-HA/S and EC-HA/M; Immobeads (ChiralVision) Imm150P, IB-COV1, IB-COV2, IB-COV3, IB-ANI1, IB-ANI2, IB-ANI3, IB-ANI4, IB-CAT1, IB-ADS1, IB-ADS2, IB-ADS3 and IB-ADS4, IB-CAT-1, IB-ANI-1, IB-ANI-2, IB-ANI-3, IB-ANI-4; Eupergit (Rohm GmbH & Co. KG) and magnetic particles (micromod GmbH): Nano-mag, Sicastar-6 and Sicastar-1.5, enzyme immobilization resins Lifetech™ (Purolite): Epoxy methacrylate: ECR8215, ECR8215F, ECR8215M, ECR8206, ECR8206F, ECR8206M, ECR8204, ECR8204F, ECR8204M, ECR8209, ECR8209F, ECR8209M, ECR8285, ECR8285F, ECR8285M, Amino C2 or C6 methacrylate: ECR8305, ECR8305F, ECR8305M, ECR8309, ECR8309F, ECR8309M, ECR8315, ECR8315F, ECR8315M, ECR8404 ECR8404F, ECR8404M, ECT8409, ECT8409F, ECT8409M, ECR8415, ECR8415F, ECR8415M, macroporous resins ECR1090, ECR1091, ECR1091M, ECR1061, ECR1030, ECR1030F, ECR8806F; ionic resins ECR1504, ECR1508, ECR1604, ECR1640, and magnetic particles (micromod GmbH): Nano-mag-D and Sicastar-M-CT.

Solid support materials which result in mechanically stable beads or resins with enzymes immobilized thereon are preferred with regard to reuse and/or recycling of the beads or resins for the production of UDP-GlcNAc and more preferred with regard to a continuous process of the method for production of UDP-GlcNAc. A mechanically stable solid support is characterized in resistance to abrasion, mechanical stress and is suitable for a high number of cycles, such as at least 10, more preferably at least 12, more preferably at least 14, more preferably at least 16, more preferably at least 18, and most preferably at least 20 cycles. It could be shown that immobilization of enzymes through covalent binding to a solid support provides mechanically stable beads or resins, which has been shown to be particularly suitable for reuse and/or recycling of the resins or beads with immobilized enzymes for the production of UDP-GlcNAc. Surprisingly it has been found that with beads or resins comprising a polymer with epoxide functional groups, such as for example, but not limited to polymethacrylate with epoxide functional groups, polymethacrylate with amino epoxide functional groups, polymethacrylate with ethylenediamine functional groups, polymethacrylate with epoxide functional groups and butyl functional groups polyacrylic acid with epoxy functional groups, acrylic polymer with epoxy functional groups, that allow covalent binding of the enzymes to be immobilized, mechanically robust resins or beads may be obtained.

Thus, reusable, mechanically stable solid support in form of beads or resins with enzymes immobilized thereon are preferred with regard to co-immobilization of the set of enzymes from crude cell lysate or crude cell homogenate, and with regard to retaining larges parts of or increasing the activity of all enzymes co-immobilized and with regard to reuse and/or recycling of the beads or resins for the production of UDP-GlcNAc and with regard to a continuous process of the method for production of UDP-GlcNAc. The solid supports are inter alia characterized in resistance to abrasion, mechanical stress and are suitable for a high number of cycles, such as at least 10, more preferably at least 12, more preferably at least 14, more preferably at least 16, more preferably at least 18, and most preferably at least 20 cycles. It could be shown that immobilization of enzymes through covalent binding to a solid support provides mechanically robust beads or resins, which has been shown to be particularly suitable for reuse and/or recycling of the resins or beads with immobilized enzymes for the production of UDP-GlcNAc, which allows the co-immobilization of the set of enzymes from crude cell lysate and which retains large parts of or increases the activity of all enzymes co-immobilized. Surprisingly it has been found that with beads or resins comprising epoxide functional groups, amino epoxide functional groups, ethylenediamine functional groups, or epoxide functional groups and a hydrophobic group, such as butyl, octyl, methyl, phenyl, butyl functional groups that allow covalent binding of the enzymes to be immobilized, robust solid resins or beads may be obtained.

Thus, the present invention is further directed to a method for producing uridine 5'-diphospho-N-acetyl-α-D-glucosamine comprising the following steps:
A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the immobilized set of enzymes, polyphosphate, and adenosine triphosphate,
wherein the set of enzymes is covalently immobilized on a reusable, mechanically stable beads or resins comprising epoxide functional groups, amino epoxide functional groups, ethylenediamine functional groups, or epoxide functional groups and a hydrophobic group, such as butyl, octyl, methyl, phenyl, butyl functional groups.

Epoxy-activated resins or beads allow multipoint covalent binding between an enzyme and the resin or bead. Preferably the resin backbone is composed of methacrylate with porosities of 0.01 nm to 10000 nm or 0.1 Å to 100000 Å. In a preferred embodiment the porosity of an epoxy functionalized resin or bead, for example an epoxy methacrylate resin or bead, may be 30 nm to 60 nm. In a preferred embodiment the porosity of an epoxy methacrylate resin or bead may be nm to 60 nm. In a preferred embodiment the porosity of an epoxy functionalized resin or bead, for example an epoxy methacrylate resin or bead, may be 50 nm to 60 nm. In a preferred embodiment the porosity of an epoxy functionalized resin or bead, for example an epoxy methacrylate resin or bead, may be 60 nm to 120 nm. In a preferred embodiment the porosity of an epoxy functionalized resin or bead, for example an epoxy methacrylate resin or bead, may be 120 nm to 180 nm. The epoxy functionalized resin or bead, for example an epoxy methacrylate resin or bead, may form very stable covalent linkages with different protein groups, such as amino, thiol, phenolic, preferably under very mild pH and temperature conditions. The resins are preferably mechanically stable and the resin with immobilized enzymes may be preferably used in a stirred tank or column reactor.

Amino resins, such as amino C2 functionalized resins or amino C6 functionalized resins or other amino resins such as amino C3, amino C4, amino C5, amino C7 and so on, such as for example but not limited to amino C2 methacrylate resins or amino C6 methacrylate resins may pre-activated, for example by glutaraldehyde and then used in the covalent immobilization of enzyme. Reaction of the aldehyde groups with amino groups of enzymes form Schiff bases which results in multipoint covalent binding. A linkage may be also achieved by reduction with borohydrides. Thus a reversible immobilization may become irreversible by means of crosslinking step: the enzyme may be adsorbed onto the carrier and then crosslinked by using, for example, glutaraldehyde. The crosslinked enzyme or the crosslinked enzyme may cover the carrier like a net. Amino functionalized resins, such as amino C2 methacrylate resins or amino C6 methacrylate resins have preferably porosities in the range of 30 nm to 180 nm or 300 Å to 1800 Å. In a preferred embodiment the porosity of an amino functionalized resin, such as amino C2 methacrylate resin or bead or of an amino C6 methacrylate resin or bead may be nm to 60 nm. In a preferred embodiment the porosity of an amino functionalized resin, such as an amino C2 methacrylate resin or bead or of an amino C6 methacrylate resin or bead may be 60 nm to 120 nm. In a preferred embodiment the porosity of an amino functionalized resin, such as an amino C2 methacrylate resin or bead or of an amino C6 methacrylate resin or bead may be 120 nm to 180 nm.

Another method for irreversible immobilization is the activation of hydroxyl functional groups, such as for example for 1,2-diol-functionalized resins or beads.

Thus, particularly preferred are beads or resins comprising polymethacrylate with epoxide functional groups and polymethacrylate with amino epoxide functional groups. Preferably the beads or resins comprising polymethacrylate with epoxide functional groups are hydrophilic. Covalent enzyme immobilization is particularly preferred. In preferred embodiments the beads or resins are not functionalized with apolar groups such as butyl or octadecyl groups. In preferred embodiments the resins or beads are hydrophilic.

Preferably, the solid support is composed of a resin or beads selected from: sepabeads (Resindion): EC-EP, EP113/M, EP403/M, EP403/S, HFA403, EA403, HA403, EC-EA/M and EC-HA; immobeads (ChiralVision) IB-COV1, IB-COV2, IB-COV3, IB-ANI1, IB-ANI1, IB-CAT1; Eupergit (Röhm GmbH & Co. KG), enzyme immobilization resins (Purolite): Epoxy methacrylate: ECR8215, ECR8215F, ECR8215M, ECR8206, ECR8206F, ECR8206M, ECR8204, ECR8204F, ECR8204M, ECR8209, ECR8209F, ECR8209M, ECR8285, ECR8285F, ECR8285M, Amino C2 or C6 methacrylate: ECR8305, ECR8305F, ECR8305M, ECR8309, ECR8309F, ECR8309M, ECR8315, ECR8315F, ECR8315M, ECR8404 ECR8404F, ECR8404M, ECT8409, ECT8409F, ECT8409M, ECR8415, ECR8415F, ECR8415M.

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the immobilized set of enzymes, polyphosphate, and adenosine triphosphate,
wherein the set of enzymes is covalently or adsorptively immobilized on a reusable, mechanically stable solid support selected from EC-EP, EP113/M, EP403/M, EP403/S, HFA403, EA403, HA403, EC-EA/M and EC-HA, IB-COV1, IB-COV2, IB-COV3, IB-ANI1, IB-ANI1, IB-CAT1; Eupergit (Röhm GmbH & Co. KG), enzyme immobilization resins (Purolite): Epoxy methacrylate: ECR8215, ECR8215F, ECR8215M, ECR8206, ECR8206F, ECR8206M, ECR8204, ECR8204F, ECR8204M, ECR8209, ECR8209F, ECR8209M, ECR8285, ECR8285F, ECR8285M, Amino C2 or C6 methacrylate: ECR8305, ECR8305F, ECR8305M, ECR8309, ECR8309F, ECR8309M, ECR8315, ECR8315F, ECR8315M, ECR8404 ECR8404F, ECR8404M, ECT8409, ECT8409F, ECT8409M, ECR8415, ECR8415F, and ECR8415M.

Preferably, the solid support is composed of a resin or beads selected from: sepabeads (Resindion): EC-EP, EP113/M, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (Röhm GmbH & Co. KG).

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes covalently or adsorptively immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the solid support is hydrophilic. Preferably the enzymes are immobilized to the solid support through covalent binding.

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes covalently or adsorptively immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is a functionalized methacrylate resin or bead.

Thus, the present invention is preferably directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is a functionalized resin or bead comprising epoxide functional groups or amino epoxide functional groups. Preferably the solid support is a resin or bead comprising a polymer with epoxide functional groups or amino epoxide functional groups. More preferably the solid support is a resin or bead comprising a polymer with epoxide functional groups.

Thus, the present invention is further directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is a functionalized resin or bead comprising a polymer with epoxide functional groups or amino epoxide functional groups.

Thus, the present invention is further directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is a functionalized methacrylate resin or bead comprising epoxide functional groups or amino epoxide functional groups.

Thus, the present invention is further directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is composed of a resin or beads selected from sepabeads (Resindion): EC-EP, EP403, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (Röhm GmbH & Co. KG).

Thus, the present invention is further directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently or adsorptively immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is composed of a resin or beads selected from: sepabeads (Resindion): EC-EP, EP403/M, EP403/S, EC-HFA, HFA403, HFA403/M, HFA 403/S, immobeads (ChiralVision) IB-COV2, IB-COV3, (Purolite) ECR8215, ECR8215F, ECR8215M, ECR8204F, ECR8204M, ECR8204, ECR8209F, ECR8209M, ECR8209; Eupergit (Röhm GmbH & Co. KG).

Also, the present invention is further directed to a method for producing uridine 5'-diphospho-N-acetyl-α-D-glucosamine comprising the following steps:
A) providing a solution comprising
 (i) uridine monophosphate and N-acetyl-D-glucosamine;
 (ii) polyphosphate, and adenosine triphosphate; and
 providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate, wherein the solid support is composed of beads or resins comprising polymethylmethacrylate with epoxide functional groups, polymethacrylate with epoxide functional groups, polymethacrylate with amino epoxide functional groups, polymethacrylate with ethylenediamine functional groups, polymethacrylate with amino C2 functional groups, polymethacrylate with amino C6 functional groups, polyacrylic acid with epoxy functional groups, polyacrylic acid with anionic/amino C6 spacer functional groups.

In one embodiment, the enzymes are covalently immobilized on a methacrylate polymer functionalized with epoxy groups as solid support. Such a methacrylate polymer possesses a high mechanical strength which makes it suitable for use in reactors in multiple runs or cycles. The epoxy groups form very stable covalent bonds with the enzymes of the UDP-GlcNAc cascade such that they retain their activity, substrate specificity, stereoselectivity and/or other properties, thereby minimizing the premature wash-off of the enzymes during synthesis. Thus, the inventors have shown that full conversion of N-acetyl-D-glucosamine and UMP to UDP-N-acetyl-D-glucosamine can be achieved even if the solid support on which the enzymes are covalently immobilized is reused in multiple cycles.

Moreover, the inventors have surprisingly found that the enzyme activity can be even increased when a methacrylate polymer functionalized with epoxy groups is used as solid support in more than 3 batch cycles. Therefore, the reuse of said solid support in multiple runs or cycles significantly improves the productivity of the inventive methods described herein (see FIG. 33).

Thus, the present invention is further directed to a method for producing uridine 5'-diphospho-N-acetyl-α-D-glucosamine comprising the following steps:
A) providing a solution comprising
  (i) uridine monophosphate and N-acetyl-D-glucosamine;
  (ii) polyphosphate, and adenosine triphosphate; and
  providing a set of enzymes covalently immobilized on a reusable, mechanically stable solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the solid support is composed of beads or resins comprising polymethacrylate with amino epoxide functional groups or polymethacrylate with epoxide functional groups. Preferably, said solid support has a particle size between 100 μm and 300 μm. Preferably, said solid support has a pore diameter between 40 nm and 60 nm. Preferably, said solid support is selected from HFA403/S or EP403/S.

Preferably the enzymes are co-immobilized on a polymer functionalized with epoxy groups which may be used in reactors in multiple runs or cycles. Preferably the enzymes co-immobilized on a solid support may be used in at least 3 cycles, more preferably in at least 4 cycles, more preferably in at least 5 cycles, more preferably in at least 6 cycles, more preferably in at least 7 cycles, more preferably in at least 8 cycles, more preferably in at least 9 cycles, more preferably in at least 10 cycles, more preferably in at least 12 cycles, more preferably in at least 14 cycles, more preferably in at least 16 cycles, more preferably in at least 18 cycles, more preferably in at least 20 cycles, more preferably in at least 25 cycles, more preferably in at least 25 cycles, more preferably in at least 30 cycles, and most preferably in at least 50 cycles. Preferably the enzymes are co-immobilized on a solid support and may be used in at least 3-10, preferably 5-12, more preferably 7-14, more preferably 9-16 and even more preferably at least 10-20 runs or cycles.

In preferred embodiments, epoxy beads or resin with immobilized set of enzymes, preferably co-immobilized set of enzymes, allow in general UDP-GlcNAc synthesis in more than 3 cycles, preferably more than 5 cycles, preferably more than 10 cycles, and preferably even more than 20 cycles. The synthesis of UDP-GlcNAc in such a large number of cycles is a significant improvement of the process and has not been reported before in the prior art. For example as shown in FIG. 33 and as demonstrated in Example 4 Ni agarose beads or Ni NTA agarose resins are not reusable mechanically stable solid supports according to the present invention and cannot be reused in more than 2 cycles. Thus, as mentioned above Ni agarose beads or Ni NTA agarose resins are not preferred. Preferably a reusable, mechanically stable solid support does not relate to Ni agarose beads or Ni NTA agarose resins.

Thus, a further aspect of the present invention is directed to a set of enzymes comprising a glucose-1-phosphate uridylyltransferase, an N-acetylhexosamine kinase, a polyphosphate kinase, and a uridine monophosphate kinase; wherein the set of enzymes is co-immobilized on a polymer functionalized with epoxy groups.

Thus, a further aspect of the present invention is directed to a set of enzymes comprising a glucose-1-phosphate uridylyltransferase, an N-acetylhexosamine kinase, a polyphosphate kinase, and a uridine monophosphate kinase; wherein the set of enzymes is co-immobilized on a polymer functionalized with amino epoxy groups.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

Thus, a further aspect of the present invention is directed to a set of enzymes comprising a glucose-1-phosphate uridylyltransferase, an N-acetylhexosamine kinase, a polyphosphate kinase, and a uridine monophosphate kinase; wherein the set of enzymes is co-immobilized on a methacrylate polymer functionalized with epoxy groups.

Thus, a further aspect of the present invention is directed to a set of enzymes comprising a glucose-1-phosphate uridylyltransferase, an N-acetylhexosamine kinase, a polyphosphate kinase, and a uridine monophosphate kinase; wherein the set of enzymes is co-immobilized on a methacrylate polymer functionalized with amino epoxy groups.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

Preferably, the methacrylate polymer has the form of beads. Preferably, the beads have a particle size in the range of 150 μm-300 μm. Preferably, the methacrylate polymer is porous with a pore diameter between 600 Å-1200 Å. In one embodiment, the methacrylate polymer is of low porosity having a pore diameter between 300 Å-600 Å. In one embodiment, the methacrylate polymer is of low porosity having a pore diameter between 450 Å-650 Å. In one embodiment, the methacrylate polymer is of high porosity having a pore diameter between 1200 Å-1800 Å. In one embodiment, the methacrylate polymer is further functionalized with butyl groups. In one embodiment, the methacrylate polymer is further functionalized with a hydrophobic group such as butyl, methyl, phenyl, octyl.

In a further embodiment of the present invention, the method for producing uridine 5'-diphospho-N-acetyl-α-D-glucosamine comprises the additional step C):
C) isolating the uridine 5'-diphospho-N-acetyl-α-D-glucosamine.

In a further embodiment of the present invention, the method for producing uridine 5'-diphospho-N-acetyl-α-D-glucosamine comprises the additional step C):
C) isolating the uridine 5'-diphospho-N-acetyl-α-D-glucosamine by ion exchange chromatography.

Thus, the present invention is further directed to a method for producing uridine 5'-diphospho-N-acetyl-α-D-glucosamine comprising the following steps:
A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetyl-α-D-glucosamine,
wherein the set of enzymes is covalently or adsorptively immobilized on a reusable, mechanically stable solid support.

Preferably, the set of enzymes is covalently co-immobilized on a reusable, mechanically stable solid support, thereby increasing or retaining a large fraction of the activity of each enzyme.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase.

Preferably, the present invention is further directed to a method for producing uridine 5'-diphospho-N-acetyl-α-D-glucosamine comprising the following steps:
A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, a uridine monophosphate kinase and a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetyl-α-D-glucosamine,
wherein at least one enzyme of the set of enzymes is immobilized on a reusable, mechanically stable solid support.

Preferably the set of enzymes is covalently or adsorptively immobilized on a reusable, mechanically stable solid support. Preferably, the set of enzymes is covalently co-immobilized on a reusable, mechanically stable solid support thereby increasing or retaining a large fraction of the activity of each enzyme.

Preferably, the present invention is further directed to a method for producing uridine 5'-diphospho-N-acetyl-α-D-glucosamine comprising the following steps:
A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, a uridine monophosphate kinase and optionally a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetyl-α-D-glucosamine,
wherein the set of enzymes is covalently or adsorptively immobilized on a reusable, mechanically stable solid support.

Preferably, the present invention is further directed to a method for producing uridine 5'-diphospho-N-acetyl-α-D-glucosamine comprising the following steps:
A) providing a solution comprising
   (i) uridine monophosphate and N-acetyl-D-glucosamine;
   (ii) polyphosphate, and adenosine triphosphate; and
   providing a set of enzymes covalently or adsorptively co-immobilized on a reusable, mechanically stable solid support comprising a glucose-1-phosphate uridylyltransferase, an N-acetylhexosamine kinase, a polyphosphate kinase, a uridine monophosphate kinase and optionally a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetyl-α-D-glucosamine,
wherein the set of enzymes is co-immobilized on a solid support from cell lysate. More preferably, the set of enzymes is covalently or adsorptively co-immobilized on a reusable, mechanically stable solid support thereby increasing or retaining a large fraction of the activity of each enzyme.

In one embodiment of the present invention, uridine 5'-diphospho-N-acetyl-α-D-glucosamine is produced from uridine and N-acetylglucosamine. Thus, uridine monophosphate in step A) of the inventive methods is obtained from uridine, adenosine phosphate and a uridine kinase enzyme. Thus, the method for producing uridine 5'-diphospho-N-acetyl-α-D-glucosamine comprises the following steps:
A) providing a solution comprising
   (i') uridine and N-acetyl-D-glucosamine;
   (ii) polyphosphate, and adenosine triphosphate;
   providing a set of enzymes comprising a uridine kinase, a glucose-1-phosphate uridylyltransferase, an N-acetylhexosamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support, thereby increasing or retaining a large fraction of the activity of each enzyme.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support.

In one embodiment of the present invention, uridine 5'-diphospho-N-acetyl-α-D-glucosamine is produced from uracil, 5-phospho-α-D-ribose 1-diphosphate (PRPP) and N-acetyl-D-glucosamine. Thus, uridine monophosphate in step A) of the inventive methods is obtained from uracil, 5-phospho-α-D-ribose 1-diphosphate and a uracil phosphoribosyltransferase enzyme. Thus, the method for producing uridine 5'-diphospho-N-acetyl-α-D-glucosamine comprises the following steps:

A) providing a solution comprising
  (i') uracil, phospho-α-D-ribose 1-diphosphate, and N-acetyl-D-glucosamine;
  (ii) polyphosphate, and adenosine triphosphate;
  providing a set of enzymes comprising a uracil phosphoribosyltransferase, a glucose-1-phosphate uridylyltransferase, an N-acetylhexamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support.

In one embodiment of the present invention, uridine 5'-diphospho-N-acetyl-α-D-glucosamine is produced from orotic acid, 5-phospho-α-D-ribose 1-diphosphate (PRPP) and N-acetyl-D-glucosamine. Orotic acid is phosphorylated in the presence of an orotate phosphoribosyltransferase and the formed oritidine 5'-phosphate (OMP) is decarboxylated to uridine monophosphate by a UMP synthase. Thus, uridine monophosphate in step A) of the inventive methods is obtained from orotic acid, 5-phospho-α-D-ribose 1-diphosphate, an orotate phosphoribosyltransferase and a UMP synthase enzyme. Thus, the method for producing uridine 5'-diphospho-N-acetyl-α-D-glucosamine comprises the following steps:

A) providing a solution comprising
  (i') orotic acid, phospho-α-D-ribose 1-diphosphate, and N-acetyl-D-glucosamine;
  (ii) polyphosphate, and adenosine triphosphate;
  providing a set of enzymes comprising an orotate phosphoribosyltransferase, a UMP synthase, a glucose-1-phosphate uridylyltransferase, an N-acetyl-hexamine kinase, a polyphosphate kinase, and a uridine monophosphate kinase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the set of enzymes further comprises a pyrophosphatase. Preferably, the set of enzymes further comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, the set of enzymes is immobilized or co-immobilized on a solid support.

GlcNAcylated Saccharides, GlcNAcylated Glycopeptides, GlcNAcylated Glycoproteins, GlcNAcylated Proteins, GlcNAcylated Peptides, GlcNAcylated Bioconjugates and GlcNAcylated Small Molecules.

In a further aspect of the present invention the inventive methods described herein are useful for producing GlcNAcylated saccharides, GlcNAcylated glycopeptides, GlcNAcylated glycoproteins, GlcNAcylated proteins, GlcNAcylated peptides or GlcNAcylated small molecules. GlcNAcylation as used herein refers to the functionalization of a saccharide, glycopeptide, glycoprotein, protein, peptide or small molecule with N-acetyl-D-glucosamine by enzymatic-catalyzed reaction with UDP-N-acetyl-α-D-glucosamine. Glycosyltransferases are enzymes that catalyze the reaction between UDP-N-acetyl-α-D-glucosamine and an available hydroxyl group of a saccharide, glycopeptide, glycoprotein, protein, peptide or small molecule.

Thus, in one embodiment of the present invention the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Thus, in one embodiment of the present invention the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, a uridine monophosphate kinase and a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetylglucosamine,
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Thus, in one embodiment of the present invention the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, a uridine monophosphate kinase and optionally a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
C) isolating the uridine 5'-diphospho-N-acetyl-α-D-glucosamine,
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

The glycosyltransferase catalyzes the reaction of UDP-GlcNAc with an available hydroxyl group of a saccharide, glycopeptide, glycoprotein, protein, peptide, bioconjugate or small molecule, thereby forming a GlcNAcylated saccharide, GlcNAcylated glycopeptide, GlcNAcylated glycoprotein, a GlcNAcylated protein, a GlcNAcylated peptide, a GlcNAcylated bioconjugate or a GlcNAcylated small molecule and uridine diphosphate (UDP) as side product. UDP being an intermediate product formed in step B), specifically in step (b2') can then be reused or recycled.

Thus, in one embodiment of the present invention the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes co-immobilized on a solid support comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate by
  (a) forming N-acetylglucosamine 1-phosphate (GlcNAc-1-P) from N-acetylglucosamine and adenosine triphosphate being catalyzed by an N-acetylhexosamine kinase,
  (b1) forming uridine diphosphate (UDP) from uridine monophosphate and adenosine triphosphate being catalyzed by a uridine monophosphate kinase;
  (b2) forming uridine triphosphate (UTP) from uridine diphosphate and polyphosphate being catalyzed by a polyphosphate kinase; and
  (c) reacting N-acetylglucosamine 1-phosphate with uridine triphosphate to UDP-N-acetylglucosamine in the presence of a glucose-1-phosphate uridylyltransferase
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase.
E) recycling the in-situ formed uridine diphosphate to form uridine triphosphate, wherein set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Thus, in one embodiment of the present invention the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, a uridine monophosphate kinase and a pyrophosphatase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate by
  (a) forming N-acetylglucosamine 1-phosphate (GlcNAc-1-P) from N-acetylglucosamine and adenosine triphosphate being catalyzed by an N-acetylhexosamine kinase,
  (b1) forming uridine diphosphate (UDP) from uridine monophosphate and adenosine triphosphate being catalyzed by a uridine monophosphate kinase;
  (b2) forming uridine triphosphate (UTP) from uridine diphosphate and polyphosphate being catalyzed by a polyphosphate kinase; and
  (c') reacting N-acetylglucosamine 1-phosphate with uridine triphosphate to UDP-N-acetylglucosamine in the presence of a glucose-1-phosphate uridylyltransferase
  (c") converting pyrophosphate to phosphate in the presence of a pyrophosphatase.
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, bioconjugate peptide or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of a glycosyltransferase.
E) recycling the in-situ formed uridine diphosphate to form uridine triphosphate, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Due to the recycling of the by-product uridine diphosphate in the inventive GlcNAcylation methods described herein, lower amounts of uridine monophosphate are required in the solution provided in step A). Thus, in one embodiment, the molar ratio of uridine monophosphate to N-acetyl-D-glucosamine is between 0.0001 and 0.999 more preferably between 0.001 and 0.99, more preferably between 0.005 and 0.95, more preferably between 0.001 and 0.95 and most preferably, between 0.005 and 0.98. In one embodiment, the molar ratio of uridine monophosphate to N-acetyl-D-glucosamine is 0.05. In one embodiment, the molar ratio of uridine monophosphate to N-acetylglucosamine is 0.1. In one embodiment, the molar ratio of uridine monophosphate to N-acetylglucosamine is 0.2. In one embodiment, the molar ratio of uridine monophosphate to N-acetyl-D-glucosamine is 0.5.

Preferably, the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase.
F) isolating the GlcNAcylated saccharide, the GlcNAcylated glycopeptide, the GlcNAcylated glycoprotein, the GlcNAcylated protein, the GlcNAcylated peptide, a GlcNAcylated bioconjugate or the GlcNAcylated small molecule,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, a uridine monophosphate kinase; a 1-domain polyphosphate kinase and/or a 2-domain polyphosphate kinase, and optionally a pyrophosphatase;
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase.

F) isolating the GlcNAcylated saccharide, the GlcNAcylated glycopeptide, the GlcNAcylated glycoprotein, the GlcNAcylated protein, the GlcNAcylated peptide, a GlcNAcylated bioconjugate or the GlcNAcylated small molecule, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:

A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, a uridine monophosphate kinase; a 1-domain polyphosphate kinase and/or a 2-domain polyphosphate kinase, and optionally a pyrophosphatase;

B) producing uridine 5'-diphospho-N-acetyl-α-D-glucosamine from uridine monophosphate and N-acetyl-D-glucosamine in the presence of the set of enzymes, polyphosphate, and adenosine triphosphate, C) isolating the uridine 5'-diphospho-N-acetyl-α-D-glucosamine, D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase.

F) isolating the GlcNAcylated saccharide, the GlcNAcylated glycopeptide, the GlcNAcylated glycoprotein, the GlcNAcylated protein, the GlcNAcylated peptide, a GlcNAcylated bioconjugate or the GlcNAcylated small molecule, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the polyphosphate is a long-chain polyphosphate having at least 25 phosphate residues.

Preferably, the concentration of uridine monophosphate and N-acetyl-D-glucosamine in the solution provided in step A) is in the range of 0.2 mM to 5,000 mM.

Preferably, the concentration of the enzymes in the set of enzymes is between 0.0001 mg/mL and 100 mg/mL based on the total volume of the solution provided in step A).

Preferably, the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:

A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, a uridine monophosphate kinase; and B) producing uridine 5'-diphospho-N-acetyl-α-D-glucosamine from uridine monophosphate and N-acetyl-D-glucosamine in the presence of the set of enzymes, polyphosphate, and adenosine triphosphate, D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase.

wherein the set of enzymes and optionally the N-acetylglucosaminyltransferase are covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, each enzyme of the set of enzymes and the glycosyltransferase are co-immobilized on the reusable, mechanically stable solid support.

Preferably, the method for producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule comprises the following steps:

A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, and a uridine monophosphate kinase; and B) producing uridine 5'-diphospho-N-acetyl-α-D-glucosamine from uridine monophosphate and N-acetyl-D-glucosamine in the presence of the set of enzymes, polyphosphate, and adenosine triphosphate, D) producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetyl-α-D-glucosamine and a saccharide, glycopeptide, glycoprotein, protein, peptide, bioconjugate or small molecule by forming an O-glycosidic bond between uridine 5'-diphospho-N-acetyl-α-D-glucosamine and an available hydroxyl group of the saccharide, glycopeptide, glycoprotein, protein, peptide, bioconjugate or small molecule in the presence of an N-acetylglucosaminyltransferase, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

In one embodiment, GlcNAcylated milk saccharides are produced by the inventive methods described herein. Thus, in one embodiment the inventive method comprises the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated milk saccharide from uridine 5'-diphospho-N-acetyl-α-D-glucosamine and a milk saccharide by forming an O-glycosidic bond between uridine 5'-diphospho-N-acetylglucosamine and an available hydroxyl group of the milk saccharide, in the presence of an N-acetylglucosaminyl-transferase.

wherein the set of enzymes is covalently or adsorptively immobilized on a reusable, mechanically stable solid support.

Preferably, the GlcNAcylated milk saccharide is a human milk oligosaccharide.

Preferably the set of enzymes is covalently or adsorptively immobilized on a reusable, mechanically stable solid support. Preferably, the set of enzymes is covalently co-immobilized on a reusable, mechanically stable solid support thereby increasing or retaining a large fraction of the activity of each enzyme.

Preferably the milk saccharides are selected from the group comprising N-Acetyllactosamine (LacNAc), Lacto-N-triose (LNT II), Lacto-N-neotetraose (LNnT), Lacto-N-tetraose (LNT), Lacto-N-fucopentaose I (LNFP I), Lacto-N-fucopentaose II (LNFP II), Lacto-N-fuconeopentaose III (LNFP III), Lacto-N-fuconeopentaose V (LNFP V), Lacto-N-difucohexaose II (LNDFH II), Lacto-N-hexaose (LNH), Lacto-N-neohexaose (LNnH), fucosyl-lacto-N-neohexaose 1 (F-LNH I), fucosyl-lacto-N-neohexaose II (F-LNH II), difucosyl-lacto-N-hexaose I (DF-LNH I), difucosyl-lacto-N-hexaose II (DF-LNH II), difucosyl-para-lacto-N-neohexaose (DF-para-LNnH), T-trifucosyl-lacto-N-hexaose (TF-LNH), α2,6-sialyllacto-N-neotetraose (LSTc), α2,6-sialyllacto-N-tetraose (LSTa), sialyllacto-N-tetraose b (LSTb), disialyl-lacto-N-hexaose (DS-LNH), fucosyl-α2,6-sialyllacto-N-tetraose (F-LSTa), fucosyl-sialyl-lacto-N-neohexaose I (FS-LNnH I), fucosyl-disialyl-lacto-N-hexaose II (FDS-LNH II) (see FIG. 32).

In one embodiment GlcNAcylated carbohydrate conjugate vaccines are produced by the inventive methods described herein. Thus, in one embodiment the inventive method comprises the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated carbohydrate conjugate vaccine from uridine 5'-diphospho-N-acetyl-α-D-glucosamine and a carbohydrate conjugate vaccine by forming an O-glycosidic bond between uridine 5'-diphospho-N-acetylglucosamine and an available hydroxyl group of the carbohydrate antigen of the conjugate vaccine, in the presence of an N-acetylglucosaminyl-transferase, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme. Preferably, the N-acetylglucosaminyltransferase is also covalently immobilized on the reusable, mechanically stable solid support.

Preferably, the carbohydrate conjugate vaccine is a $CRM_{197}$ conjugate selected from a pneumococcal saccharide, a H. influenzae type B saccharide, and a N. meningitidis serotype A, C, W or Y saccharide; a TT conjugate selected from a pneumococcal saccharide, a H. influenzae type B saccharide, and a N. meningitidis serotype A, C, W or Y saccharide; a DT conjugate selected from a pneumococcal saccharide, a H. influenzae type B saccharide, and a N. meningitidis serotype A, C, W or Y saccharide, a pneumococcal saccharide protein D conjugate, or a H. influenzae type B saccharide OMPC conjugate, wherein the pneumococcal saccharide is preferably selected from serotypes 1, 3, 4, 5, 6A, 6B, 7F, 9V, 14, 18C, 19A, 19F and 23F.

In one embodiment GlcNAcylated antibody drug conjugates are produced by the inventive methods described herein. Thus, in one embodiment the inventive method comprises the following steps:

A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated antibody drug conjugate from uridine 5'-diphospho-N-acetyl-α-D-glucosamine and an antibody drug conjugate by forming an O-glycosidic bond between uridine 5'-diphospho-N-acetylglucosamine and an available hydroxyl group of the antibody drug conjugate, in the presence of an N-acetylglucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme. Preferably, the N-acetylglucosaminyltransferase is also covalently immobilized on the reusable, mechanically stable solid support.

Preferably, the antibody-drug conjugate comprises a monoclonal antibody and a cytotoxic agent.

In one embodiment GlcNAcylated therapeutic proteins are produced by the inventive methods described herein. Thus, in one embodiment the inventive method comprises the following steps:
A) providing a solution comprising
   (i) uridine monophosphate and N-acetyl-D-glucosamine;
   (ii) polyphosphate, and adenosine triphosphate; and
   providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated therapeutic protein from uridine 5'-diphospho-N-acetyl-α-D-glucosamine and a therapeutic protein by forming an O-glycosidic bond between uridine 5'-diphospho-N-acetylglucosamine and an available hydroxyl group of the therapeutic protein, in the presence of an N-acetyl-glucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Preferably, the therapeutic protein is a protein of the immunoglobulin superfamily. Preferably, the protein of the immunoglobulin superfamily and is an antibody. Preferably, the antibody is a monoclonal antibody including bispecific monoclonal antibodies and antibody-based drugs. Preferably, the antibody is not fully GlcNAcylated. Preferably the therapeutic protein is selected from the group consisting of:

3F8, 8H9, Arcitumomab, Ascrinvacumab, Aselizumab, Atezolizumab, Atidortoxumab, Atinuma, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzuma, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, CR6261, Crenezumab, Crizanlizumab, Crotedumab, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlima, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbiviruмab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotama, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Iomab-B, Ipilimumab, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretuzumab, Lupartumab amadotin, Lutikizumab, Mapatumumab, Margetuximab, Marstacima, Maslimomab, Matuzumab, Mavrilimumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, Relatlimab, Remtolumab, Reslizumab, Rilotumumab, Rinucumab, Risankizumab, Rituximab, Rivabazumab pegol, Rmab, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, SGN-CD19A, SHP647, Sibrotuzumab, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tigatuzumab, Tildrakizumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab (=IMAB36, Claudiximab), and Zolimomab aritox.

Preferably, the set of enzymes further comprises a pyrophosphatase. Preferably, the set of enzymes also comprises a 1-domain polyphosphate kinase and/or a 2-domain polyphosphate kinase. Preferably, the set of enzymes further comprises a pyrophosphatase and a 1-domain polyphosphate kinase and/or a 2-domain polyphosphate kinase. Preferably, each enzyme of the set of enzymes and the N-acetylglucosaminyltransferase are co-immobilized on the solid support.

In a preferred embodiment the inventive method comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated antibody from uridine 5'-diphospho-N-acetyl-α-D-glucosamine and an antibody by forming an O-glycosidic bond between uridine 5'-diphospho-N-acetyl-α-D-glucosamine and an available hydroxyl group of the antibody, in the presence of an N-acetylglucosaminyltransferase,
wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

In a preferred embodiment the inventive method comprises the following steps:
A) providing a solution comprising
  (i) uridine monophosphate and N-acetyl-D-glucosamine;
  (ii) polyphosphate, and adenosine triphosphate; and
  providing a set of enzymes comprising a glucose-1-phosphate uridylyltransferase, an N-acetylhexosamine kinase, a polyphosphate kinase, and a uridine monophosphate kinase; and
B) producing uridine 5'-diphospho-N-acetyl-α-D-glucosamine from uridine monophosphate and N-acetyl-D-glucosamine in the presence of the set of enzymes, polyphosphate, and adenosine triphosphate,
D) producing a GlcNAcylated antibody from uridine 5'-diphospho-N-acetyl-α-D-glucosamine and an antibody by forming an O-glycosidic bond between uridine 5'-diphospho-N-acetyl-α-D-glucosamine and an available hydroxyl group of the antibody, in the presence of an N-acetylglucosaminyltransferase.
E) recycling the in-situ formed uridine diphosphate to form uridine triphosphate, wherein the set of enzymes is covalently or adsorptively immobilized on a reusable, mechanically stable solid support.

Preferably, the set of enzymes is covalently co-immobilized on a reusable, mechanically stable solid support thereby increasing or retaining a large fraction of the activity of each enzyme.

Due to the recycling of the by-product uridine diphosphate in the inventive GlcNAcylation methods described herein, lower amounts of UMP are required in the solution provided in step A). Thus, in one embodiment, the molar ratio of UMP to N-acetyl-D-glucosamine is between 0.0001 and 0.999, more preferably between 0.0005 and 0.995, more preferably between 0.001 and 0.995, more preferably between 0.002 and 0.99 and most preferably, between 0.05 and 0.98. In one embodiment, the molar ratio of UMP to N-acetyl-D-glucosamine is 0.05. In one embodiment, the molar ratio of UMP to N-acetyl-D-glucosamine is 0.1. In one embodiment, the molar ratio of UMP to N-acetyl-D-glucosamine is 0.2. In one embodiment, the molar ratio of UMP to N-acetyl-D-glucosamine is 0.5.

In another embodiment, the molar ratio of UMP to N-acetyl-D-glucosamine is between 1 and 10, more preferably between 1.2 and 8, more preferably between 1.5 and 7, more preferably between 1.6 and 6 and most preferably between 2 and 5. In one embodiment, the molar ratio of UMP to N-acetyl-D-glucosamine is 1.5. In one embodiment, the molar ratio of UMP to N-acetyl-D-glucosamine is 2. In one embodiment, the molar ratio of UMP to N-acetyl-D-glucosamine is 5. In one embodiment, the molar ratio of UMP to N-acetyl-D-glucosamine is 10.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Abbreviations and Acronyms

ADP adenosine 5'-diphosphate
AMP adenosine 5'-monophosphate
ATP adenosine 5-triphosphate
dH$_2$O deionized water
NahK N-acetylhexosamine kinase
UDP uridine 5'-diphosphate
UMP uridine 5'-monophosphate
UTP uridine 5-triphosphate
GlcNAc N-acetyl-D-glucosamine
PolyP polyphosphate
PPi pyrophosphate
Pi phosphate
PPK2 polyphosphate kinase 2
PPK3 polyphosphate kinase 3
1 D-PPK2 1-domain polyphosphate kinase 2
2D-PPK2 2-domain polyphosphate kinase 2
GalU glucose 1-phosphate uridylyltransferase
URA6 uridine monophosphate kinase
UPP uracil phosphoribosyltransferase
PmPpA *Pasteurella multocida* inorganic pyrophosphatase Chemicals & Reagents Unless otherwise stated, all chemicals and reagents were acquired from Sigma-Aldrich, and were of the highest purity available. Solid supports were obtained from Resindion, ChiralVision, Röhm GmbH & Co. KG and micromod GmbH.

Example 1: Preparation of Enzymes

Figure 1:
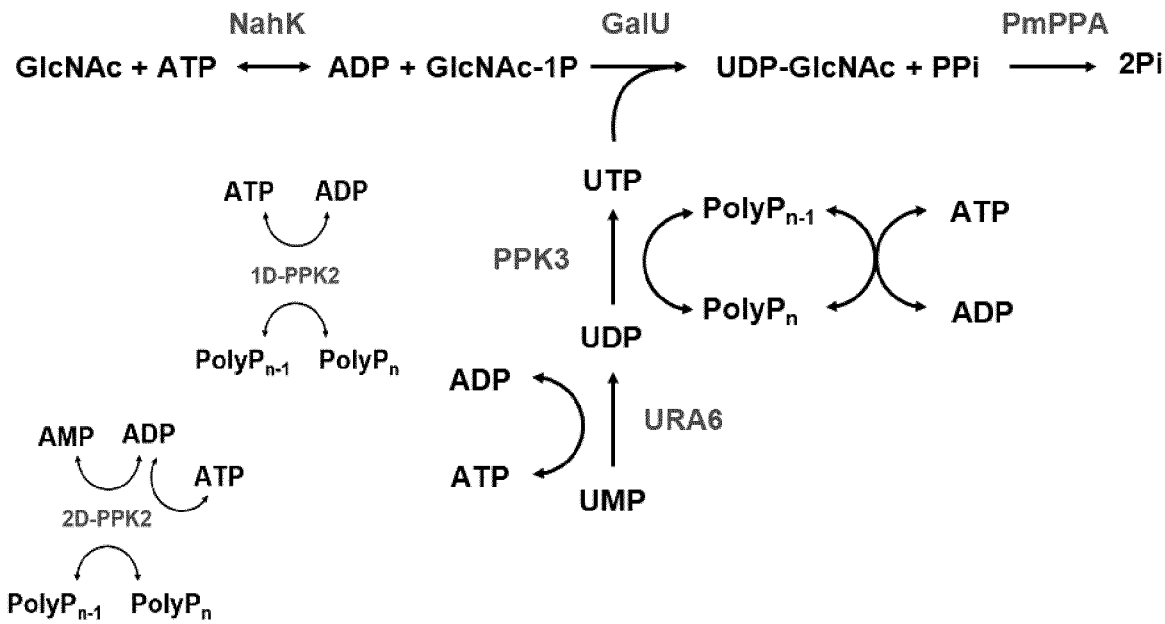
FIG. 1: shows the multi-enzyme cascade through which UDP-N-acetyl-α-D-glucosamine is enzymatically synthesized from low-cost substrates N-acetyl-D-glucosamine, polyphosphate and UMP. The reaction cascade consists of (a) the formation of N-acetylglucosamine-1-phosphate (GlcNAc-1P) from N-acetyl-D-glucosamine and ATP, (b) the formation of uridine triphosphate (UTP) from UMP and polyphosphate, and (c) the reaction of N-acetylglucosamine 1-phosphate with uridine triphosphate to UDP-N-acetyl-α-D-glucosamine. Optionally an inorganic diphosphatase (PmPpa) can added to the reaction cascade in order to hydrolyze pyrophosphate PPi which inhibits the enzyme glucose 1-phosphate uridylyltransferase. The cascade can also be extended by adding a 1 D-PPK2 to assist the conversion of ADP to ATP. Also, the cascade can be extended by adding a 2D-PPK2 in order to activate phosphorylation of AMP to ADP. Moreover, the cascade can be extended by adding a 1 D-PPK2 and a 2DPPK2 in order to inhibit frequent hydrolysis of adenosine phosphates.

The engineered cell-free synthetic metabolic pathway consists of five enzymes (FIG. 1) all produced by *E. coli* BL21 Gold (DE3). Enzymes were chosen according to literature: NahK (EC 2.7.1.162) from *Bifidobacterium longum* to phosphorylate GlcNAc; GalU (EC 2.7.7.9) from *E. coli* K-12 MG1655 as a GlcNAc-1P uridylyltransferase;

URA6 (EC 2.7.4.14) from *Arabidopsis thaliana* for in situ regeneration of UDP from UMP; PPK3 (EC 2.7.4.1) from *Ruegeria pomeroyi* for in situ recovery of energy carriers, ADP and UDP, to their tri-phosphate conjugates; and PmPpA (EC 3.6.1.1) from *Pasteurella multocida* Pm70 for the decomposition of GalU inhibiting pyrophosphate. Details of all enzymes used are given in Table 1 below.

TABLE 1

Enzymes used in this example

| Enzyme | Abbreviation | EC class | Origin | SEQ ID |
|---|---|---|---|---|
| glucose 1-phosphate uridylyltransferase | GalU | 2.7.7.9 | *E. coli* K-12 MG1655 | SEQ ID 4 |
| N-acetylhexosamine 1-kinase | NahK | EC 2.7.1.162 | *Bifidobacterium longum* | SEQ ID 1 |
| Polyphosphate kinase 3 | PPK3 | 2.7.4.1 | *Ruegeria pomeroyi* | SEQ ID 3 |
| Uridine monophosphate kinase | URA6 | 2.7.4.14 | *Arabidopsis thaliana* | SEQ ID 2 |
| Inorganic diphosphatase | PmPpa | 3.6.1.1 | *Pasteurella multocida* Pm70 | SEQ ID 5 |
| 1-domain polyphosphate kinase 2 | 1D-PPK2 | 2.7.4.1 | *Pseudomonas aeruginosa* | SEQ ID 6 |
| 2-domain polyphosphate kinase 2 | 2D-PPK2 | 2.7.4.1 | *Pseudomonas aeruginosa* | SEQ ID 7 |

Transformation, Cultivation, Expression

For all gene expressions *E. coli* BL21 Gold (DE3) was used as a host organism.

Gene Expression

Plasmids and Stock Cultures

Stock solutions of all *E. coli* cultures carrying the plasmids (pET28a with kanamycin resistance) with the gene sequences were available from earlier studies [1,2]. The stock solutions contained 50% glycerol and were kept at −20° C.

The gene and corresponding protein sequences were obtained from the UniProt database: PmPpA (P57918), NahK (E4R3E3), GalU (P0AEP3), PPK3 (Q5LSN8), and URA6 (004905). Gene Designer 2.0 software (Gene Designer, DNA 2.0, Menlo Park, Calif.) was used for optimizing the codon usage of nucleotide sequences for expression in *E. coli*. The resulting sequences were synthesized de novo and cloned by GeneArt™ (Thermo Fisher Scientific, Regensburg, Germany). The following restriction sites for subcloning into vector pET-28a(+) were used: NcoI and XhoI for GalU, NahK and PmPpA (enzymes carrying a C-terminal hexahistidin-tag (His-tag)), NdeI and XhoI with PPK3 and URA6 (for an N-terminal His-tag). After transformation of the plasmids into *E. coli*, the DNA was isolated and the accuracy of the constructs was checked by gene sequencing (Eurofins Genomics, Ebersberg, Germany).

Enzyme Expression

For heterologous gene expression, aliquots were removed from the stock solutions and spread on LB agar plates containing the according antibiotic. The plates were cultivated overnight at 37° C. Single cultures were used to inoculate precultures (containing 50 μg/mL kanamycin) in shaker flasks with baffles. Cultures were typically grown to an $OD_{600}$ of about 4.2. Main expression cultures containing 50 μg/mL kanamycin were typically inoculated with 1% preculture and cultivated at 37° C. to an $OD_{600}$ of around 0.6-0.8. The temperature was then changed to 16-20° C. and the expression was induced with typically 0.4 mM IPTG. After, typically, 20 h, the culture were harvest typically by 6000×g for 30 min at 4° C. Media used were TB media except for GalU (LB media) (see table 2).

TABLE 2

Media used in this Example

| Media | Content |
|---|---|
| Luria-Bertani (LB) | 10 g tryptone<br>5 g yeast extract<br>5 g NaCl<br>in 1 L $dH_2O$ |
| Terrific broth (TB) | 24 g yeast extract<br>12 g tryptone<br>5 g glycerol<br>89 mM Phosphate buffer (added after autoclaving)<br>in 1 L $dH_2O$ |

Enzyme Purification

The plasmids pET28a and pET100/D-TOPO harbor a N-terminal His6-tag and the enzyme are, thus, purified with Ion metal affinity chromatography using the ÄKTAstart system and HisTrap High-Performance or Fast-Flow columns (1 mL column volume) from GE Healthcare. For the purification of enzymes the cells were lysed by sonication in lysis buffer (50 mM HEPES (pH 7.5), 10 mM $Mg^{2+}$, 300 mM NaCl, 10 mM imidazole and 5% glycerol).

Imidazole (500 mM) was used as eluent in isocratic elutions (50 mM HEPES (pH 7.5), 10 mM $Mg^{2+}$, 300 mM NaCl, 500 mM imidazole and 5% glycerol). Standard conditions as recommended by the manufactures were used. After purification the enzyme concentrations were tested by BCA assays and evaluated by SDS-gels.

Example 2: Heterogeneous Preparation of UDP-N-Acetyl-α-D-Glucosamine

Measurements

High-performance anion exchange chromatography (HPAEC) with UV (260 nm) and pulsed amperometric detection (PAD) was utilized to measure concentrations of reactants. For analyte separation and quantification a step gradient elution method was developed and validated chromatographic separation was performed at a system flow of 0.5 mL/min using a non-porous pellicular column CarboPac PA1 (250×2 mm). The HPAEC system (ICS5000) as well as all columns, components and software were purchased from Thermo Scientific (Waltham, USA).

Experiment A

A wide range of commercially available solid supports (see Table 3) were tested for the co-immobilization of the enzymes used in the inventive UDP-N-acetyl-α-D-glucosamine synthesis (see FIG. 1) and their effect on the synthesis of UDP-N-acetyl-α-D-glucosamine was evaluated.

TABLE 3

Table of solid supports tested in Experiment A

| Solid support | Mass (mg) | Matrix | Pore diameter (nm) | Particle size (μm) | Functional group |
|---|---|---|---|---|---|
| EC-EP | 120 | polymethacrylate | 10-20 | 200-500 | epoxy |
| EP403/M | 90 | polymethacrylate | 40-60 | 200-500 | epoxy |
| IB-COV1 | 93 | polyacrylic | | 150-300 | butyl, epoxy |
| IB-COV2 | 92 | polyacrylic | | 150-300 | epoxy |
| IB-COV3 | 98 | polyacrylic | | 300-700 | epoxy |
| Eupergit ® CM | 102 | acrylic | | 50-300 | epoxy |
| ECR8215F | 92 | methacrylate | 120-180 | 150-300 | epoxy |
| ECR8204F | 94 | methacrylate | 30-60 | 150-300 | epoxy |
| ECR8209F | 98 | methacrylate | 60-120 | 150-300 | epoxy |
| ECR8285 | 90 | methacrylate | 40-60 | 250-1000 | butyl, epoxy |
| EC-HFA | 120 | | | | |
| HFA403/M | 121 | | | | |
| ECR8806F | 112 | methacrylate | 50-70 | 150-300 | octadecyl |
| ECR1091M | 101 | Macroporous divinylbenzene | 95-120 | 300-710 | — |
| ECR1030F | 108 | DVB/methacrylic polymer | 22-34 | 150-300 | — |
| ECR1504 | 104 | styrene | | 300-1200 | tert. amine |
| ECR1604 | 108 | styrene | | 300-1200 | quart. amine |

To test the multi-enzyme cascade on various enzyme loaded beads, a given mass (see Table 3) of each resin was added to a 2 mL low-binding tube. After approx. 2 h of incubation with lysis buffer (see Table 4), the supernatant was removed [equilibration step]. Afterwards, 0.5 mL of cell lysate were added to each tube and incubated overnight (approx. 12 h) at 4° C. After incubation, beads were washed (3 times) and blocking buffer (2 M glycine) was added. Beads were incubated for 24 h at room temperature with the blocking buffer. Afterwards, the blocking buffer was removed and beads were washed with lysis buffer three times.

TABLE 4

Buffers used for the immobilization of biocatalysts in Experiment A

| Conc. in mM/% | Buffers Immobilization/Lysis | Blocking Buffer |
|---|---|---|
| HEPES | 200 | 125 |
| MgCl$_2$ | 50 | 25 |
| NaCl | 300 | 150 |
| Glycerol | 5% | 3% |
| Glycine | | 3000 |

Figure 4:
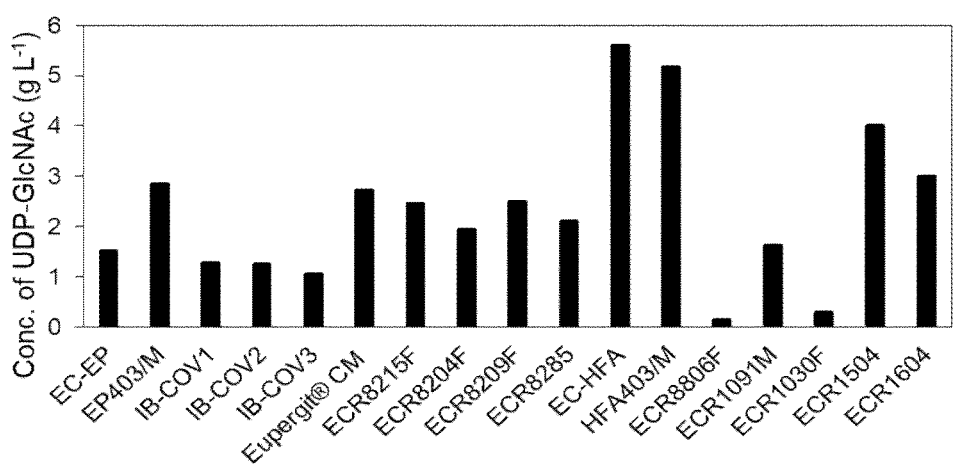
FIG. 4 shows results of the solid support screening of the UDP-GlcNAc synthesis in a first cycle. Productivities were measured by HPAEC-UV.

200 μL of the feed solution (see Table 5) containing substrates was transferred to each tube containing the beads. The reactions were carried out for around 17 h at 30° C. and under shaking (600 rpm). The UDP-N-acetyl-α-D-glucosamine concentrations were then measured by HPAEC-UV/PAD. The results are shown in FIG. 4.

TABLE 5

Concentration of reactants in the feed solution of Experiment A

| Substrate | Conc. (mM) |
|---|---|
| UMP | 11 |
| ATP | 17 |

TABLE 5-continued

Concentration of reactants in the feed solution of Experiment A

| Substrate | Conc. (mM) |
|---|---|
| GlcNac | 12 |
| PolyP$_{25}$ | 14 |
| HEPES | 80 |
| MgCl$_2$ | 60 |

Figure 5:
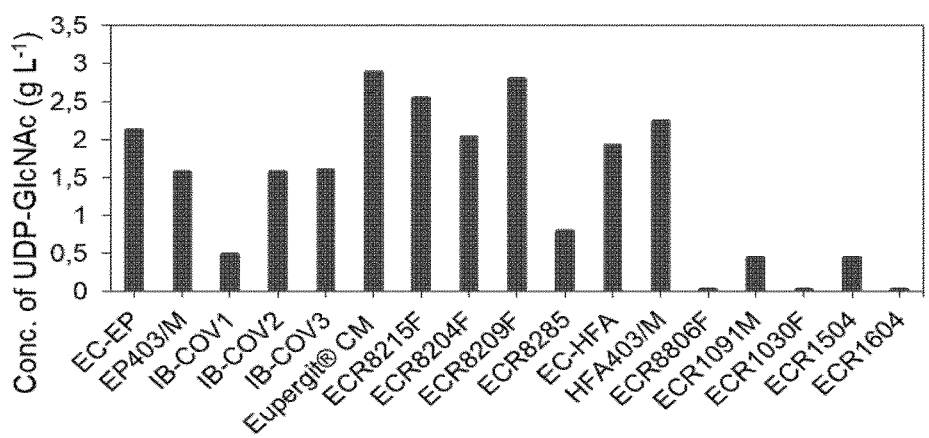
FIG. 5 shows results of the solid support screening of the UDP-GlcNAc synthesis in a second cycle. Productivities were measured by HPAEC-UV.
Figure 6:
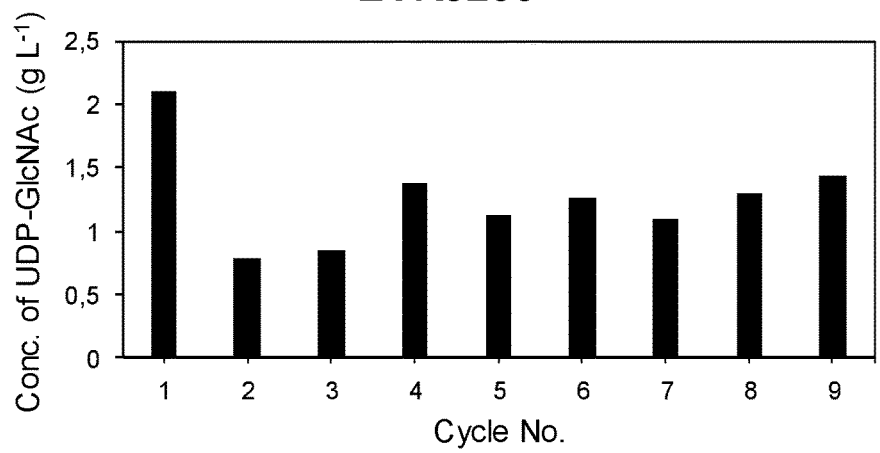
FIG. 6 shows results of the UDP-GlcNAc synthesis with co-immobilized enzymes on ECR8285 resin—a methacrylate resin functionalized with both butyl and epoxy groups—in nine cycles. Productivities were measured by HPAEC-UV.
Figure 7:
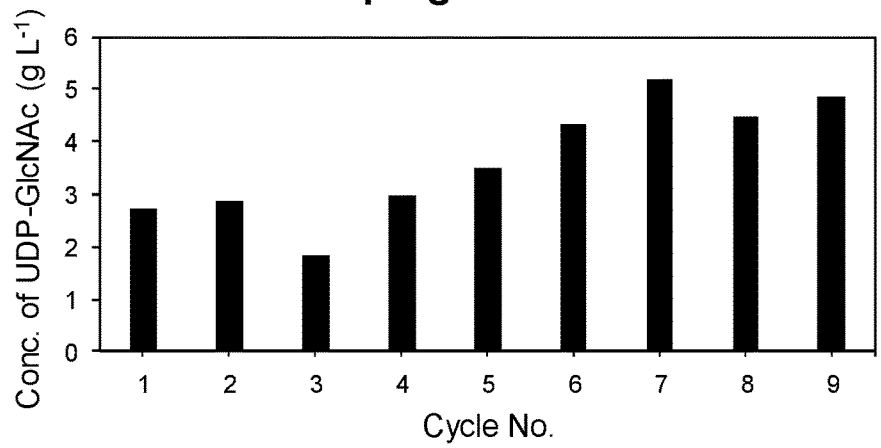
FIG. 7 shows results of the UDP-GlcNAc synthesis with co-immobilized enzymes on Eupergit CM resin—a methacrylate/acrylamide resin functionalized with epoxy groups—in nine cycles. Productivities were measured by HPAEC-UV.
Figure 8:
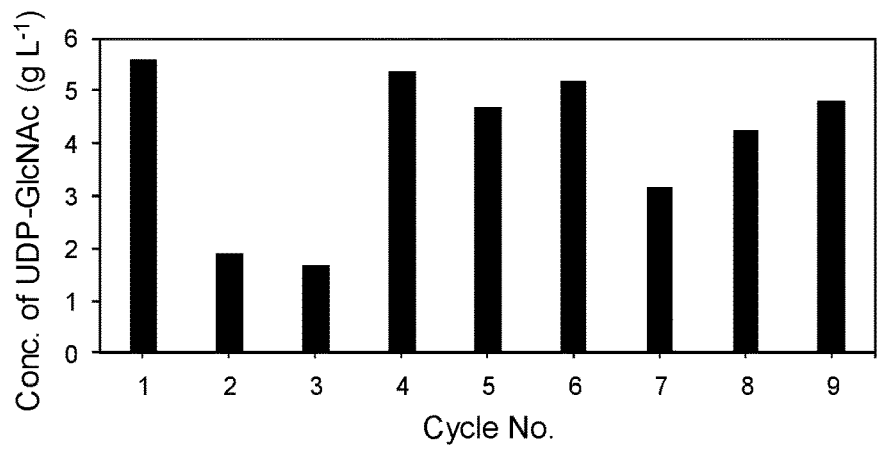
FIG. 8 shows results of the UDP-GlcNAc synthesis with co-immobilized enzymes on EC-HFA resin—a methacrylate resin functionalized with amino epoxy groups—in nine cycles. Productivities were measured by HPAEC-UV.
Figure 9:
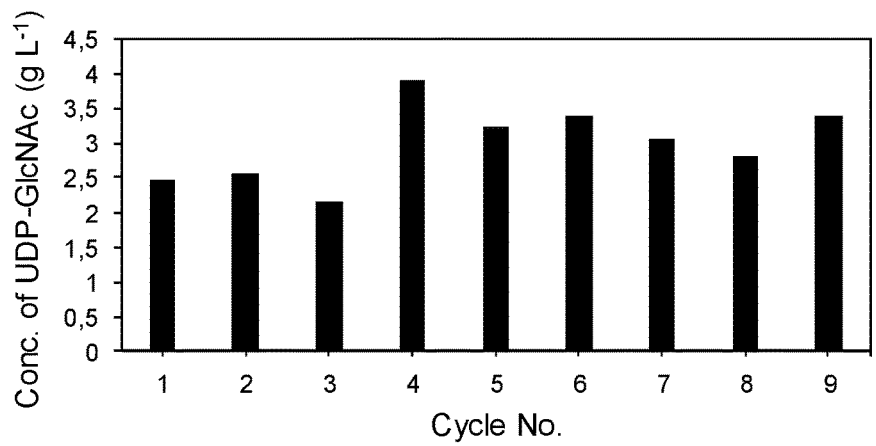
FIG. 9 shows results of the UDP-GlcNAc synthesis with co-immobilized enzymes on ECR8215F resin—a methacrylate resin functionalized with epoxy groups—in nine cycles. Productivities were measured by HPAEC-UV.
Figure 10:
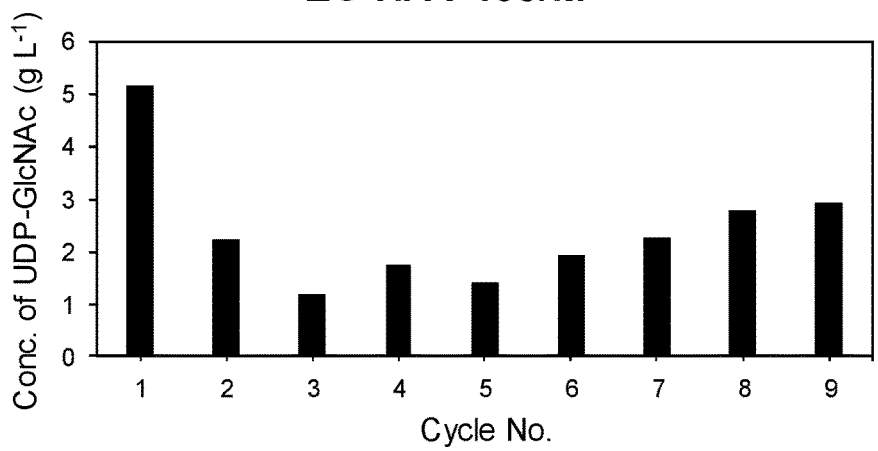
FIG. 10 shows results of the UDP-GlcNAc synthesis with co-immobilized enzymes on EC-HFA 403/M resin—a methacrylate resin functionalized with amino epoxy groups—in nine cycles. Productivities were measured by HPAEC-UV.
Figure 11:
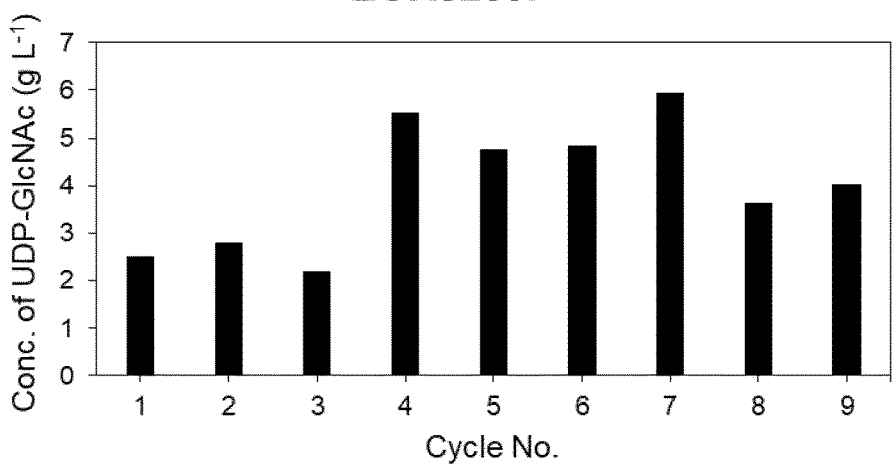
FIG. 11 shows results of the UDP-GlcNAc synthesis with co-immobilized enzymes on ECR8209F resin—a methacrylate resin functionalized with epoxy groups—in nine cycles. Productivities were measured by HPAEC-UV.

In order to evaluate the re-usability of the beads—after the first cycle-supernatant were removed and the beads were washed with Lysis buffer once. Afterwards, 200 μL of feed solution was added to the beads. The reactions were carried out for around 10 h at 30° C. and under shaking (600 rpm). The results are depicted in FIG. 5. It is shown that enzymes co-immobilized on several commercially available beads are useful for re-usability and provide mechanically robust beads with co-immobilized enzymes.

After the second cycle, certain beads were selected to evaluate their further re-usability. The results are shown in FIG. 6 to FIG. 11.

Experiment B

Enzyme Immobilization

Immobilized enzymes can often be separated from solutions and reused. Moreover, they may exhibit higher activity and can be used for a wide range of processes, such as continuous synthesis in packed bed reactors. A wide range of commercially available solid supports were tested for the co-immobilization of the UDP-GlcNAc multi-enzyme cascade.

TABLE 6

Table of solid supports tested in Experiment B (epoxy)

| Solid Support | Matrix | Pore diameter (nm) | Particle size (μm) | Oxiran content (μm/g wet) | Bonding type | Functional group |
|---|---|---|---|---|---|---|
| SEPABEADS EC-EP/M | Polymethacrylate | 10-20 | 200-500 | 144 | covalent | epoxy |
| RELIZYME EP403/M | Polymethacrylate | 40-60 | 200-500 | 56 | covalent | epoxy |
| SEPABEADS EC-HFA/M | Polymethacrylate | 10-20 | 200-500 | 77 | covalent | amino-epoxy |
| RELIZYME HFA403/M | Polymethacrylate | 40-60 | 200-500 | 30 | covalent | amino-epoxy |
| RELIZYME HFA403/S | Polymethacrylate | 40-60 | 100-300 | 59 | covalent | amino-epoxy |
| SEPABEADS EC-HFA/S | Polymethacrylate | 10-20 | 100-300 | 91 | covalent | amino-epoxy |
| RELIZYME EP403/S | Polymethacrylate | 40-60 | 100-300 | 66 | covalent | epoxy |
| RELISORB EP400/SS | Polymethacrylate | 80-100 | 50-150 | Min. 100 μm/g dry | covalent | epoxy |
| Eupergit ® CM | acrylic | | 50-300 | 0.75 | covalent | epoxy |
| Lifetech ™ ECR8215F | methacrylate | 120-180 | 150-300 | | covalent | epoxy |
| Lifetech ™ ECR8204F | methacrylate | 30-60 | 150-300 | | covalent | epoxy |
| Lifetech ™ ECR8209F | methacrylate | 60-120 | 150-300 | | covalent | epoxy |
| Lifetech ™ ECR8285 | methacrylate | 40-60 | 250-1000 | | covalent | butyl, epoxy |
| Lifetech ™ ECR8206F | methacrylate | 50-60 | 150-300 | | covalent | epoxy |
| Lifetech ™ ECR8215M | methacrylate | 120-180 | 300-710 | | covalent | epoxy |
| Lifetech ™ ECR8204M | methacrylate | 30-60 | 300-710 | | covalent | epoxy |
| Lifetech ™ ECR8209M | methacrylate | 60-120 | 300-710 | | covalent | epoxy |
| Lifetech ™ ECR8206M | methacrylate | 50-60 | 300-710 | | covalent | epoxy |
| Imm150P | Copolym. Of methacrylate | | 150-500 | | | |
| IB-COV1 | polyacrylic | | 150-300 | | covalent | butyl, epoxy |
| IB-COV2 | polyacrylic | | 150-300 | | covalent | epoxide |
| IB-COV3 | polyacrylic | | 300-700 | | covalent | epoxide |

TABLE 7

Table of solid supports tested in Experiment B (other)

| Solid Support | Matrix | Pore diameter (nm) | Particle size (μm) | Bonding type | Functional group |
|---|---|---|---|---|---|
| Lifetech ™ ECR8305F | methacrylate | 30-60 | 150-300 | covalent or ionic | Amino C2 |
| Lifetech ™ ECR8309F | methacrylate | 60-120 | 150-300 | covalent or ionic | Amino C2 |
| Lifetech ™ ECR8315F | methacrylate | 120-180 | 150-300 | covalent or ionic | Amino C2 |
| Lifetech ™ ECR8415F | methacrylate | 120-180 | 150-300 | covalent or ionic | Amino C6 |
| Lifetech ™ ECR8409F | methacrylate | 60-120 | 150-300 | covalent or ionic | Amino C6 |
| Lifetech ™ ECR8404F | methacrylate | 30-60 | 150-300 | covalent or ionic | Amino C6 |
| Lifetech ™ ECR8305M | methacrylate | 30-60 | 300-710 | covalent or ionic | Amino C2 |
| Lifetech ™ ECR8309M | methacrylate | 60-120 | 300-710 | covalent or ionic | Amino C2 |
| Lifetech ™ ECR8315M | methacrylate | 120-180 | 300-710 | covalent or ionic | Amino C2 |
| Lifetech ™ ECR8415M | methacrylate | 120-180 | 300-710 | covalent or ionic | Amino C6 |

TABLE 7-continued

Table of solid supports tested in Experiment B (other)

| Solid Support | Matrix | Pore diameter (nm) | Particle size (μm) | Bonding type | Functional group |
|---|---|---|---|---|---|
| Lifetech™ ECR8409M | methacrylate | 60-120 | 300-710 | covalent or ionic | Amino C6 |
| Lifetech™ ECR8404M | methacrylate | 30-60 | 300-710 | covalent or ionic | Amino C6 |
| Lifetech™ ECR8305M | methacrylate | 30-60 | 300-710 | covalent or ionic | Amino C2 |
| Lifetech™ ECR8305 | methacrylate | 30-60 | 150-710 | covalent or ionic | Amino C2 |
| Lifetech™ ECR8309 | methacrylate | 60-120 | 150-710 | covalent or ionic | Amino C2 |
| Lifetech™ ECR8315 | methacrylate | 120-180 | 150-710 | covalent or ionic | Amino C2 |
| Lifetech™ ECR8415 | methacrylate | 120-180 | 150-710 | covalent or ionic | Amino C6 |
| Lifetech™ ECR8409 | methacrylate | 60-120 | 150-710 | covalent or ionic | Amino C6 |
| Lifetech™ ECR8404 | methacrylate | 30-60 | 150-710 | covalent or ionic | Amino C6 |
| Lifetech™ ECR8305 | methacrylate | 30-60 | 150-710 | covalent or ionic | Amino C2 |
| SEPABEADS EC-EA/M | Polymethacrylate | 10-20 | 200-500 | covalent or ionic | ethylamino |
| SEPABEADS EC-EA/S | Polymethacrylate | 10-20 | 100-300 | covalent or ionic | ethylamino |
| RELIZYME EA403/S | Polymethacrylate | 40-60 | 100-300 | covalent or ionic | ethylamino |
| RELIZYME EA403/M | Polymethacrylate | 40-60 | 200-500 | covalent or ionic | ethylamino |
| SEPABEADS EC-HA/S | Polymethacrylate | 10-20 | 100-300 | covalent or ionic | hexylamino |
| RELIZYME HA403/S | Polymethacrylate | 40-60 | 100-300 | covalent or ionic | hexylamino |
| SEPABEADS EC-HA/M | Polymethacrylate | 10-20 | 200-500 | covalent or ionic | hexylamino |
| RELIZYME HA403/M | Polymethacrylate | 40-60 | 200-500 | covalent or ionic | hexylamino |
| Lifetech™ ECR8806M | methacrylate | 50-70 | 300-710 | adsorption | octadecyl |
| Lifetech™ ECR8804M | methacrylate | 35-45 | 300-710 | adsorption | octadecyl |
| Lifetech™ ECR8806F | methacrylate | 50-70 | 150-300 | adsorption | octadecyl |
| Lifetech™ ECR8804F | methacrylate | 35-45 | 150-300 | adsorption | octadecyl |
| Lifetech™ ECR8806 | methacrylate | 50-70 | 150-710 | adsorption | octadecyl |
| Lifetech™ ECR8804 | methacrylate | 35-45 | 150-710 | adsorption | octadecyl |
| IB-ADS-1 | Polyacrylic | 71% pore volume | 300-700 | adsorption | Alkyl |
| IB-ADS-2 | Styrene | 75% pore volume | 150-300 | adsorption | Phenyl |
| IB-ADS-3 | Methacrylate | 58% pore volume | 150-300 | adsorption | Octadecyl |
| IB-ADS-4 | Styrene | 58% pore volume | 300-700 | adsorption | Styrene, methyl |
| SEPABEADS EC-BU | Polymethacrylate | 10-20 | 200-500 | adsorption | butyl |
| RELIZYME BU403 | Polymethacrylate | 40-60 | 100-300 | adsorption | butyl |
| SEPABEADS EC-OC | Polymethacrylate | 10-20 | 200-500 | adsorption | Octyl |
| RELIZYME OC403 | Polymethacrylate | 40-60 | 100-300 | adsorption | octyl |
| SEPABEADS EC-OD | Polymethacrylate | 10-20 | 200-500 | adsorption | Octadecyl |
| RELIZYME OD403 | Polymethacrylate | 40-60 | 100-300 | adsorption | octadecyl |
| Lifetech™ ECR1090M | Macroporous divinylbenzene | 90-110 | 300-710 | adsorption | — |
| Lifetech™ ECR1091M | Macroporous divinylbenzene | 95-120 | 300-710 | adsorption | — |
| Lifetech™ ECR1090F | Macroporous divinylbenzene | 90-110 | 150-300 | adsorption | — |

TABLE 7-continued

Table of solid supports tested in Experiment B (other)

| Solid Support | Matrix | Pore diameter (nm) | Particle size (μm) | Bonding type | Functional group |
|---|---|---|---|---|---|
| Lifetech™ ECR1091F | Macroporous divinylbenzene | 95-120 | 150-300 | adsorption | — |
| Lifetech™ ECR1090 | Macroporous divinylbenzene | 90-110 | 150-710 | adsorption | — |
| Lifetech™ ECR1091 | Macroporous divinylbenzene | 95-120 | 150-710 | adsorption | — |
| Lifetech™ ECR1030F | DVB/methacrylic polymer | 22-34 | 150-300 | adsorption | — |
| Lifetech™ ECR1030M | DVB/methacrylic polymer | 20-30 | 150-300 | adsorption | — |
| Lifetech™ ECR1061M | DVB/methacrylic polymer | 60-75 | 150-300 | adsorption | — |
| Lifetech™ ECR1030M | DVB/methacrylic polymer | 20-30 | 150-710 | adsorption | — |
| Lifetech™ ECR1061M | DVB/methacrylic polymer | 60-75 | 150-710 | adsorption | — |
| Lifetech™ ECR1504 | styrene | | 300-1200 | ionic | tert. amine |
| Lifetech™ ECR1508 | styrene | | 300-1200 | ionic | tert. amine |
| Lifetech™ ECR1604 | styrene | | 300-1200 | ionic | quat. amine |
| Lifetech™ ECR1640 | styrene | | 300-1200 | ionic | quat. amine |
| IB-CAT-1 | styrene | 54% pore volume | 300-700 | cationic, strong | Sulphonic |
| IB-ANI-1 | polyacrylic | 78% pore volume | 150-300 | anionic | primary amine |
| IB-ANI-2 | polystyrene | 55% pore volume | 630 | anionic, weak | tertiary amine |
| IB-ANI-3 | polystyrene | 72% pore volume | 800 | anionic, weak | quat. Ammon. |
| IB-ANI-4 | polystyrene | 62% pore volume | 690 | anionic, strong | quat. Ammon. |
| SEPABEADS EC-HG/S | Polymethacrylate | 10-20 | 100-300 | | 1,2-diol |
| RELIZYME HG403/S | Polymethacrylate | 40-60 | 100-300 | | 1,2-diol |
| SEPABEADS EC-HG/M | Polymethacrylate | 10-20 | 200-500 | | 1,2-diol |
| RELIZYME HG403/M | Polymethacrylate | 40-60 | 200-500 | | 1,2-diol |

The solid supports are here divided into three groups depending on their immobilization mechanism: a) epoxy (including amino-epoxy) supports, b) ionic & adsorption supports and c) glutaraldehyde activated supports. In addition, three different solid support to protein ratios were tested for each solid support to find the optimal ratios: series 1, series 2 and series 3 (see Table 8-Table 11).

TABLE 8

Tested protein stock solution to solid support ratio

| Series | 1 | 2 | 3 |
|---|---|---|---|
| Protein stock solution to solid support ratio (mass) | 1:12 | 1:35 | 1:45 |
| Volume | 500 μL | 500 μL | 700 μL |

TABLE 9

Selection of tested epoxy (including amino-epoxy) supports

| | Mass (mg) | | |
|---|---|---|---|
| Resin | Series 1 | Series 2 | Series 3 |
| EC-EP | 104 | 268 | 478 |
| EP403/M | 107 | 267 | 484 |
| IB-COV1 | 102 | 256 | 442 |
| IB-COV2 | 110 | 271 | 440 |
| IB-COV3 | 123 | 247 | 438 |
| Eupergit® CM | 81 | 156 | 269 |
| ECR8215F | 97 | 251 | 466 |
| ECR8204F | 96 | 246 | 468 |
| ECR8209F | 104 | 285 | 450 |
| ECR8285 | 102 | 253 | 450 |
| EP403/S | 102 | 248 | 449 |
| EP400/SS | 93 | 248 | 453 |
| EC-HFA/M | 101 | 275 | 460 |
| HFA403/M | 100 | 253 | 465 |
| HFA403/S | 92 | 259 | 470 |
| EC-HFA/S | 117 | 286 | 504 |
| Imm150P | 105 | 266 | 425 |

TABLE 10

Selection of tested ionic & adsorption supports

| | Mass (mg) | | |
|---|---|---|---|
| Resin | Series 1 | Series 2 | Series 3 |
| 8409F | 96 | 253 | 422 |
| 8315F | 93 | 264 | 470 |
| 8309F | 106 | 268 | 443 |
| 1030F | 92 | 244 | 481 |
| 1509 | 108 | 245 | 438 |
| 8806F | 103 | 266 | 434 |
| 8415F | 92 | 252 | 443 |
| 1091M | 95 | 259 | 475 |
| 1604 | 102 | 273 | 465 |
| EC-EA/M | 95 | 239 | 429 |
| EC-HA | 99 | 272 | 438 |
| EA403/S | 101 | 251 | 478 |
| ADS-1 | 111 | 263 | 471 |
| ADS-2 | 106 | 253 | 503 |
| ADS-3 | 108 | 265 | 457 |
| ADS-4 | 99 | 246 | 499 |
| CAT-1 | 106 | 243 | 445 |
| ANI-1 | 97 | 276 | 444 |
| ANI-2 | 122 | 303 | 466 |
| ANI-3 | 106 | 253 | 460 |
| ANI-4 | 117 | 256 | 453 |

TABLE 11

Selection of tested glutaraldehyde activated supports

| | Mass (mg) | | |
|---|---|---|---|
| Resin | Series 1 | Series 2 | Series 3 |
| 8409F | 95 | 252 | 434 |
| 8315F | 102 | 247 | 469 |
| 8309F | 96 | 247 | 492 |
| 8415F | 97 | 248 | 474 |
| EC-EA/M | 113 | 253 | 476 |
| EC-HA | 99 | 250 | 436 |
| EA403/S | 104 | 242 | 461 |

The following protocol was followed for the experiment: Biomass containing the overexpressed enzymes were mixed together [see table 13, step 1] and centrifuged 6000×g for 30 min at 4° C. [step 2]. The cell pellets were resuspended in immobilization/lysis buffer to a volume of 150 mL (see table 12) [step 3]. Cells were lysed by sonication [step 4]. After sonication the slurry was centrifuged 12 000×g for 45 min at 4° C. [step 5] to remove cell debris, followed by filtration through 1.2 μm and 0.8 μm filters. After centrifugation, the supernatant was removed and kept on ice. The total protein concentration of the supernatant (protein stock solution) was 14.5 (+/−0.5) mg/mL. A given mass of each immobilizer was added to a 2 mL low-binding tube. Amino-functionalized supports were activated with glutaraldehyde by incubation in activation buffer for 1 hour to generate glutaraldehyde activated supports (group c)). The solid supports were washed two times with washing buffer A (for epoxy supports and glutaraldehyde supports) and washing buffer B (for ionic & adsorption supports) and equilibrated for 1 hour with immobilization/lysis buffer. Afterwards, cell lysate was added to each tube and incubated overnight (~36 h) at 4° C. [step 6]. The supports with the immobilized enzymes were washed (3 times) with washing buffer [step 7]. In addition the epoxy supports were incubated with blocking buffer (2 M glycine) for 24 h [step 8]. Afterwards, the blocking buffer was discarded and the supports were washed with washing buffer A three times.

TABLE 12

Buffers used for the immobilization of biocatalysts.

| Conc in mM/% | Buffers Immobilization/Lysis | Washing Buffer A | Washing Buffer B | Blocking Buffer | Activation buffer |
|---|---|---|---|---|---|
| HEPES | 250 | 400 | 125 | 125 | 250 |
| MgCl$_2$ | 50 | 50 | 25 | 25 | 50 |
| NaCl | 300 | 600 | 150 | 150 | 300 |
| Glycerol | 5% | 5% | 3% | 3% | 5% |
| Glycine | | | | 3000 | |
| Glutaraldehyde | | | | | 2.5% |

TABLE 13

Composition of the biomass mixtures used in step 1.

| Enzyme | Biomass (gr) |
|---|---|
| NahK | 10.52 |
| GalU | 5.17 |
| URA6 | 6.25 |
| PPK3 | 7.44 |
| PmPpa | 3.54 |
| 1d-PPK2 | 1.48 |
| 2d-PPK2 | 2.67 |

Figure 12A:
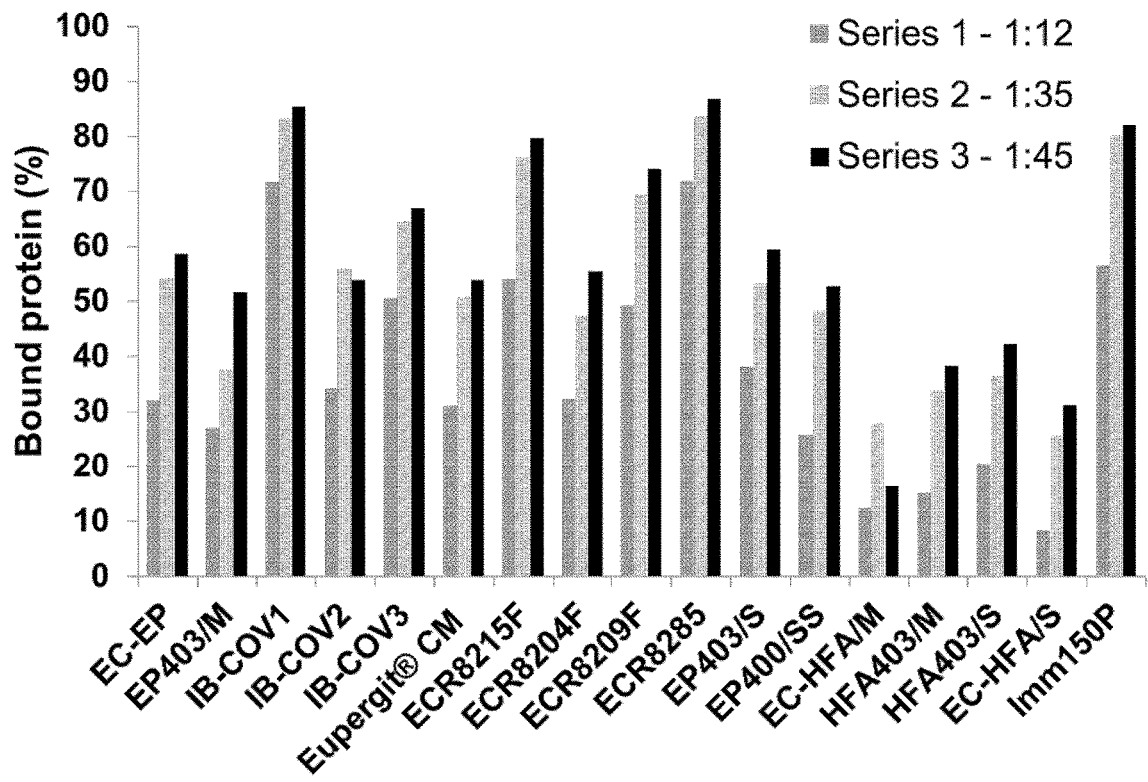
FIG. 12 shows A) a diagram of the amount of protein bound to epoxy solid support determined by quantifying the protein in the supernatant after immobilization of several solid supports. Standard BCA protein quantification protocols were followed; B) a diagram of the amount of protein bound to ionic and adsorption solid support determined by quantifying the protein in the supernatant after immobilization of several solid supports. Standard BCA protein quantification protocols were followed; and C) a diagram of the amount of protein bound to glutaraldehyde activated solid support determined by quantifying the protein in the supernatant after immobilization of several solid supports. Standard BCA protein quantification protocols were followed.
Figure 12B:
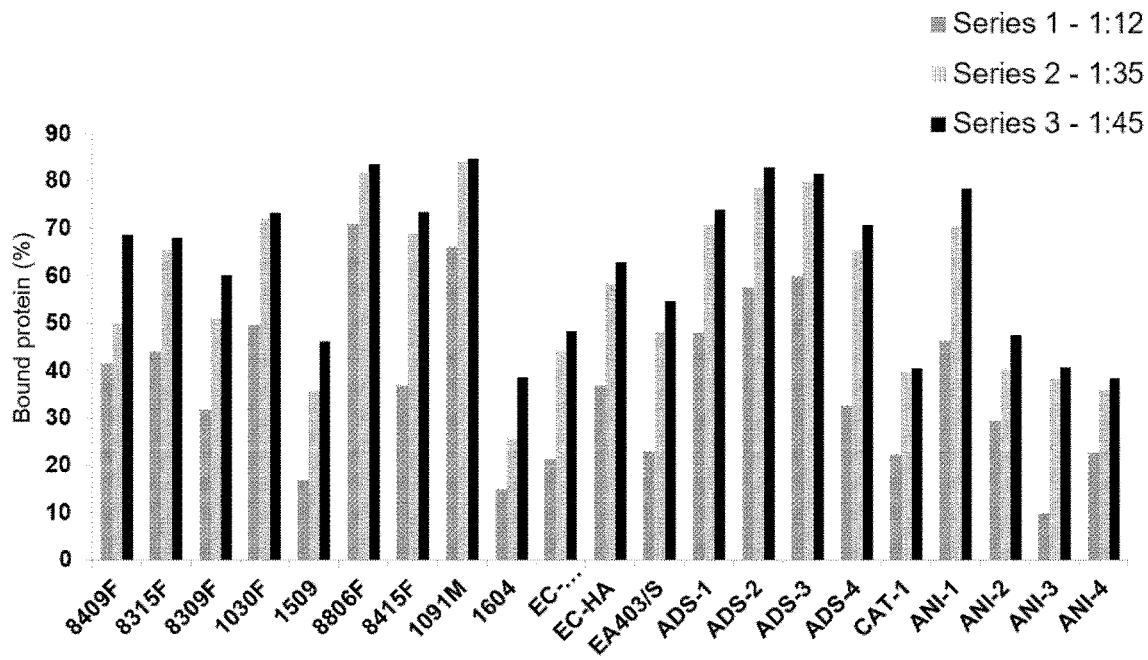
Figure 12C:
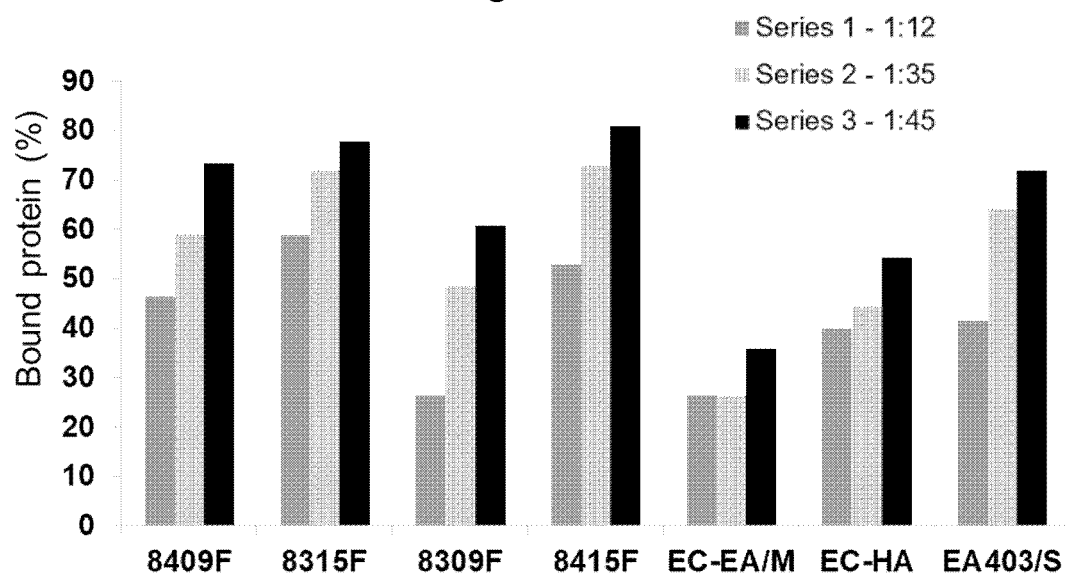

The amount of protein bound to solid support was determined by quantifying the protein in the supernatant after immobilization. Standard BCA protein quantification protocols were followed. The results for several resins (see Tables 9-11) are shown in FIGS. 12A-12C.

Reactions

Figure 13A:
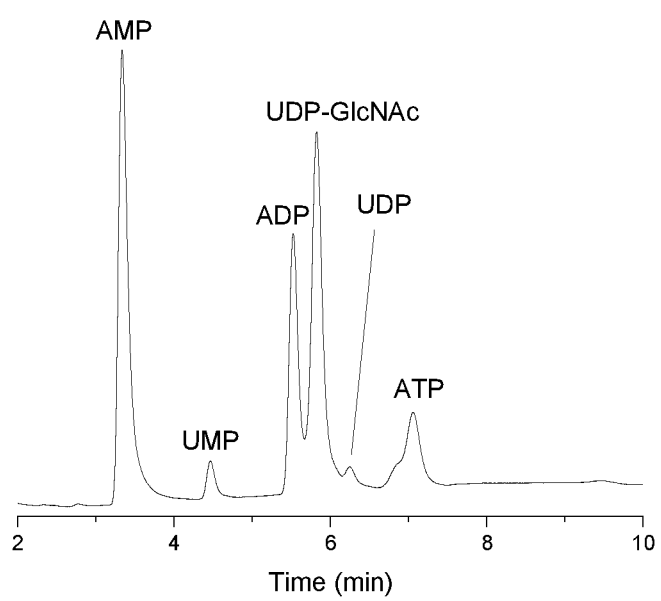
FIG. 13 shows A) HPAEC-UV chromatogram of the quantification of UDP-GlcNAc (and other reactants). The chromatogram shown is from a reaction catalyzed by the enzyme cascade immobilized on Eupergit CM; B) HPAEC-UV chromatograms of the quantification of UDP-GlcNAc (and other reactants). The chromatogram shown is from a reaction catalyzed by the enzyme cascade immobilized on IB-ADS1, IB-CAT, ECR1504, IB-ANI1; C) HPAEC-UV chromatogram of the quantification of UDP-GlcNAc (and other reactants). The chromatogram shown is from a reaction catalyzed by the enzyme cascade immobilized on ECR8315F active by glutaraldehyde.
Figure 13B:
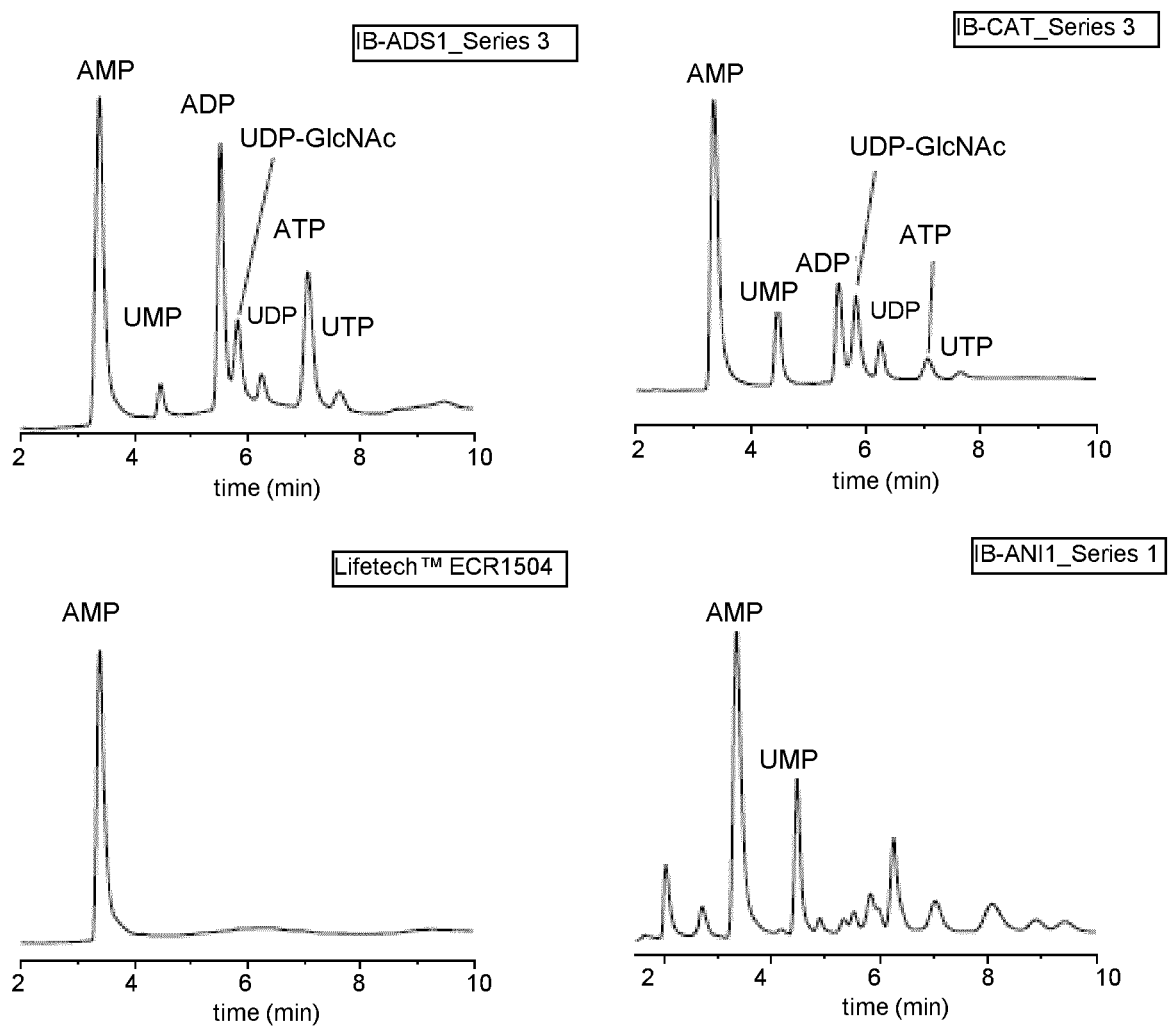
Figure 13C:
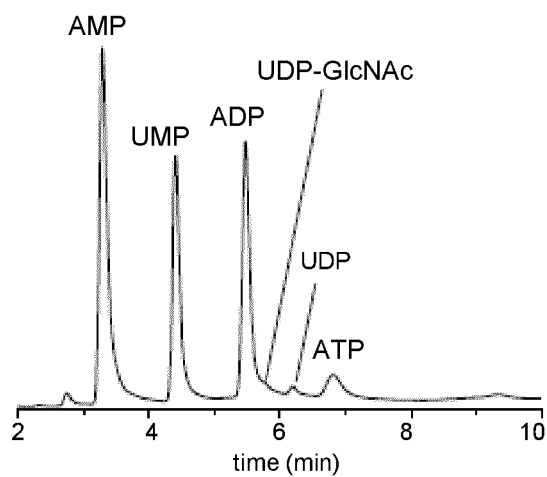
Figure 14:
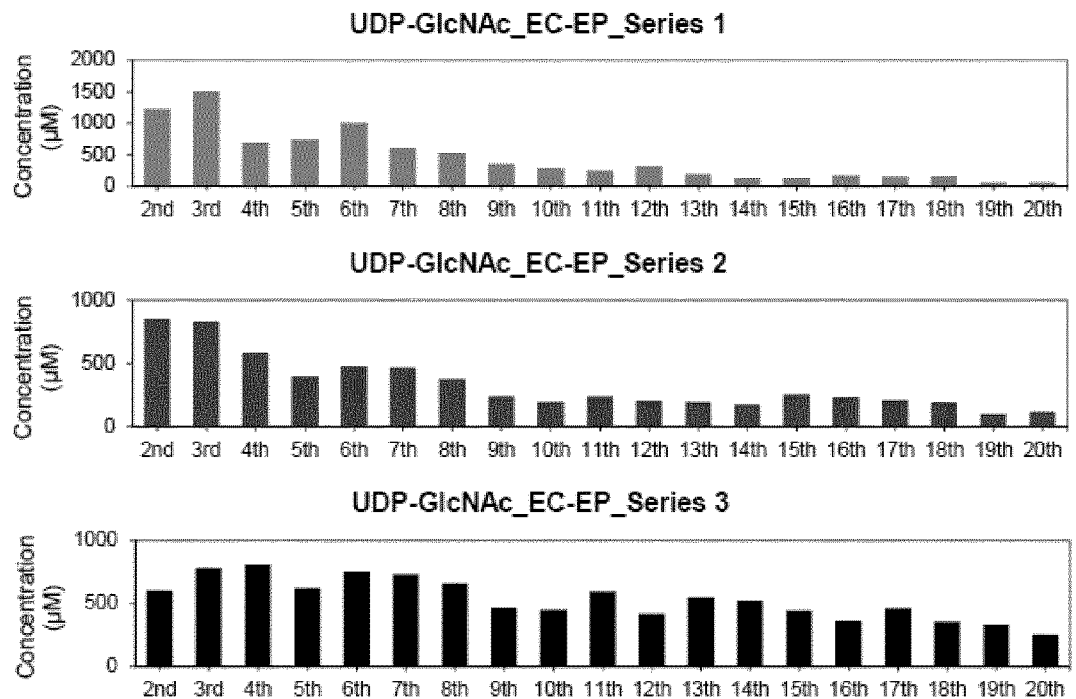
FIG. 14 shows results of the UDP-GlcNAc synthesis with co-immobilized enzymes on EC-EP resin—a methacrylate resin functionalized with epoxy groups—in 20 cycles in 3 series. Productivities were measured by HPAEC-UV.
Figure 15:
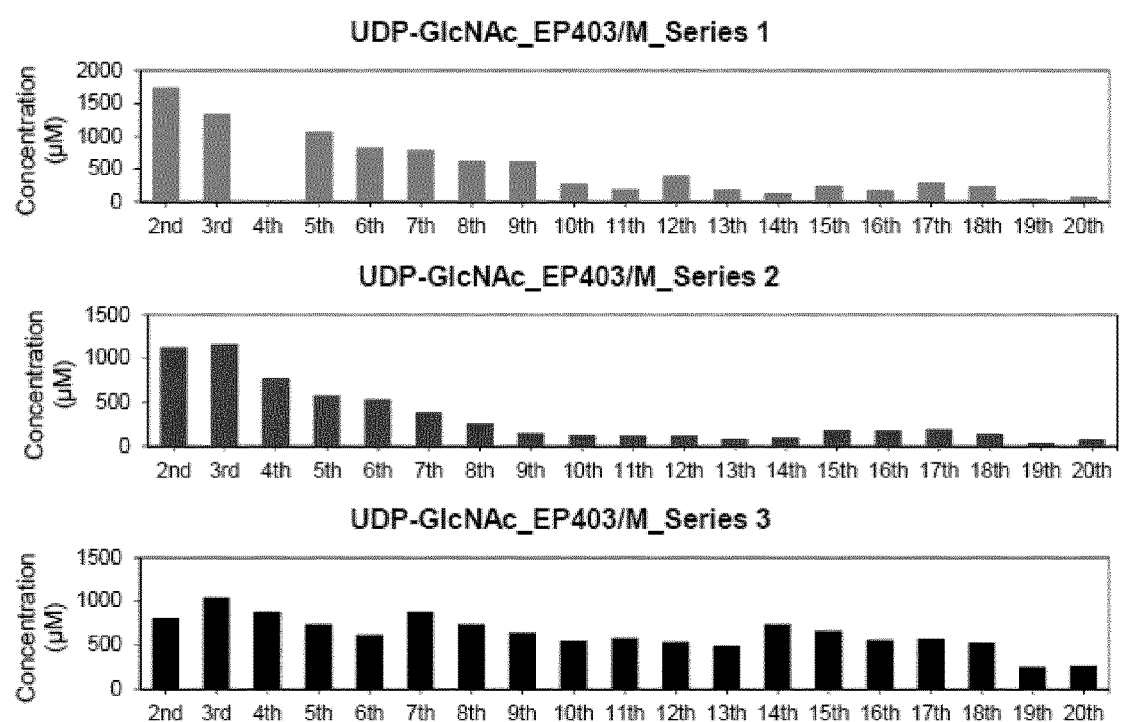
FIG. 15 shows results of the UDP-GlcNAc synthesis with co-immobilized enzymes on EP403/M resin—a methacrylate resin functionalized with epoxy groups—in 20 cycles in 3 series. Productivities were measured by HPAEC-UV.
Figure 16:
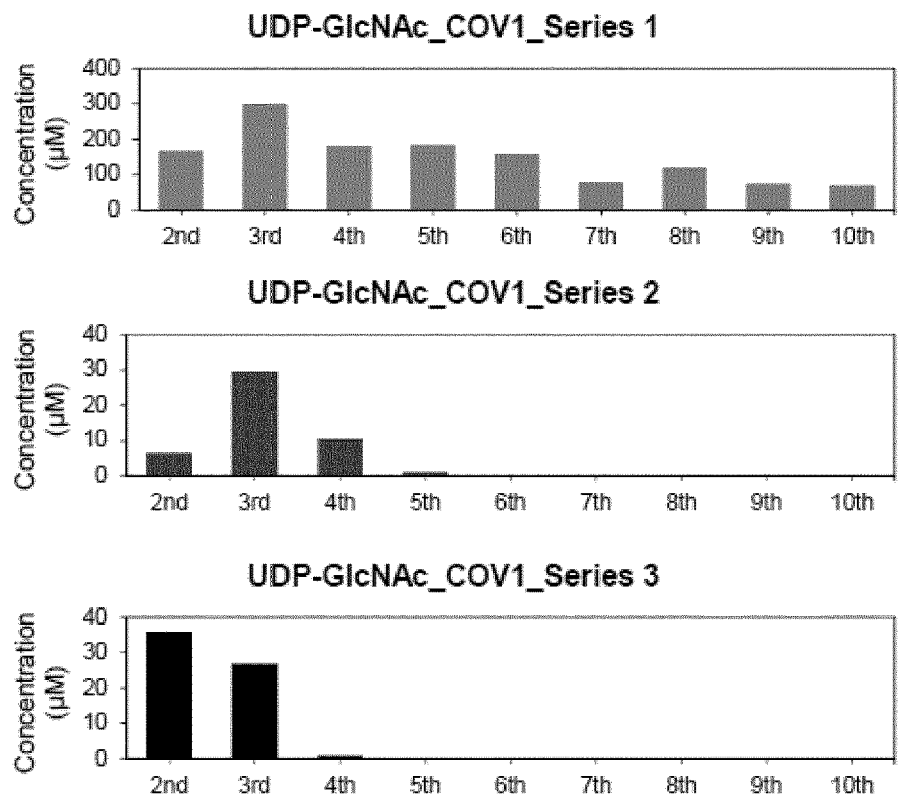
FIG. 16 shows results of the UDP-GlcNAc synthesis with co-immobilized enzymes on COV1 resin—a polyacrylic resin functionalized with butyl/epoxy groups—in 10 cycles in 3 series. Productivities were measured by HPAEC-UV.
Figure 17:
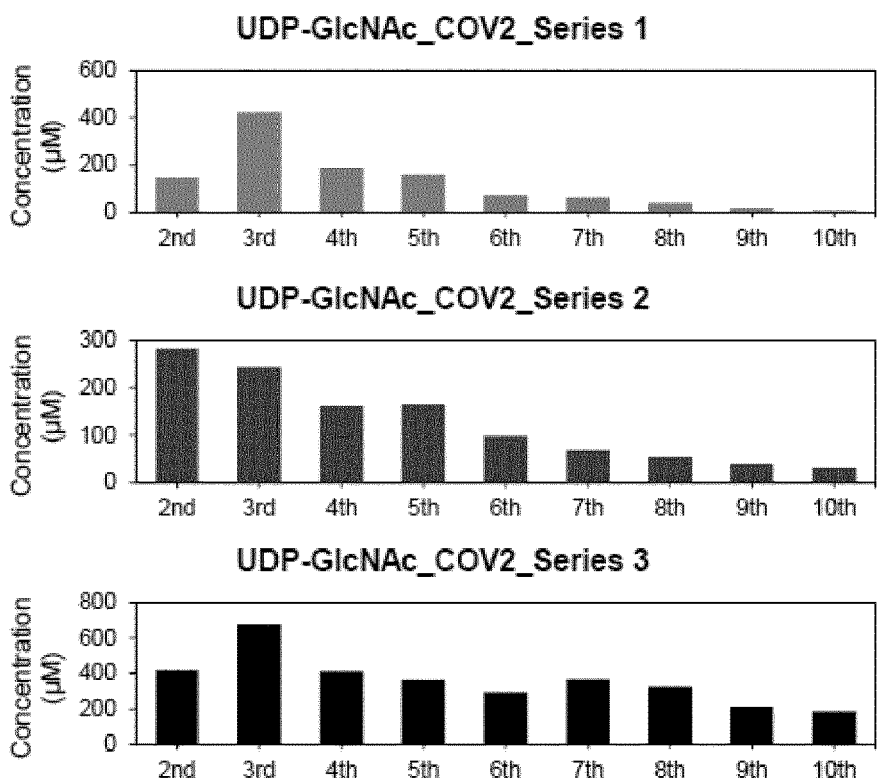
FIG. 17 shows results of the UDP-GlcNAc synthesis with co-immobilized enzymes on COV2 resin—a polyacrylic resin functionalized with epoxy groups—in cycles in 3 series. Productivities were measured by HPAEC-UV.
Figure 18:
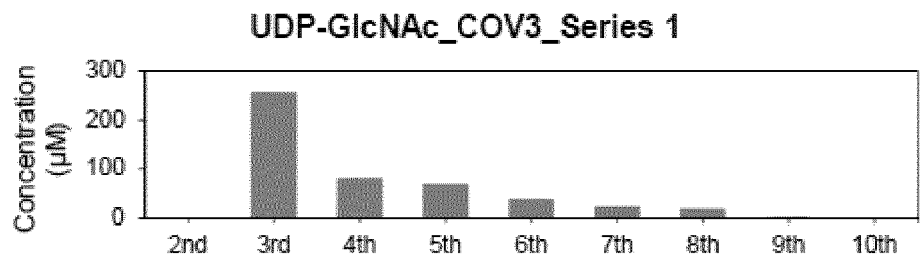
FIG. 18 shows results of the UDP-GlcNAc synthesis with co-immobilized enzymes on COV3 resin—a polyacrylic resin functionalized with epoxy groups—in cycles in 3 series. Productivities were measured by HPAEC-UV.
Figure 18:
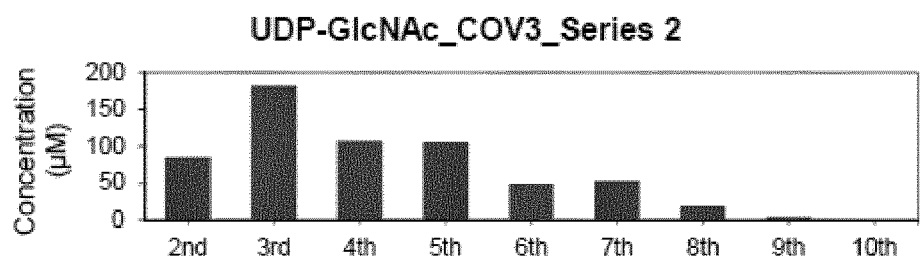
Figure 18:
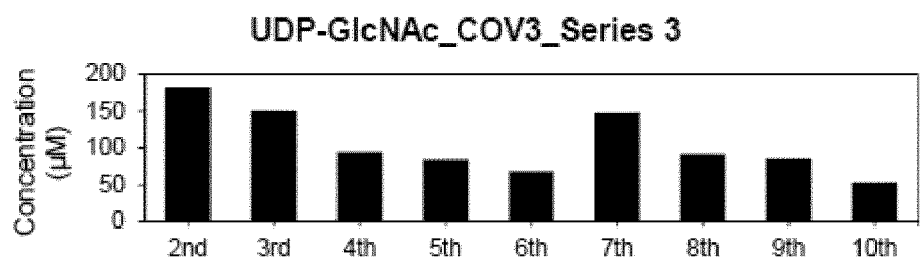
Figure 19:
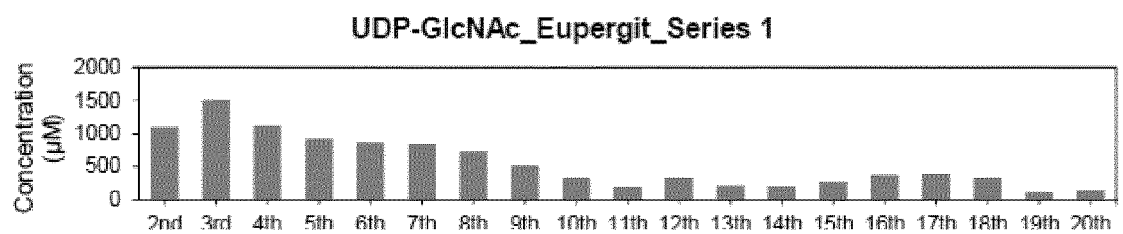
FIG. 19 shows results of the UDP-GlcNAc synthesis with co-immobilized enzymes on Eupergit CM resin—an acrylic resin functionalized with epoxy groups—in 20 cycles. Productivities were measured by HPAEC-UV.
Figure 19:
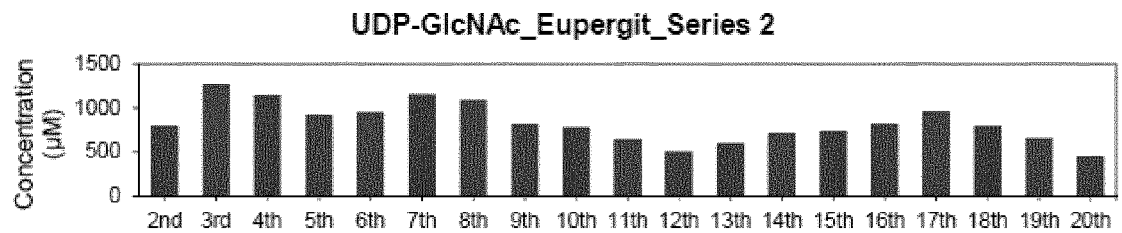
Figure 19:
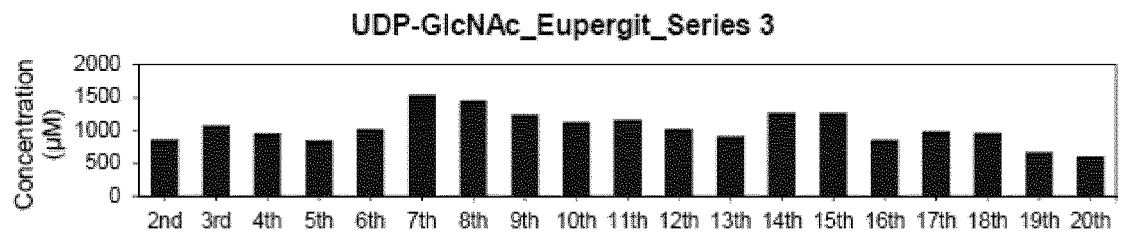
Figure 20:
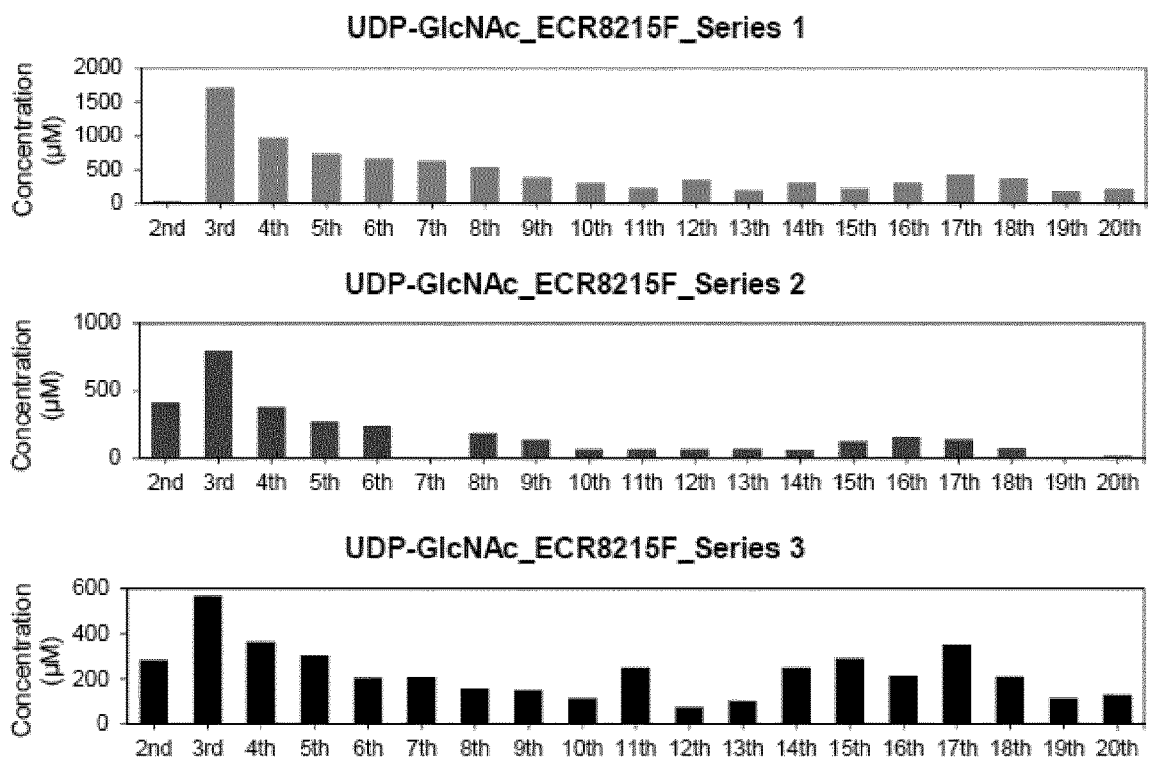
FIG. 20 shows results of the UDP-GlcNAc synthesis with co-immobilized enzymes on ECR8215F resin—a methacrylate resin functionalized with epoxy groups—in 20 cycles. Productivities were measured by HPAEC-UV.
Figure 21:
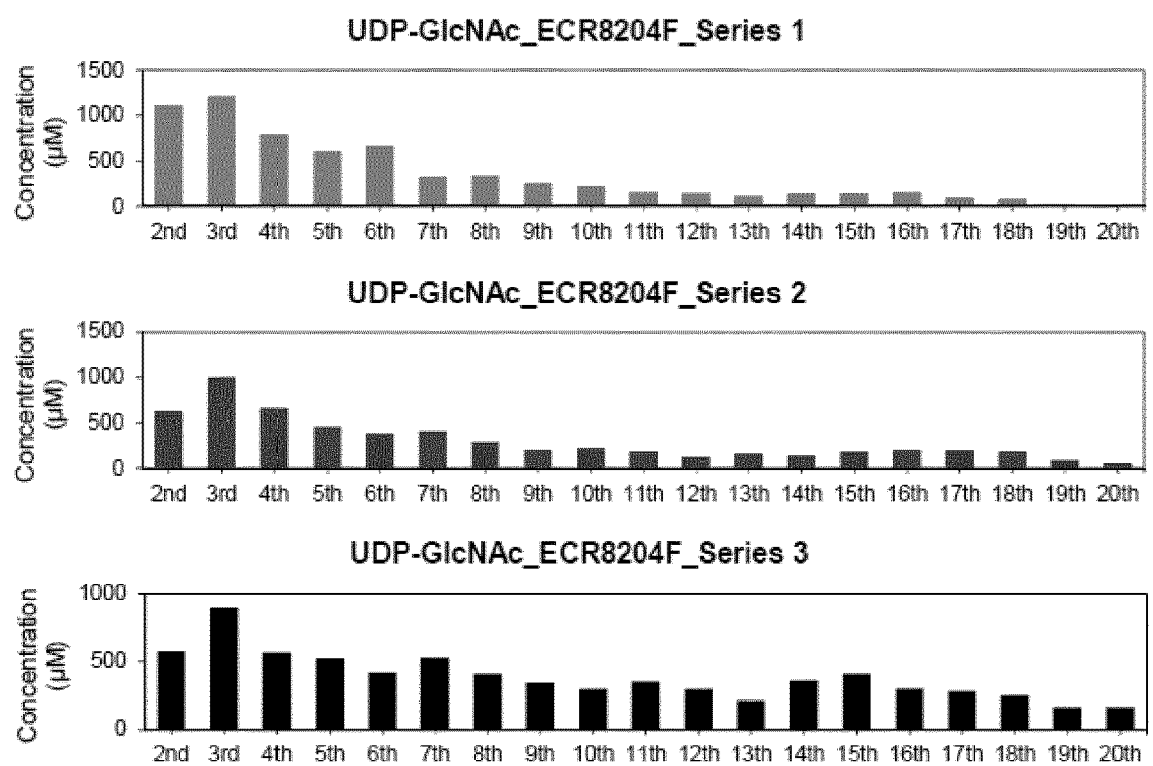
FIG. 21 shows results of the UDP-GlcNAc synthesis with co-immobilized enzymes on ECR8204F resin—a methacrylate resin functionalized with epoxy groups—in 20 cycles. Productivities were measured by HPAEC-UV.
Figure 22:
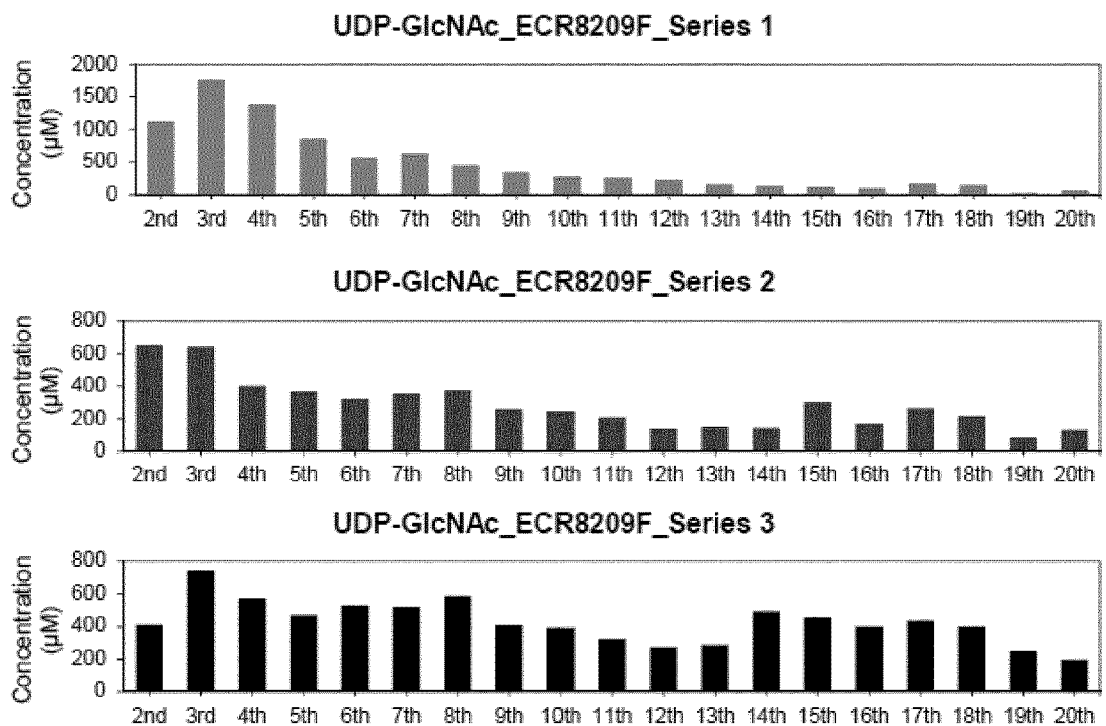
FIG. 22 shows results of the UDP-GlcNAc synthesis with co-immobilized enzymes on ECR8209F resin—a methacrylate resin functionalized with epoxy groups—in 20 cycles. Productivities were measured by HPAEC-UV.
Figure 23:
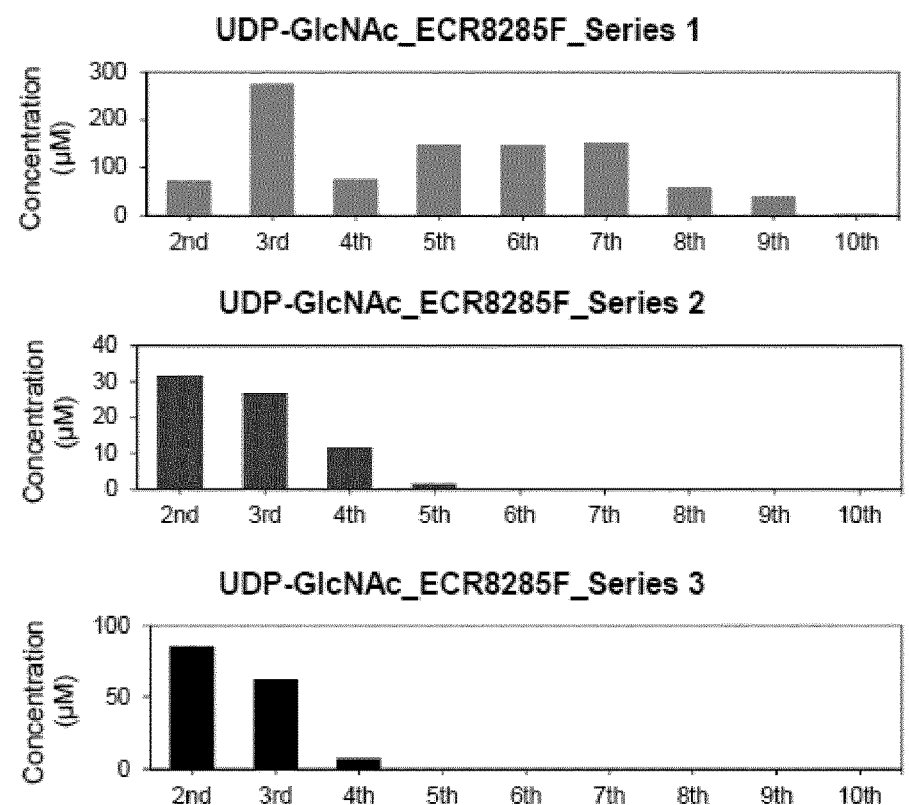
FIG. 23 shows results of the UDP-GlcNAc synthesis with co-immobilized enzymes on ECR8285F resin—a methacrylate resin functionalized with butyl/epoxy groups—in 20 cycles. Productivities were measured by HPAEC-UV.
Figure 24:
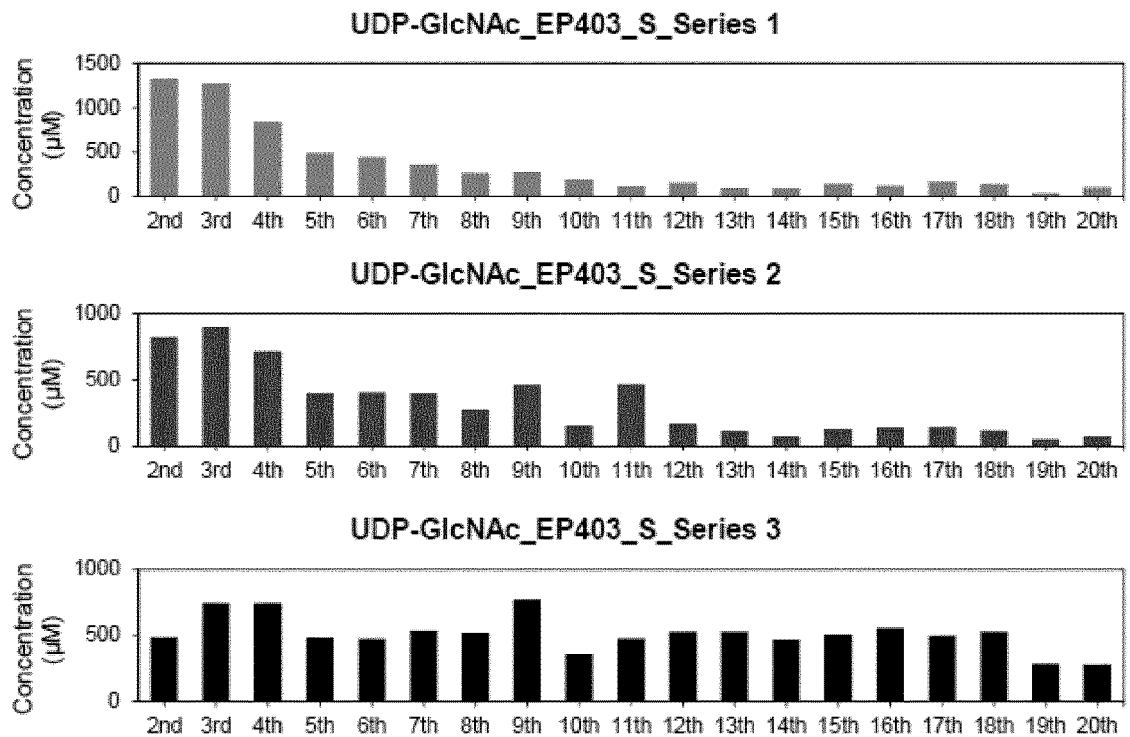
FIG. 24 shows results of the UDP-GlcNAc synthesis with co-immobilized enzymes on EP403/S resin—a polymethacrylate resin functionalized with epoxy groups—in 20 cycles. Productivities were measured by HPAEC-UV.
Figure 25:
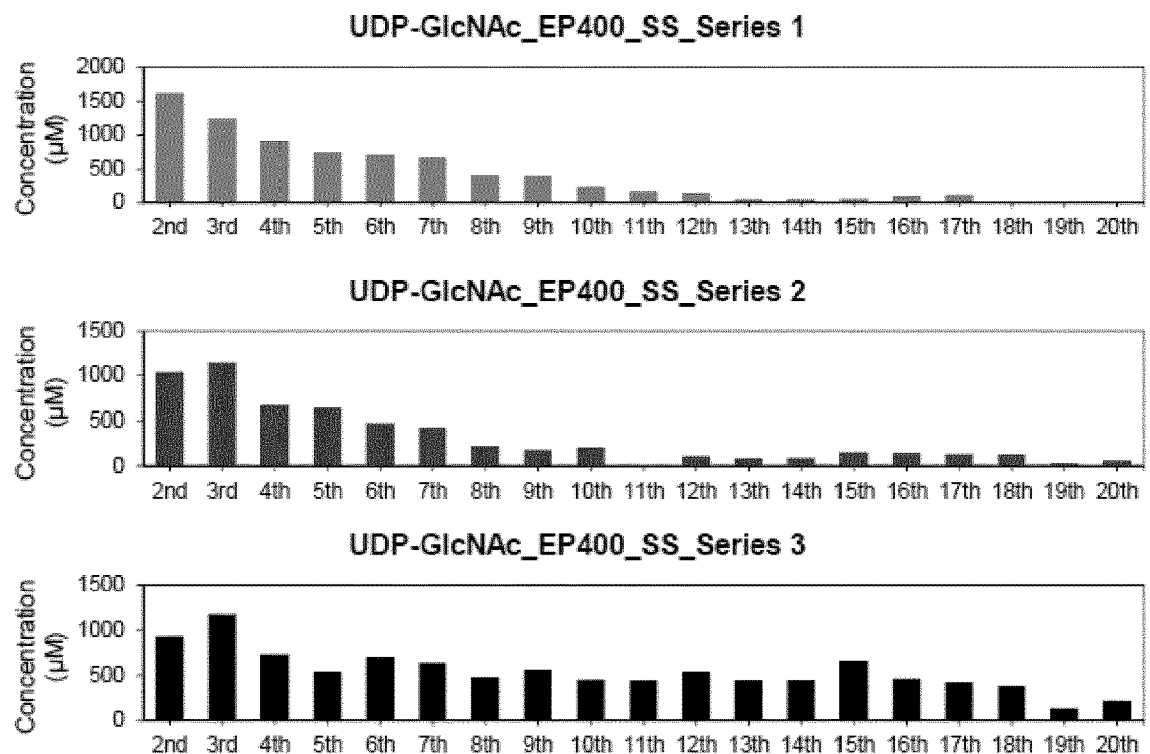
FIG. 25 shows results of the UDP-GlcNAc synthesis with co-immobilized enzymes on EP400/SS resin—a polymethacrylate resin functionalized with epoxy groups—in 20 cycles. Productivities were measured by HPAEC-UV.
Figure 26:
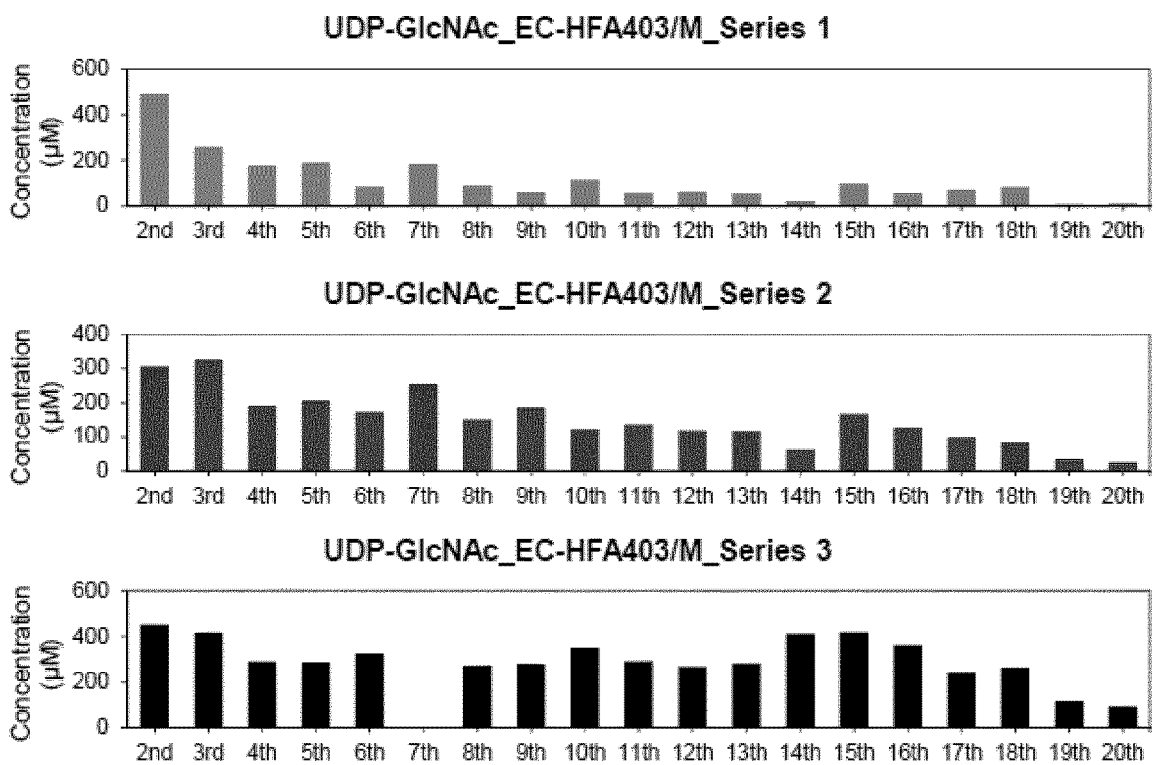
FIG. 26 shows results of the UDP-GlcNAc synthesis with co-immobilized enzymes on EC-HFA 403/M resin—a polymethacrylate resin functionalized with amino epoxy groups—in 20 cycles. Productivities were measured by HPAEC-UV.
Figure 27:
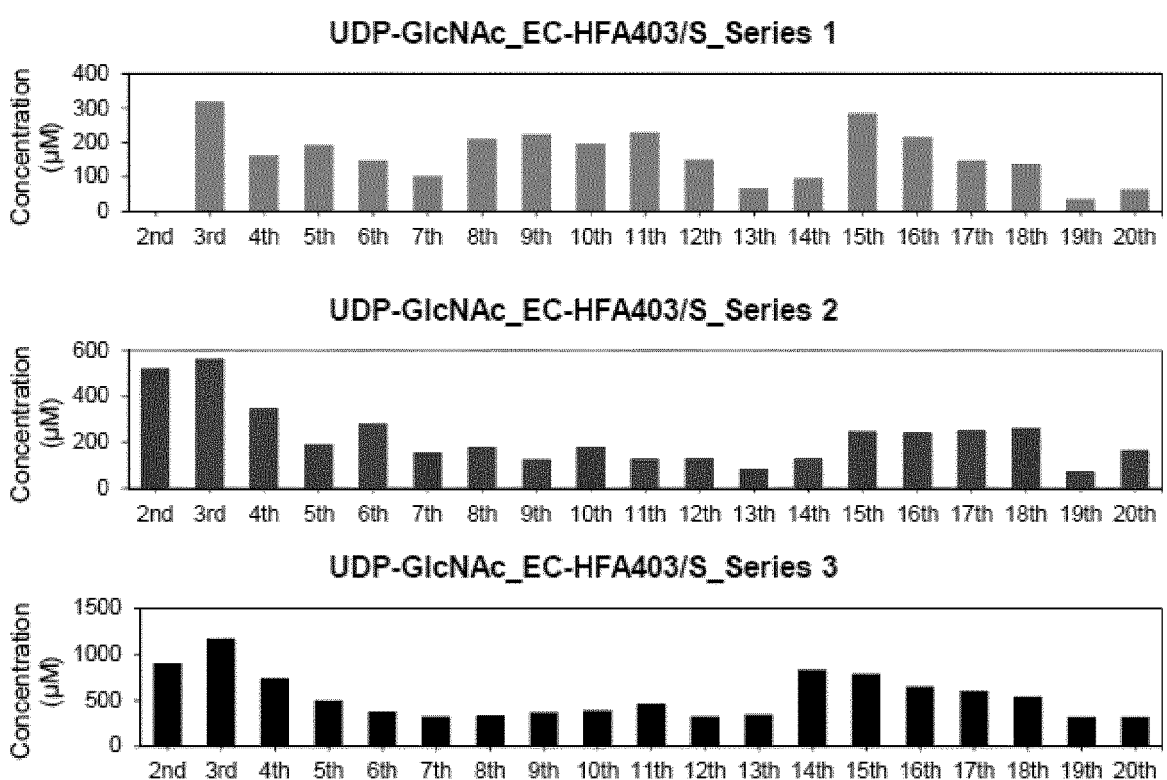
FIG. 27 show results of the UDP-GlcNAc synthesis with co-immobilized enzymes on EC-HFA 403/S resin—a polymethacrylate resin functionalized with amino epoxy groups—in 20 cycles. Productivities were measured by HPAEC-UV.
Figure 28:
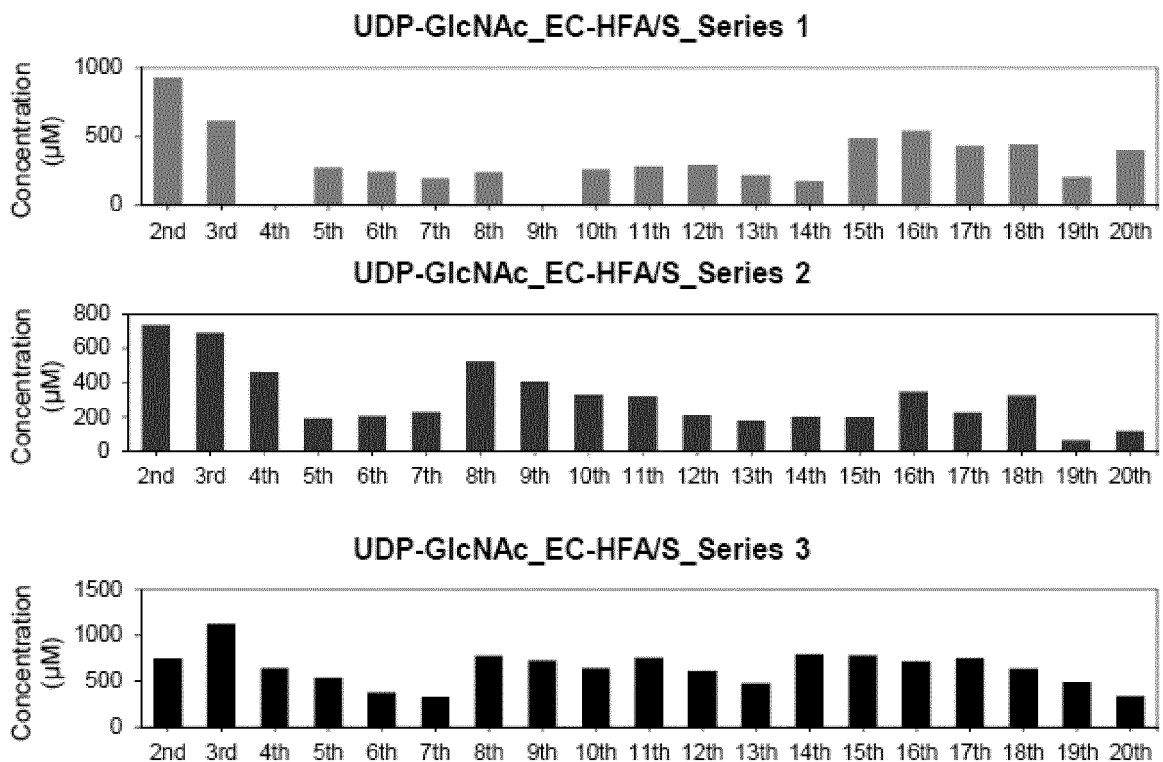
FIG. 28 shows results of the UDP-GlcNAc synthesis with co-immobilized enzymes on EC-HFA/S resin—a polymethacrylate resin functionalized with amino epoxy groups—in 20 cycles. Productivities were measured by HPAEC-UV.
Figure 29:
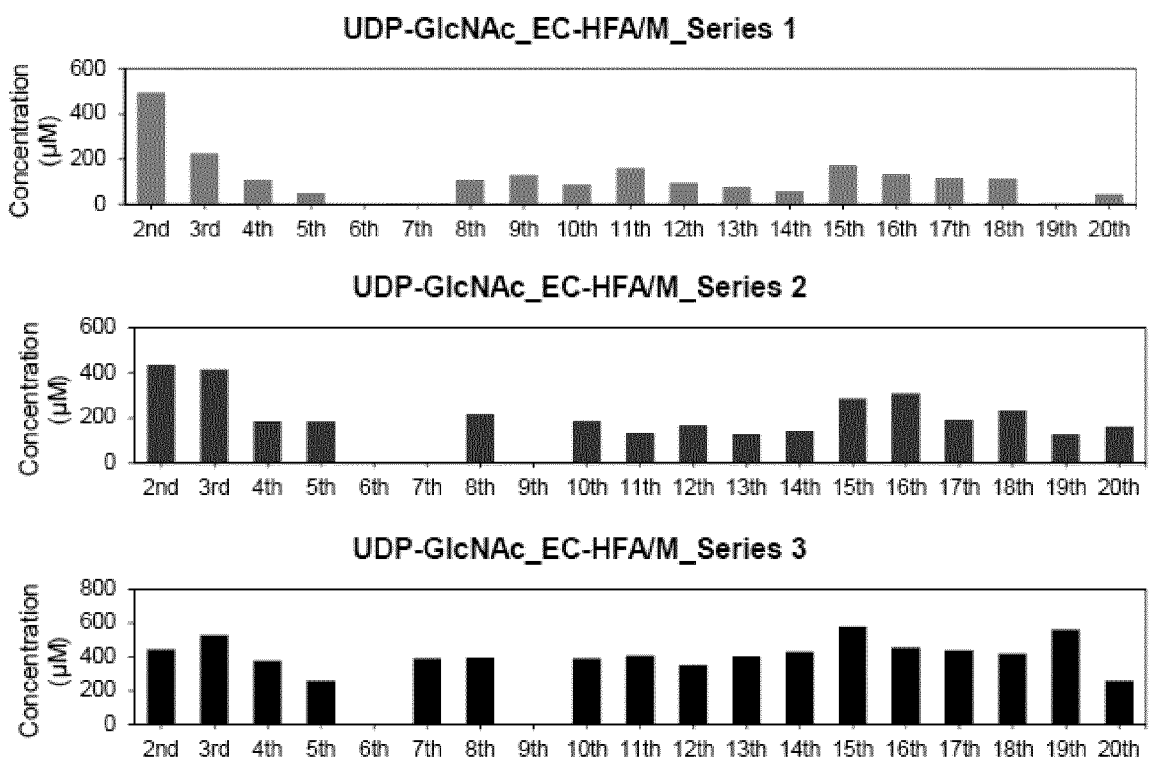
FIG. 29 shows results of the UDP-GlcNAc synthesis with co-immobilized enzymes on EC-HFA/M resin—a polymethacrylate resin functionalized with amino epoxy groups—in 20 cycles. Productivities were measured by HPAEC-UV.
Figure 30:
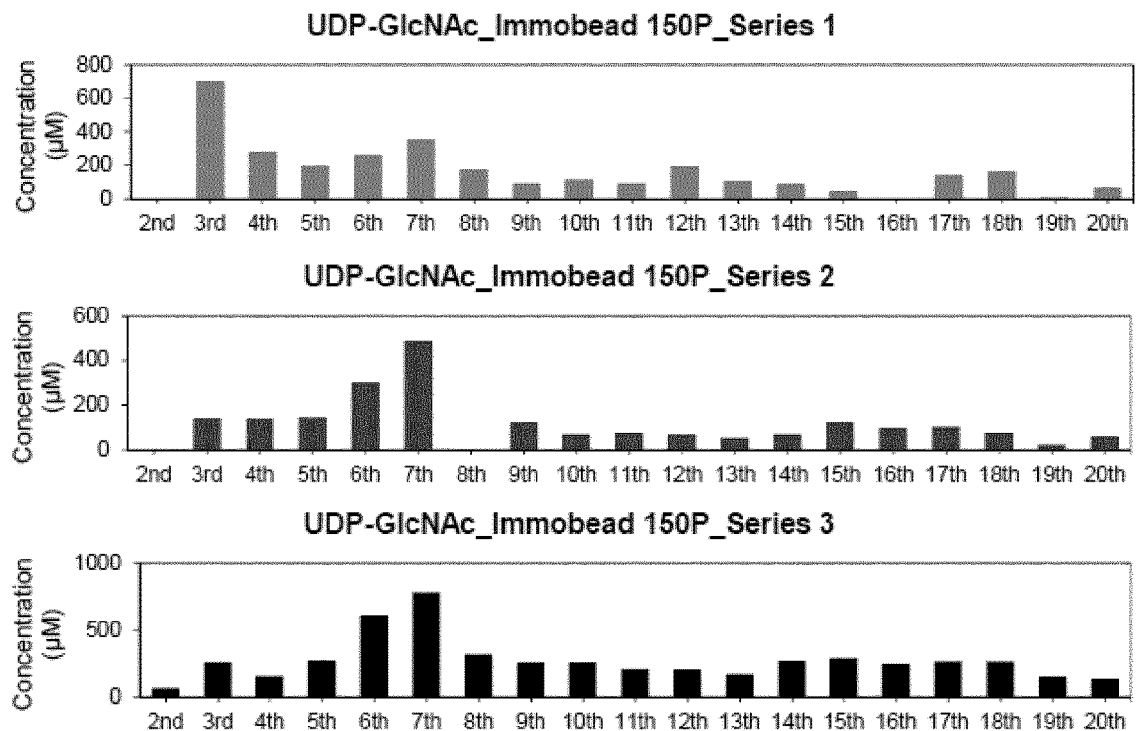
FIG. 30 shows results of the UDP-GlcNAc synthesis with co-immobilized enzymes on Immobead 150P resin—a copolymer of methacrylate resin functionalized with epoxy groups—in 20 cycles. Productivities were measured by HPAEC-UV.
Figure 31:
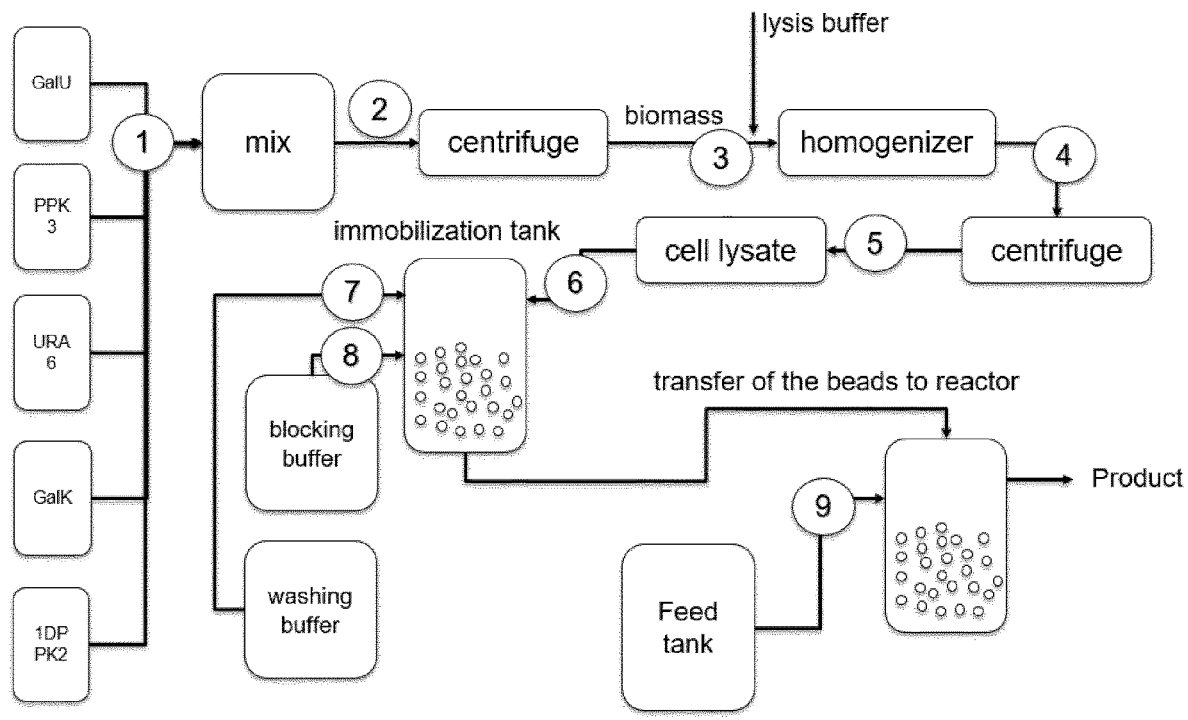
FIG. 31 shows a workflow scheme for the complete UDP-GlcNAc cascade starting from mixing the biomasses containing the overexpressed enzymes to carrying out the synthesis reaction of UDP-GlcNAc on a solid support. The workflow is also suitable for screening various solid supports for enzyme immobilization.
Figure 32:
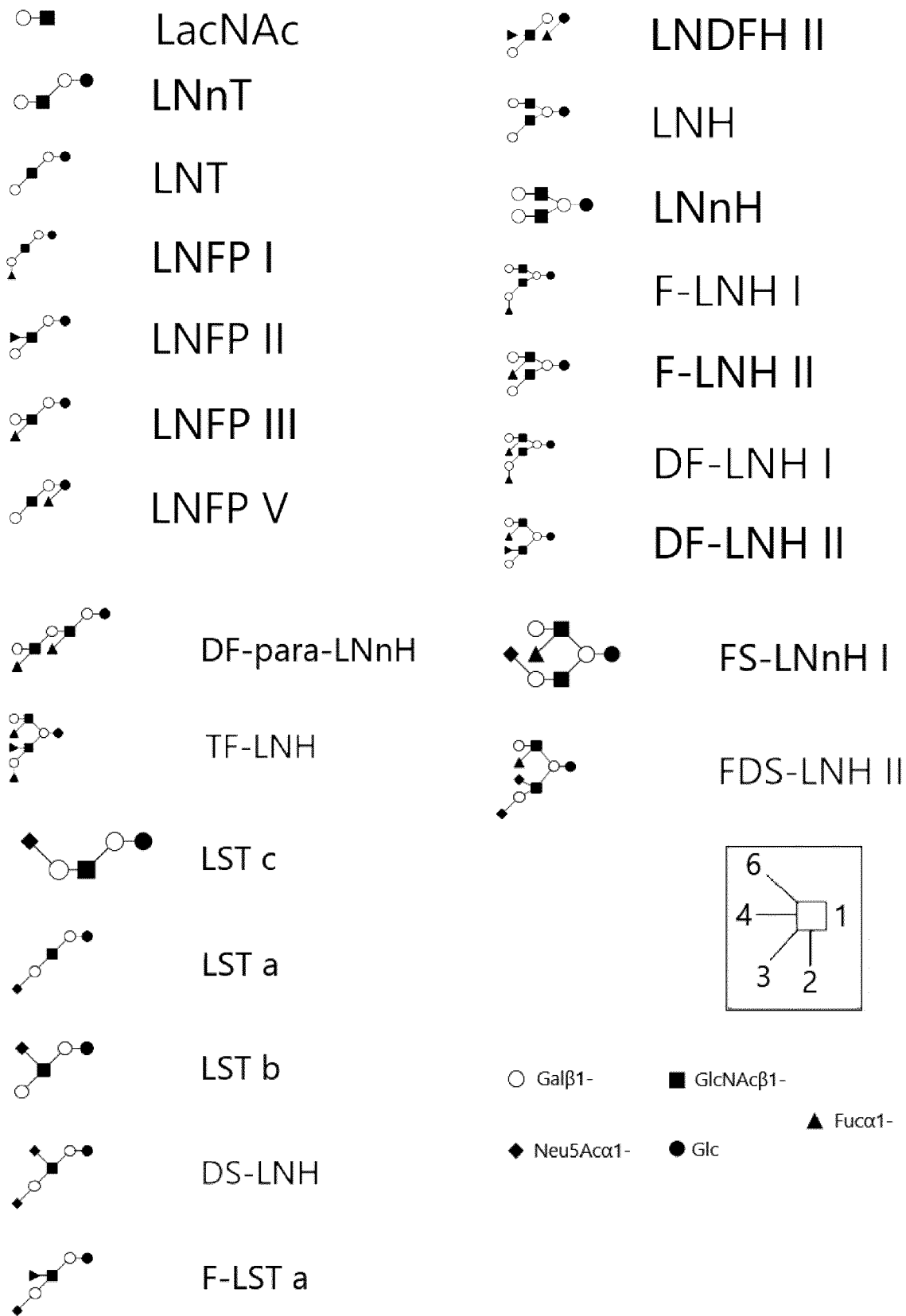
FIG. 32 shows exemplary GlcNAc human milk saccharides.

To test the multi-enzyme cascade—on various supports immobilized-, feed solution (see table 14) containing substrates was transferred to the tubes containing the biocatalysts. To keep a volume of feed to mass of solid support ratio of 1, the following feed volumes were added: 100 μl (series 1), 250 μL (series 2) and 500 μL (series 3). The reactions were carried out for around 20-25 h at 30° C. and shaking in a rotating mixer (8 rpm). To evaluate the reactions, the supernatant was removed and the UDP-GlcNAc concentrations were then measured by HPAEC-UV/PAD. For the quantification by HAPEC-UV/PAD an aliquot of 3 μl was diluted with 100 μl deionized water and then injected. Example chromatograms are shown in FIG. 13A-C. The solid supports were washed with 1 mL deionized water 2 times before starting the next reaction.

TABLE 14

Concentration of reactants in the feed solution.

| Substrate | Conc. (mM) |
|---|---|
| UMP | 5 |
| ATP | 4 |
| GlcNac | 5 |
| PolyP$_{25}$ | 10 |
| HEPES | 100 |
| MgCl$_2$ | 50 |

Results

Enzyme Immobilization

The results of the reaction are shown in FIGS. 14-30. It should be noted that finding the optimal solid support is always down to experimental trial and error as insufficient knowledge about the immobilization of enzymes exist to predict the optimal solid support [3].

The surprising finding was that the multi-enzyme cascade showed activity when co-immobilized on a wide range of epoxy supports. The epoxy supports that were tested and showed activity varied in support matrix, particle size, pore size and oxiran content. Other solid supports where enzymes are immobilized by hydrophobic adsorption, ionic interaction or covalent crosslinking with glutaraldehyde showed very little to no activity implying that at least one of the five key enzymes is little active to inactive. Moreover, the multi-enzyme cascade was active on epoxy supports when a large range of different rations of proteins to solid supports where used. For the synthesis of UDP-GlcNAc, many of the epoxy supports loaded with the enzymes could be used in more than 20 reaction cycles without re-immobilizing the enzymes on the supports.

TABLE 15

Tested Epoxy supports. (+) indicating the multi-enzyme cascade was active or (−) inactive.

| Resin | Mass (mg) | | |
|---|---|---|---|
| | Series 1 | Series 2 | Series 3 |
| EC-EP | + | + | + |
| EP403/M | + | + | + |
| IB-COV1 | + | + | + |
| IB-COV2 | + | + | + |
| IB-COV3 | + | + | + |
| Eupergit ® CM | + | + | + |
| ECR8215F | + | + | + |
| ECR8204F | + | + | + |
| ECR8209F | + | + | + |
| ECR8285 | + | + | + |
| EP403/S | + | + | + |
| EP400/SS | + | + | + |
| EC-HFA/M | + | + | + |
| HFA403/M | + | + | + |
| HFA403/S | + | + | + |
| EC-HFA/S | + | + | + |
| Imm150P | + | + | + |

TABLE 16

Tested Ionic & Adsorption supports: (+) indicating the multi-enzyme cascade was active or (−) inactive.

| Resin | Mass (mg) | | |
|---|---|---|---|
| | Series 1 | Series 2 | Series 3 |
| 8409F | − | − | − |
| 8315F | − | − | − |
| 8309F | − | − | − |
| 1030F | − | − | − |
| 1504 | − | − | − |
| 8806F | + | + | + |
| 8415F | − | − | − |
| 1091M | + | + | + |
| 1604 | − | − | − |
| EC-EA/M | − | − | − |
| EC-HA | − | − | − |
| EA403/S | − | − | − |
| ADS-1 | + | + | + |
| ADS-2 | + | + | + |
| ADS-3 | − | − | − |
| ADS-4 | − | − | − |
| CAT-1 | − | − | + |
| ANI-1 | − | − | − |
| ANI-2 | − | − | − |
| ANI-3 | − | − | − |
| ANI-4 | − | − | − |

TABLE 17

Tested Glutaraldehyde activited supports. (+) indicating the multi-enzyme cascade was active or (−) inactive. Glutaraldehyde activated supports are supports with amine-reactive groups that were activated by glutaraldehyde to generate covalent binding between protein and solid support.

| Resin | Mass (mg) | | |
|---|---|---|---|
| | Series 1 | Series 2 | Series 3 |
| 8409F | + | − | − |
| 8315F | + | − | − |
| 8309F | − | − | − |
| 8415F | − | − | − |
| EC-EA/M | + | − | − |
| EC-HA | + | − | − |
| EA403/S | + | − | − |

Example 3: Coupling of the Cascade

The cascade can be coupled to GlcNAc-transferases (EC 2.7.1.X) to transfer GlcNAc to acceptor molecules. Acceptor molecules can be for example monoclonal antibodies. For the coupling soluble GlcNAc-transferase can be added, a GlcNAc-transferase can be co-immobilized on the same support and/or the GlcNAc-transferase can be immobilized on an additional support and then be added to reaction.

Example 4: Synthesis of UDP-GlcNAc by a Multi-Enzyme Cascade Immobilized on Ni-NTA Solid Supports Enzymes of the UDP-GlcNAc synthesis pathway were recombinantly produced in E. coli as detailed before. The bio mass was mixed as detailed in Table 18A and homogenized for 8 minutes at 800-1000 psi in 150 mL lysis buffer (see Table 18B). The cell lysate was centrifuged (7000×g, 45 min) and the supernatant containing the enzymes was filtered (1.8 μm filter). A total protein concentration of 10 mg/mL was determined. To prepare the immobilization 500 μL of the Ni-NTA bead slurry were transferred each to 2 mL Eppendorf tubes and equilibrated with lysis buffer containing additionally 10 mM imidazole. Immobilization on Ni-NTA was carried out by incubating 1.5 mL lysate with the preequilibrated beads in immobilization buffer (lysis buffer plus 10 mM imidazole). After immobilization the beads were washed three times with washing buffer (see Table 18C).

TABLE 18

A. Biomass mix used for the immobilization. B. Lysis buffer. C. Washing buffer

| | A. | B. | | C. | |
|---|---|---|---|---|---|
| Enzyme | Mass of biomass (g) | Lysis buffer | Conc. (mM) | Wash. buffer | Conc. (mM) |
| NahK | 6.14 | HEPES | 250 | HEPES | 400 |
| URA6 | 4.13 | $MgCl_2$ | 50 | $MgCl_2$ | 50 |
| GalU | 13.63 | NaCl | 300 | NaCl | 600 |
| PPK3 | 11.92 | glycerol | 5% | glycerol | 5% |
| PmPpA | 1.08 | | | | |

A reaction cycle was carried out to assess the activity of the beads. Each of the reactions was carried out for 20-25 hours at 30° C. and shaking at 600 rpm. To start a reaction 250 μL of the feed solution was added to the washed beads (Table 19). In between the experiments the supernatant was removed and the beads were washed 2 times with 1 mL deionized water.

TABLE 19

Feed solution for UDP-GlcNAc synthesis.

| Substrate | Conc. (mM) |
|---|---|
| UMP | 5 |
| ATP | 4 |
| GlcNAc | 5 |
| PolyP$_{25}$ | 10 |
| HEPES | 100 |
| MgCl$_2$ | 50 |

Figure 33:
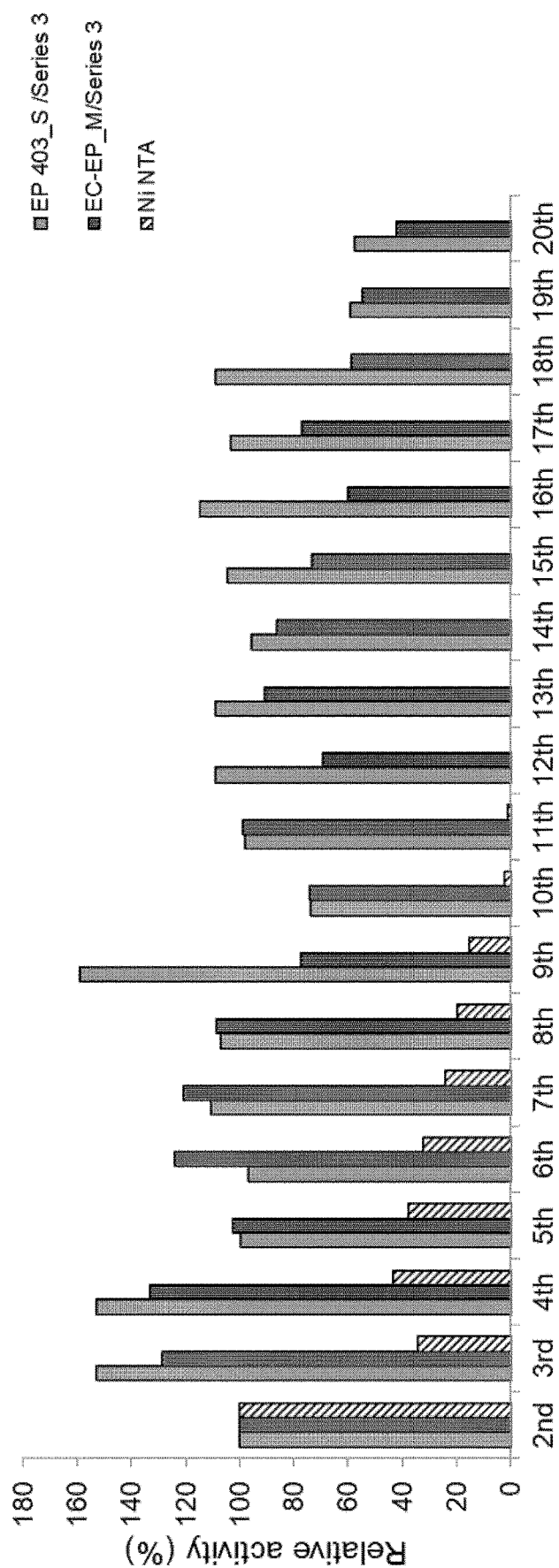
FIG. 33 shows the activity of EP403/S, EC-EP/M and Ni-NTA beads up to 20 cycles for the synthesis of UDP-GlcNAc. Ni-NTA experiments were carried out in triplicates.

The UDP-GlcNAc cascade immobilized on Ni-NTA beads shows decreasing activity for nine reactions (see FIG. 33). Some residual activity is detectable in reaction number 10 and 11 but is negligible compared to the activity on epoxy beads. In summary, the cascade immobilized on a wide range of solid supports with epoxy functional groups shows extended activity in comparison to Ni-NTA beads. Consequently, epoxy beads can be reused more often and are, hence, more economical.

Example 5: Synthesis of UDP-GlcNAc from Uridine and GlcNAc

Figure 2:
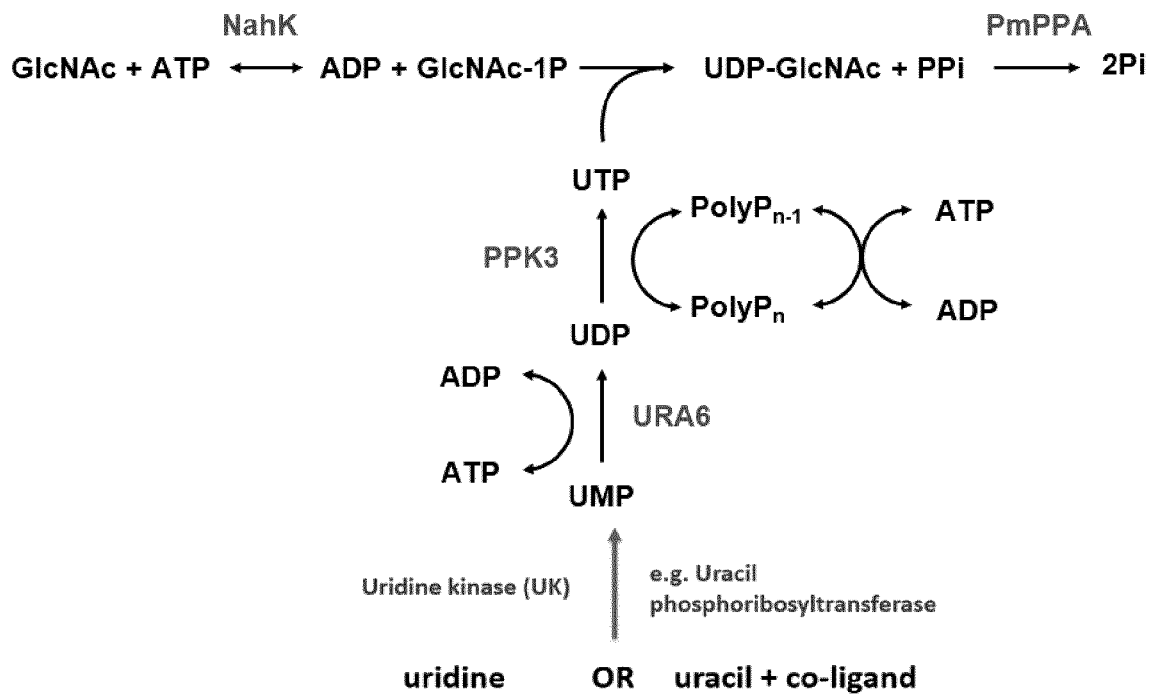
FIG. 2: shows an exemplary reaction scheme of the inventive method for producing UDP-N-acetyl-α-D-glucosamine starting from uridine or uracil and 5-phospho-α-D-ribose 1-diphosphate. The formation of UMP from uridine is catalyzed by uridine kinase and the formation of UMP from uracil is catalyzed by uracil phosphoribosyltransferase.
Figure 3:
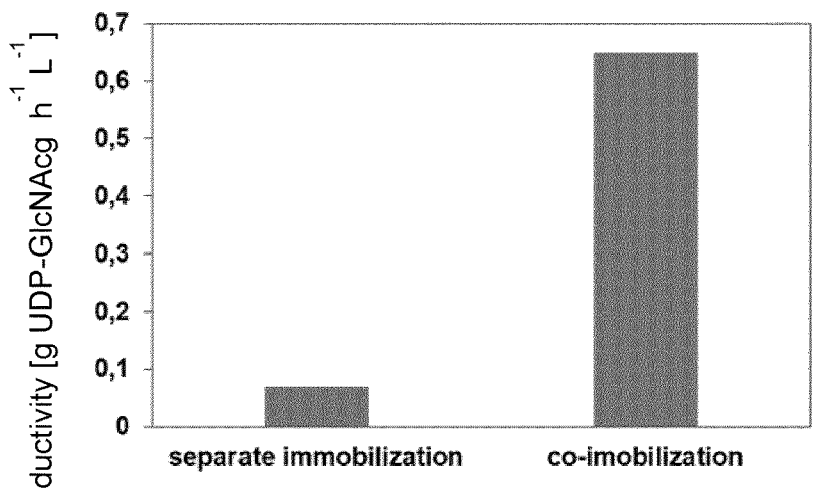
FIG. 3: shows the comparison of the productivity for the synthesis of UDP-GlcNAc with separately immobilized enzymes and co-immobilization of the set of enzymes. Co-immobilization results in much higher productivity.

The cascade for synthesis of UDP-GlcNAc from uridine is shown in FIG. 2. The cascade contains six enzymes and seven reactions. Uridine (Uri), N-acetyl-glucosamine (GlcNAc), polyphosphate (PolyP$_n$) are used as the main substrates, including catalytic amount of adenine triphosphate (ATP).

Recombinant Production of Enzymes

The list of the plasmids used in this study is shown in Table 20. LOBSTR *E. coli* competent cells (Kerafast, US) were used as the expression host. Cells were transformed based on heat-shock protocol. The fermentation carried out in TB media supplement with 1.5 mM MgSO$_4$ and corresponding antibiotic. The cells were cultivated at 37° C. until OD$_{600}$ of 0.8-1.0 was observed. Afterwards, induction was carried out with 0.4 mM IPTG, followed by 20-24 h cultivation at 16° C.

At the end of the cultivation, cells were harvested by centrifugation (7000×g, 20 minutes) and cell pellets were resuspended in lysis buffer (50 mM MOPS buffer, 300 mM NaCl, 10 mM MgCl$_2$, 10 mM imidazole and 5% glycerol at pH 7.4) and were disrupted by high-pressure homogenizer (Maximator, Germany) (3 times passage at 800-1000 psi). The His-tag purification was performed based on immobilized metal affinity chromatography with ÄKTA start instrument (GE Health care Life Sciences, Uppsala, Sweden) in combination with 1 mL or 5 mL HisTrap HP (GE Health care Life Sciences, Sweden) columns. The binding buffer contains: 50 mM MOPS buffer, 300 mM NaCl, 10 mM MgCl$_2$, 10 mM imidazole and 5% glycerol at pH 7.4. And the elution buffer consists of 50 mM MOPS buffer, 300 mM NaCl, 10 mM MgCl$_2$, 250 mM imidazole and 5% glycerol at pH 7.4.

In order to remove imidazole from elution buffer and concentrate the enzyme solution, buffer exchange performed with Amicon® Ultra-15 Centrifugal Filter Unit—3 KDa MW cutoff (Merck, Germany). The exchange buffer contained: 50 mM MOPS buffer, 300 mM NaCl, 10 mM MgCl$_2$, 5% glycerol at pH 7.4. Afterwards, the retentate solution (concentrated enzyme) was mixed 1:1 with glycerol to have the final enzyme solution in 50% glycerol and enzymes were stored at −20° C.

TABLE 20

Enzymes used in this example, their origin, and expression plasmid

| Gene | Abbr. | Enzyme | Uniprot. No. | Origin | Plasmid | SEQ ID No |
|---|---|---|---|---|---|---|
| Nahk | NahK | N-acetylhexosamine 1 kinase | E8MF12 | *Bifidobacterium longum* | pET-28a(+) | 1 |
| glmu | GLMU | UTP-GlcNAc-1-phosphate uridylyl transferase | Q9CK29 | *Pasteurella multocida* | pET-15b | 8 |
| ppa | PmPpa | Inorganic diphosphatase | P57918 | *Pasteurella multocida* | pET-28a(+) | 5 |
| udk | UDK | uridine/cytidine kinase | P0A8F4 | *Escherichia coli* (strain K12) | pET-28a(+) | 9 |
| UMK3 | URA6 | UMP/CMP kinase | O04905 | *Arabidopsis thaliana* | pACYCDuet | 2 |
| SPO1727 | PPK3 | NDP kinase/polyP$_n$ kinase | Q5LSN8 | *Ruegeria pomeroyi* | pACYCDuet | 3 |
| LgtA | β1,3Glc NAcT | β-1,3-N-acetylglucosamine transferase | Q51115 | *Neisseria meningitidis* | pMAL-c4X | 10 |

Experiment A: Synthesis of UDP-GlcNAc with Purified Enzymes

Figure 34:
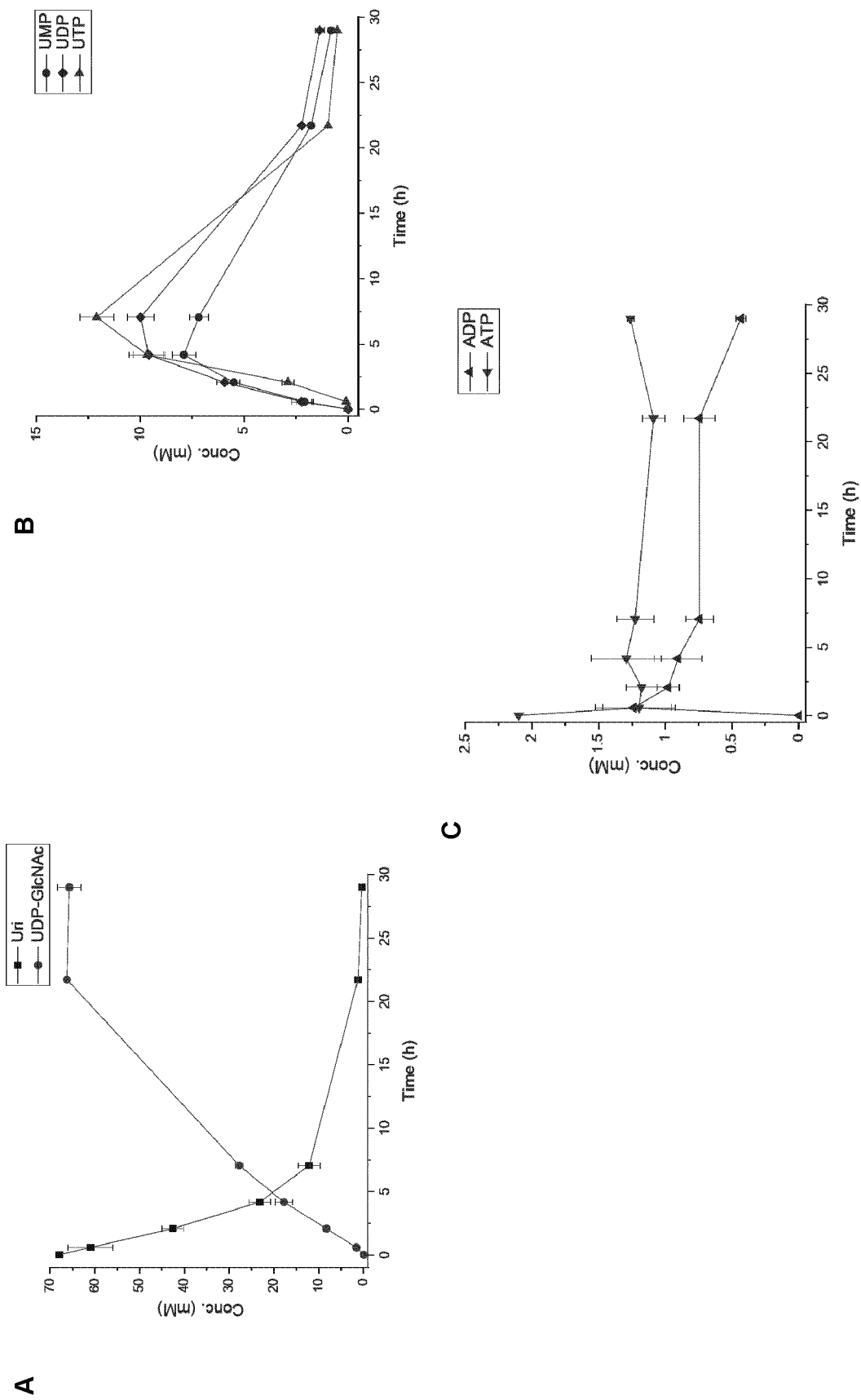
FIG. 34 shows intermediates and product formed in the UDP-GlcNAc cascade of Example 5. (A) UDP-GlcNAc; (B) UMP, UDP and UTP; (C) ADP and ATP. The experiments were carried out in triplicate; error bars represent standard deviation.

Reactions were conducted at 200 µL, 37° C. and 550 rpm. The reaction conditions were as follows: UDK, 0.07 µg/µL; URA6/PPK3, 0.11 µg/µL; NAHK, 0.18 µg/µL; GLMU, 0.2 µg/µL; PmPpa, 0.05 µg/µL; uridine, 68 mM; GlcNAc, 68 mM; ATP, 2.1 mM; PolyP$_n$, 21 mM; Tris-HCl (pH, 8.5), 150 mM; MgCl$_2$, 75 mM. The successful production of UDP-GlcNAc and concentration of the cascade intermediates are shown in FIG. 34. UDP-GlcNAc was produced in quantitative yield which results in a final concentration of ~40 g/L Experiment B: Large-Scale Synthesis of UDP-GlcNAc For preparation of cell lysate for synthesis of UDP-GlcNAc the following biomasses were mixed: UDK, 6.65 g; URA6/PPK3, 9.26 g; NAHK, 11.23 g; GLMU, 6.9 g; PmPpa, 4.94 g in 200 mL of 50 mM HEPES buffer (pH 8.1), 400 mM NaCl, and 5% glycerol. The mixture was passed three times through a high-pressure homogenizer. Cell-free extract was centrifuged at 11,000×g for 45 min. Afterwards, preliminary experiments were carried out on a small scale (200 µL) to find a suitable amount of lysate for the synthesis. The findings based on 200 µL synthesis was directly used for 4 liter scale synthesis which correlate to a 20,000× scaling factor.

To carry out a 4-liter large scale experiment, a seven-liter single wall glass autoclavable bioreactor (Applikon, Netherlands), equipped with two pitched-blade impellers was selected to carry out the large-scale production.

Figure 35:
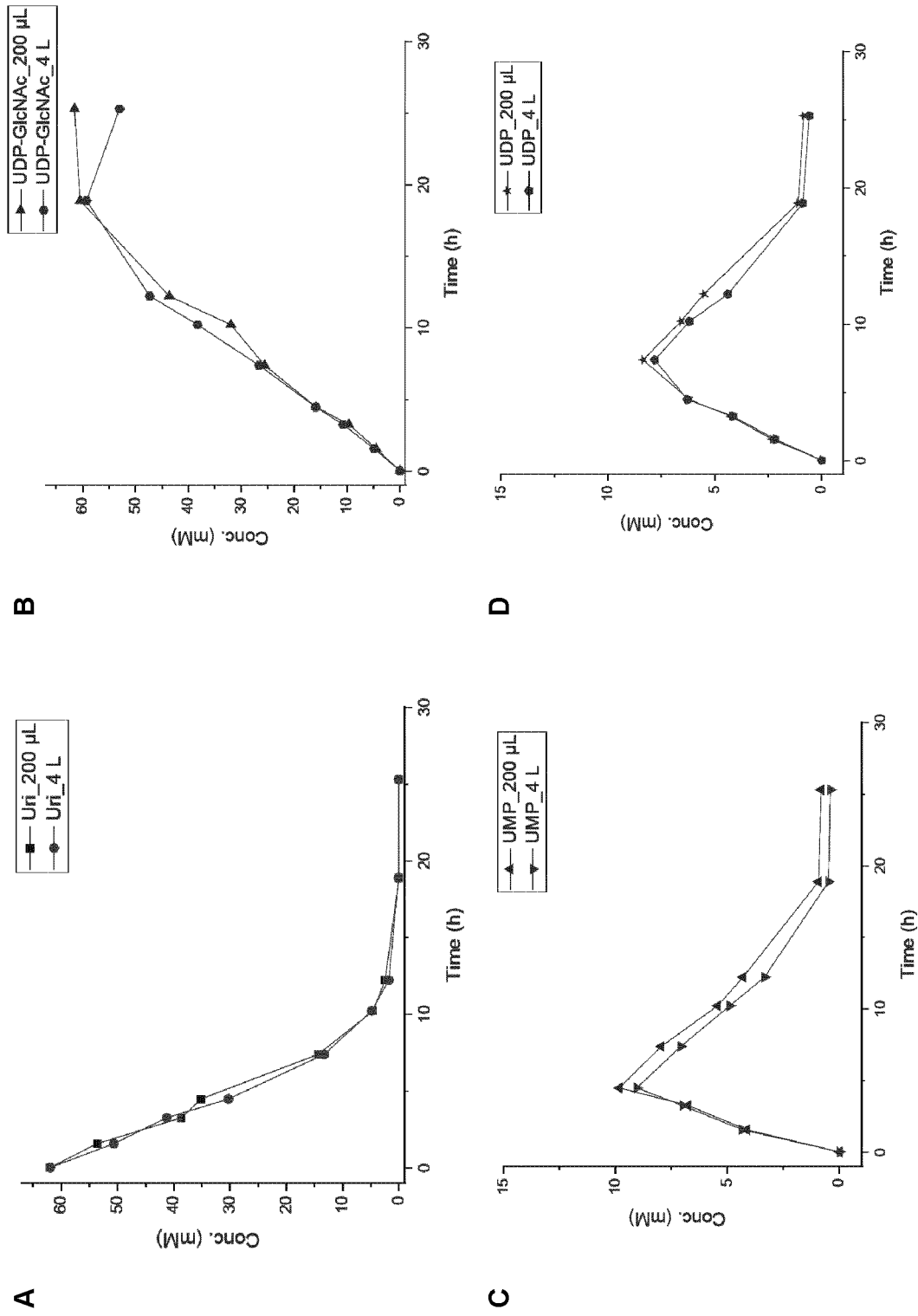
FIG. 35 shows educts, intermediates and product formed in the UDP-GlcNAc scale-up experiment of Example 5. (A) uridine; (B) UDP-GlcNAc; (C) UMP; (D) UDP; (E) UTP; (F) ATP; and (G) ADP.
Figure 35:
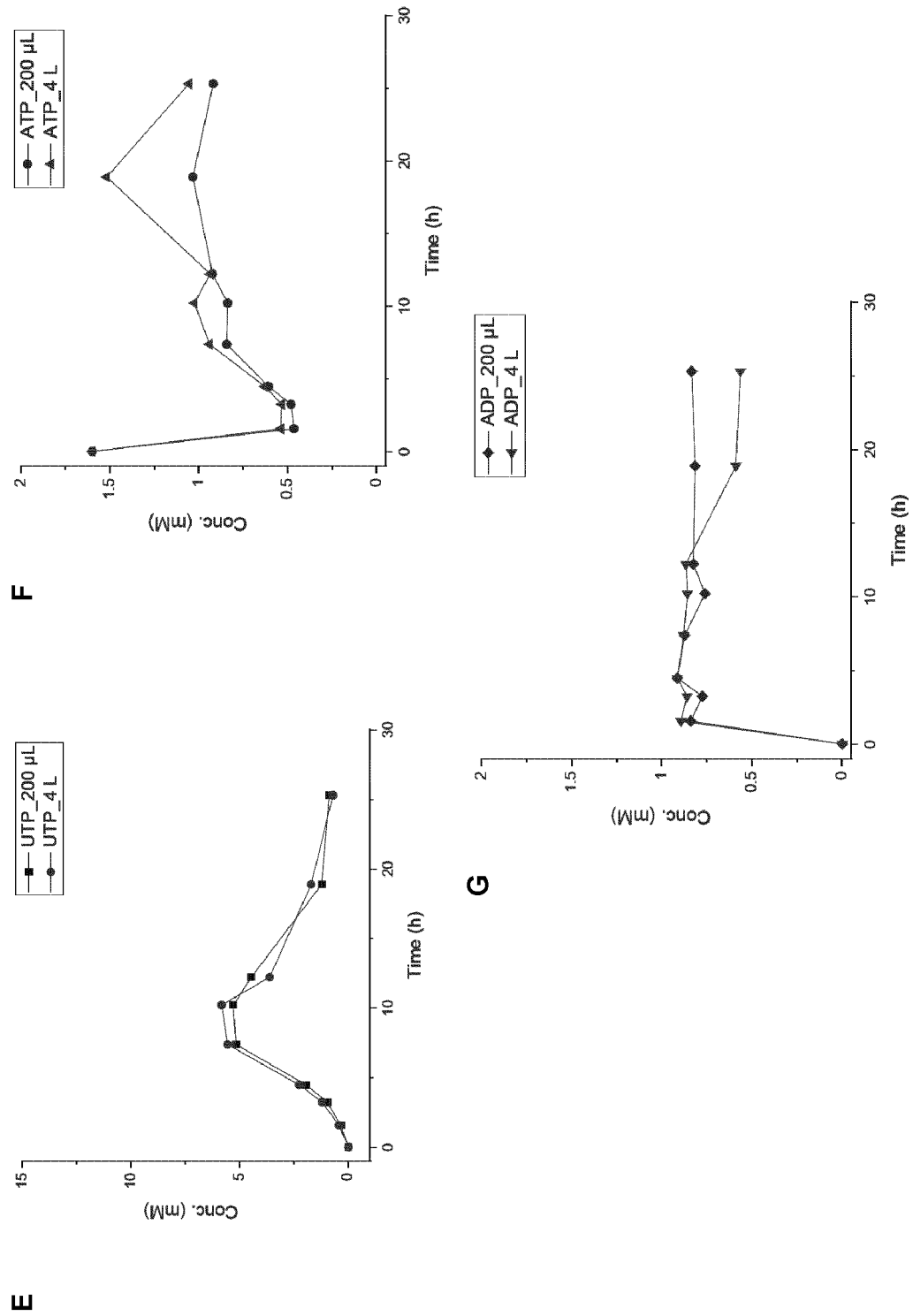

The synthesis conditions were as follows: 200 mM Tris-HCl (pH 8.5), 62 mM uridine, 62 GlcNAc, 1.6 mM ATP, 18 mM PolyP$_n$, 75 mM MgCl$_2$, and total protein load of 0.5 g/L in the form of cell lysate. The reaction was carried out at 37° C. room and 120 rpm. To understand the effect of scale-up on the performance of the cascade, a parallel 200 µL experiment was carried out. The time course of cascade intermediates is shown in FIG. 35.

Experiment C: Synthesis of UDP-GlcNAc with Immobilized Enzymes

For making the process closer to future industrial application, immobilization was carried out by using cell lysate containing all the necessary enzymes (as described above). The cell lysate solution was the same as used in 4-L scale synthesis of UDP-GlcNAc. The list of the beads used in this study as a support for co-immobilization of enzyme are described in Table 21.

Figure 36:
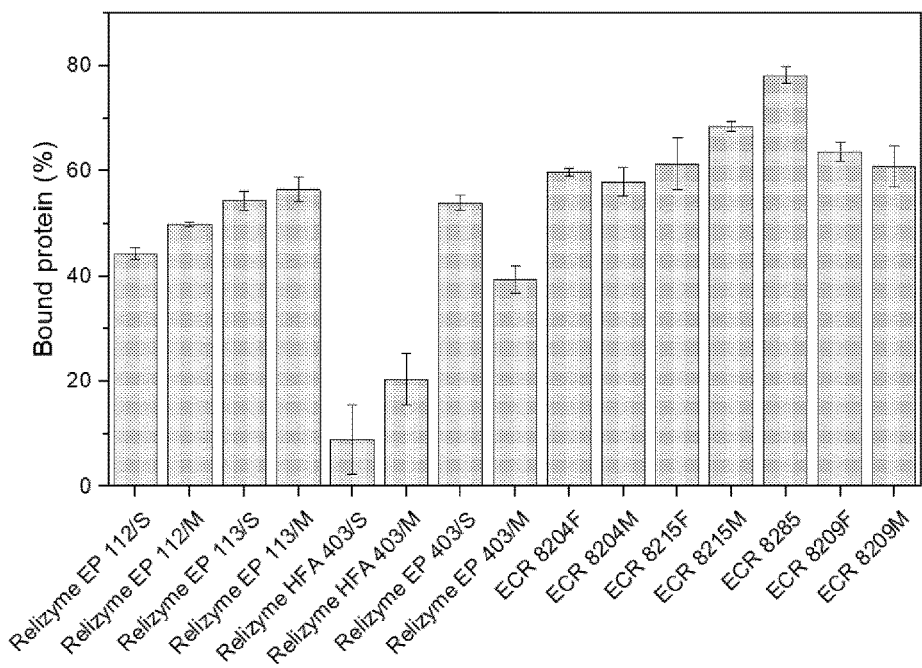
FIG. 36 shows relative total amount of protein bound to each bead. The experiments were carried out in triplicate; errors bar represent standard deviation.

On average, 200 mg of beads (Table 21) were transferred to a new 2 mL Eppendorf tube, followed by addition of 0.6 mL cell lysate solution containing enzymes for synthesis of UDP-GlcNAc. The ratio of beads (mass) over total protein was approximately 20. After 24 h of incubation at room temperature with interval rotational mixing (~every 6 h), the enzyme containing solution was removed. Afterwards, beads were washed three times with washing buffer containing high concentration of salt (200 mM Tris-HCl (pH 8.5) and 600 mM NaCl) to remove weakly bound proteins. Afterwards, beads were incubated for 24 h in storage buffer (200 mM Tris-HCl (pH 8.5) and 300 mM NaCl) to block the uncoupled binding sites. The percentage of bound protein is illustrated in FIG. 36.

Figure 37:
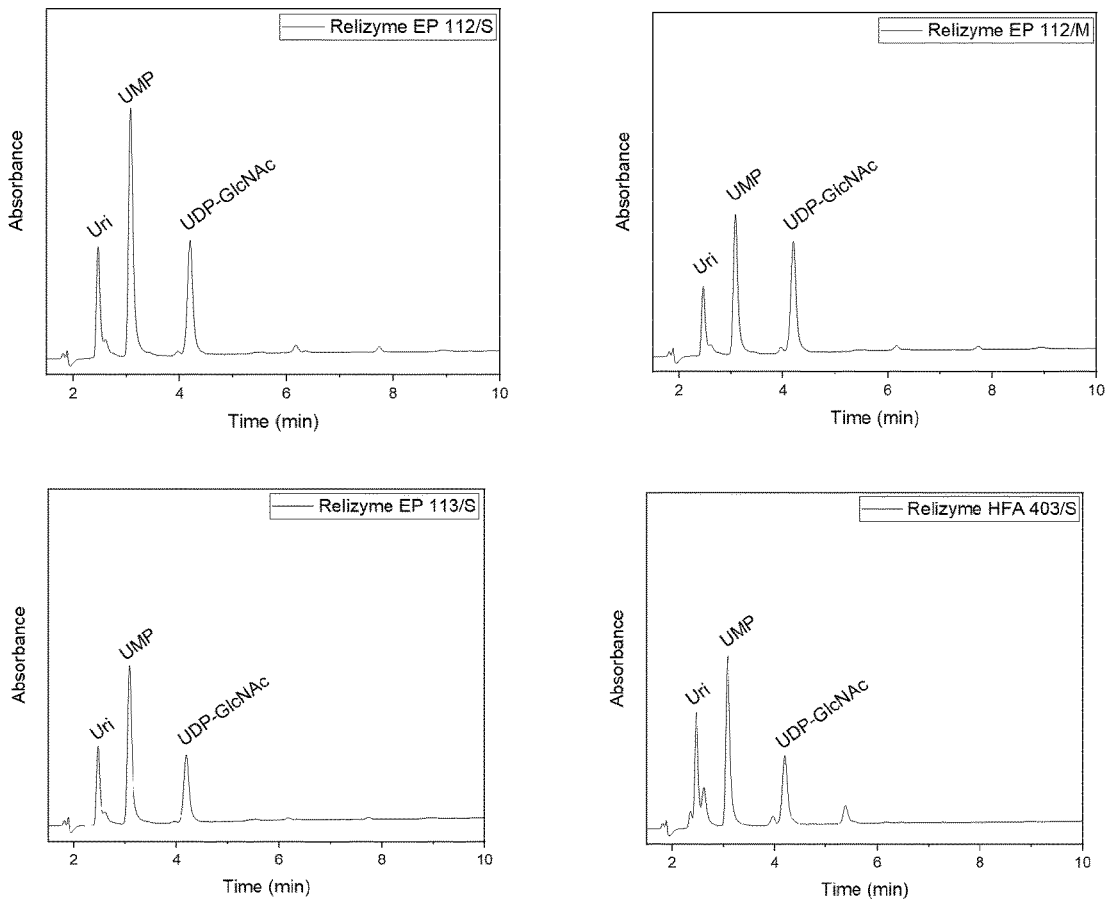
FIG. 37 shows chromatograms of reaction products for the inventive UDP-GlcNAc synthesis on each tested solid support bead.
Figure 37:
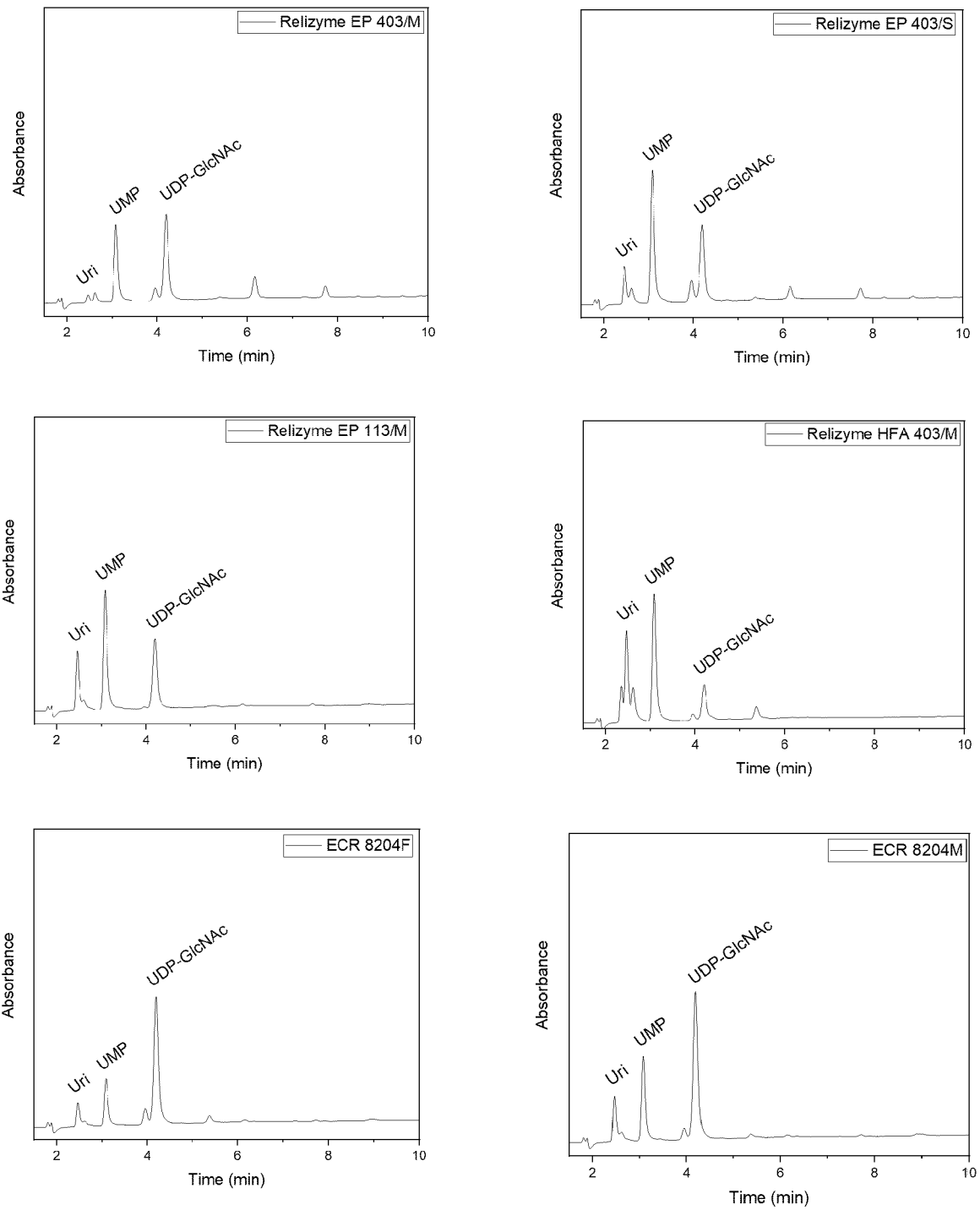
Figure 37:
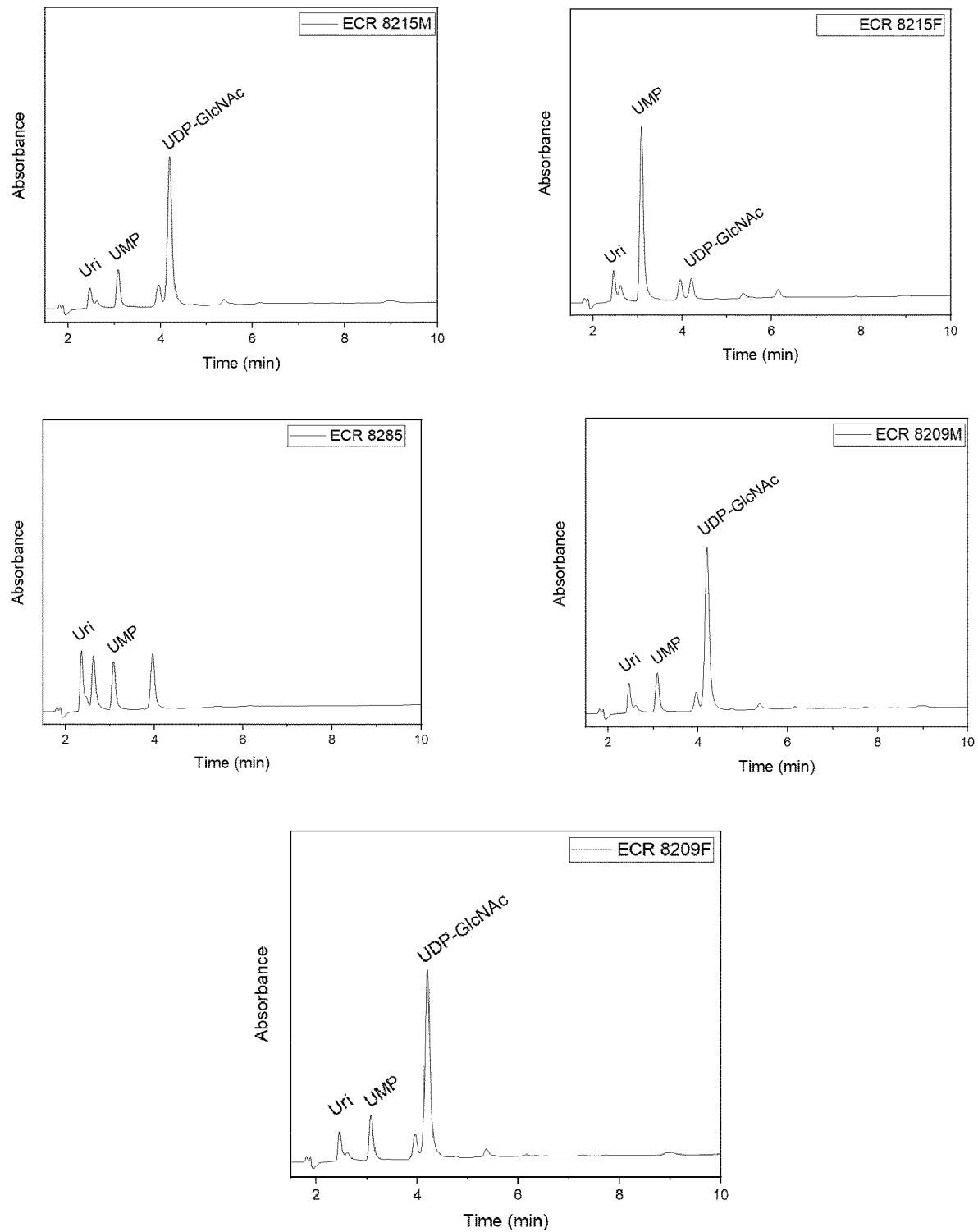
Figure 38:
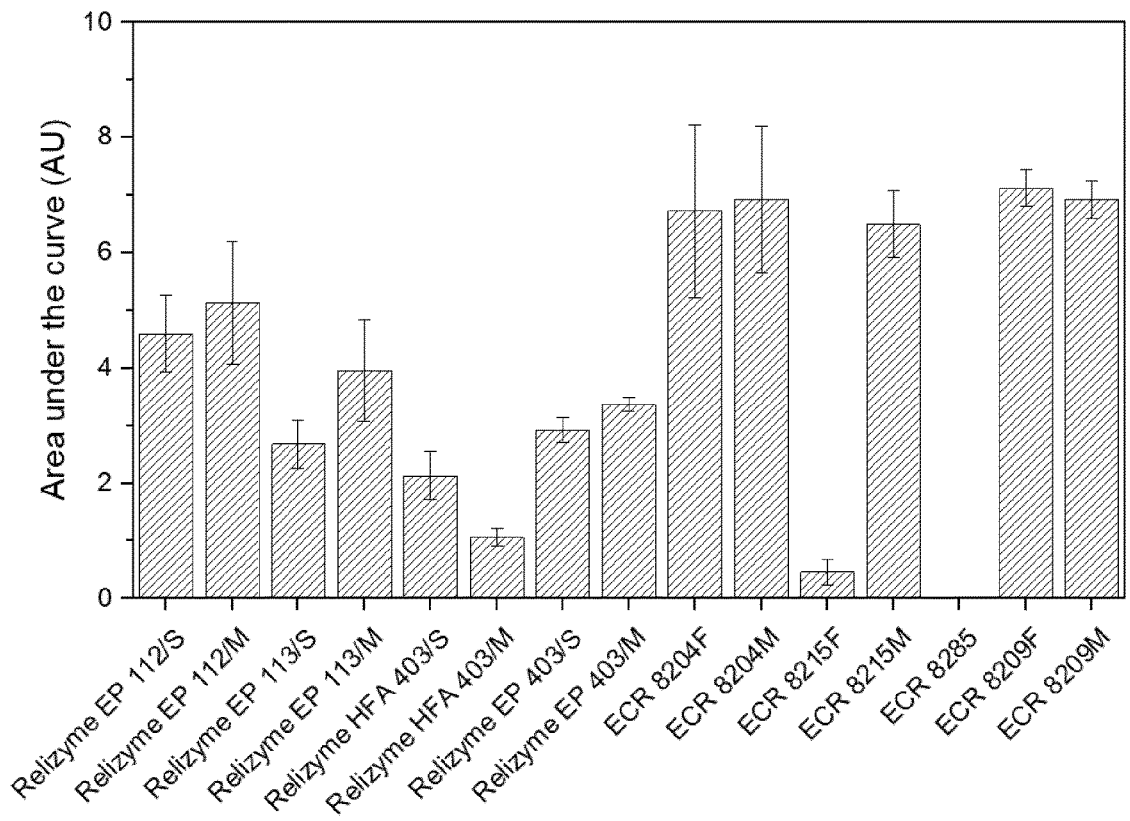
FIG. 38 shows the results of the activity test on different beads. The experiments were carried out in triplicate, except for Relizyme HFA 403/S and Relizyme HFA 403/M, of which average of three consecutive cycles are shown; errors bar represent standard deviation.

The feed solution for evaluating the activity of immobilized enzymes contained: 200 mM Tris-HCl (pH 8.5), 75 mM MgCl$_2$, 25 mM uridine, 25 mM GlcNAc, 5 mM ATP, 10 mM PolyP$_n$. 250 µL of feed solution added to beads and incubated at 37° C. and 600 rpm for 24 h. To confirm that all six enzymes bind in their active form to the solid support, the reaction with each solid support bead was monitored. The chromatogram of the reaction with each bead is shown in FIG. 37. The results of the activity test of each bead are summarized in FIG. 38. Therefore, the following beads were selected as good performing beads: Relizyme EP 113/M, ECR 8204F, ECR 8204M, ECR 8215M, ECR 8209F and ECR 8209M.

Figure 39:
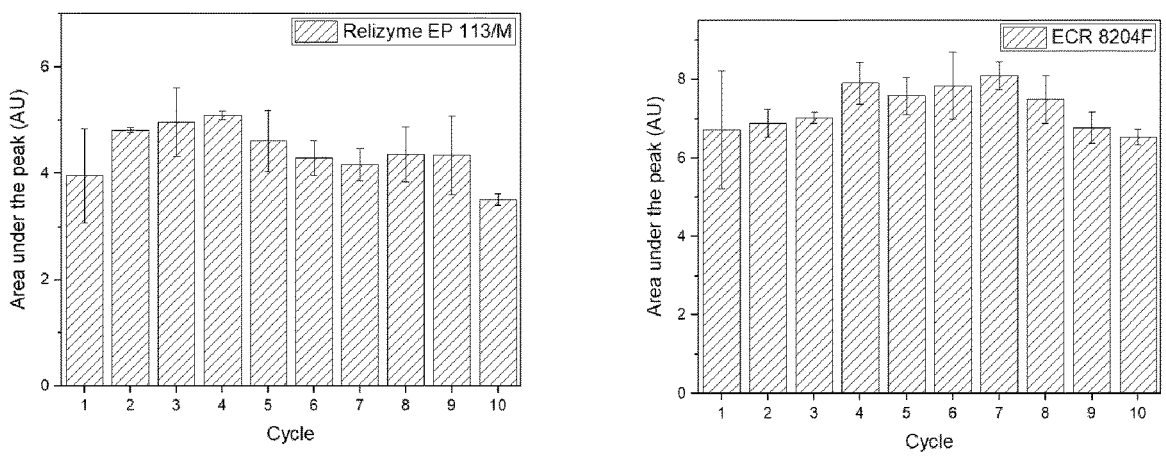
FIG. 39 shows the results of the activity test on each selected bead over 10 consecutive reaction cycle.
Figure 39:
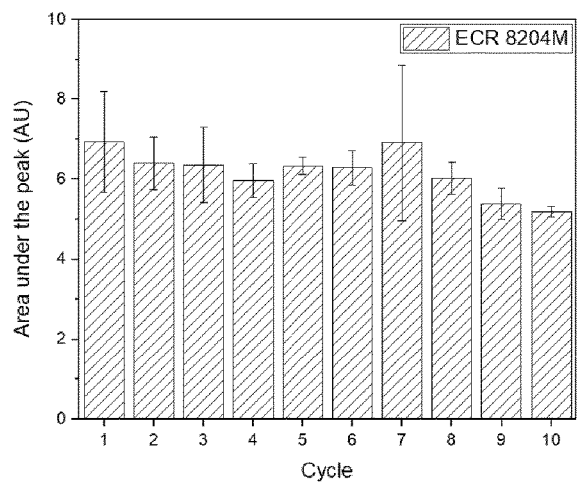
Figure 39:
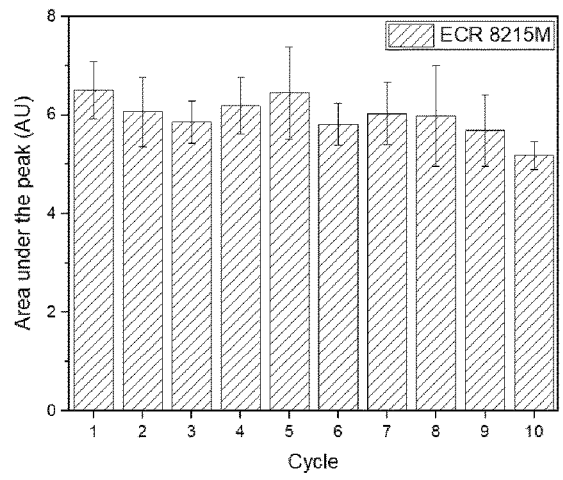
Figure 39:
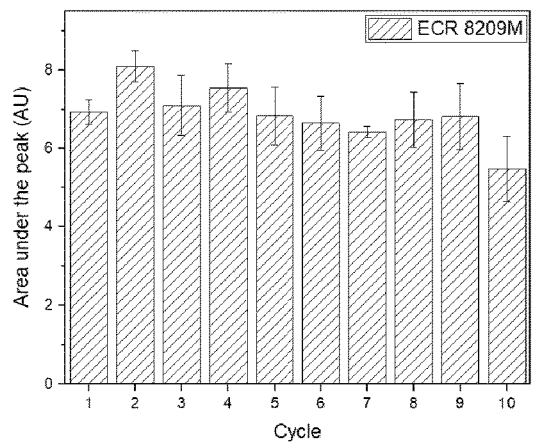
Figure 39:
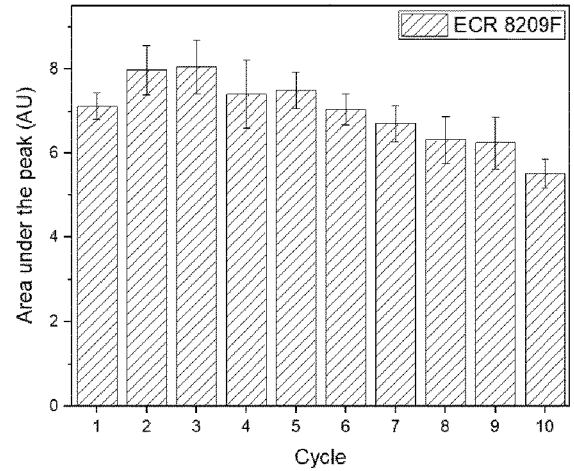

To evaluate one of the most important factors in using immobilized enzymes—stability in various cycles—the activity of aforementioned beads were evaluated in different cycles. In each cycle, 250 µL of feed solution (200 mM Tris-HCl (pH 8.5), 75 mM MgCl$_2$, 25 mM uridine, 25 mM GlcNAc, 5 mM ATP, 10 mM PolyP$_n$) were added to each vial containing beads and incubated at 600 rpm and 37° C. for 24 h. Afterwards, liquids were removed and beads were washed with water twice to avoid any carry over from previous cycles. The activity of each bead in 10 cycles is shown in FIG. 39. The tested beads Relizyme EP 113/M, ECR 8204F, ECR 8204M, ECR 8215M, ECR 8209F and ECR 8209M have been proven to be active for 10 consecutive cycles without losing activity significantly. On average, in each cycle, UDP-GlcNAc is accumulated in the supernatant with a concentration of ~7 g/L.

TABLE 21

Solid support beads used in this experiment for co-immobilization of enzymes

| Bead | Matrix | Pore size (nm) | Size (µm) | Oxiran content (µmol/gwet) |
|---|---|---|---|---|
| Relizyme EP 112/S | epoxy/polymethacrylate | 40-60 | 100-300 | 115 |
| Relizyme EP 112/M | epoxy/polymethacrylate | 40-60 | 200-500 | 112 |
| Relizyme EP 113/S | epoxy/polymethacrylate | 40-60 | 100-300 | 87 |
| Relizyme EP 113/M | epoxy/polymethacrylate | 40-60 | 200-500 | 94 |
| Relizyme HFA 403/S | epoxy/polymethacrylate | 40-60 | 100-300 | 43 |
| Relizyme HFA 403/M | epoxy/polymethacrylate | 40-60 | 200-500 | 47 |
| Relizyme EP 403/S | epoxy/polymethacrylate | 40-60 | 100-300 | 60 |
| Relizyme EP 403/M | epoxy/polymethacrylate | 40-60 | 200-500 | 56 |
| ECR 8204F | epoxy/methacrylate | 30-60 | 150-300 | |
| ECR 8204M | epoxy/methacrylate | 30-60 | 300-710 | |
| ECR 8215F | epoxy/methacrylate | 120-180 | 150-300 | |
| ECR 8215M | epoxy/methacrylate | 120-180 | 300-710 | |
| ECR 8285 | epoxy/butyl methacrylate | 40-60 | 250-1000 | |
| ECR 8209F | epoxy/methacrylate | 60-120 | 150-300 | |
| ECR 8209M | epoxy/methacrylate | 60-120 | 300-710 | |

Experiment D: Coupling of UDP-GlcNAc Cascade to ß-1,3-N-Acetyl-Glucosamine Transferase In this experiment, the reaction cascade for synthesis of UDP-GlcNAc from uridine and GlcNAc (as shown in FIG. 2) was coupled to a ß-1,3-N-acetylglucosamine transferase (ß1,3GlcNAcT) in order to synthesize lacto-N-triose (LNT II) in a single pot.

The experimental conditions were as follows: 200 mM Tris-HCl (pH 8.5), 30 mM lactose, 5 mM uridine, 40 mM GlcNAc, 1.1 mM ATP, 12 mM PolyP$_n$, 50 mM MgCl$_2$ and the following enzymes: UDK (0.06 µg/µL), URA6/PPK3 (0.11 µg/µL), NAHK (0.14 µg/µL), GLMU (0.21 µg/µL), PmPpa (0.04 µg/µL), B1,3GlcNAcT (0.06 µg/µL) with final volume of 250 µL. After 48 h of incubation at 30° C., LNT II was produced with a final concentration of 4.7 mM (2.5 g/L).

1. Mahour, R., et al., *Establishment of a five-enzyme cell-free cascade for the synthesis of uridine diphosphate N-acetyl-glucosamine*. Journal of Biotechnology, 2018. 283: p. 120-129.
2. Rexer, T. F. T., et al., *One pot synthesis of GDP-mannose by a multi-enzyme cascade for enzymatic assembly of lipid-linked oligosaccharides*. Biotechnology and Bioengineering, 2018. 115(1): p. 192-205.
3. Liese, A. and L. Hilterhaus, *Evaluation of immobilized enzymes for industrial applications*. Chemical Society reviews, 2013. 42(15): p. 6236-6249.

---

The invention claimed is:

1. A method for producing uridine 5'-diphospho-N-acetyl-α-D-glucosamine comprising:

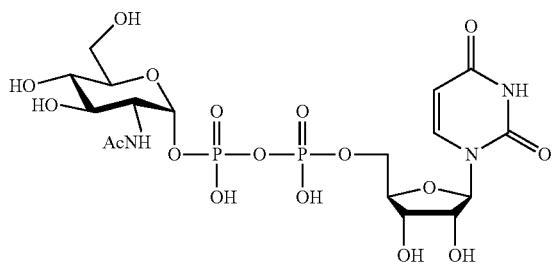

providing a solution comprising
(i) uridine monophosphate and N-acetyl-D-glucosamine represented by the following formulae

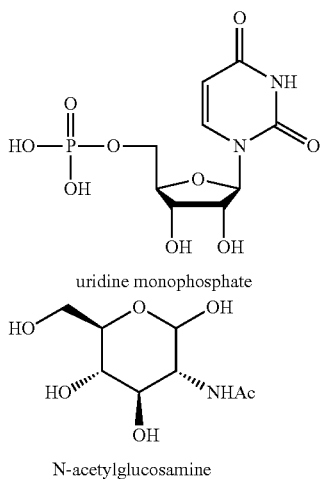

uridine monophosphate

N-acetylglucosamine (ii) polyphosphate, and adenosine triphosphate; and
providing a set of enzymes comprising a glucose-1-phosphate uridylyltransferase, an N-acetylhexosamine kinase, a polyphosphate kinase, and a uridine monophosphate kinase;

A) producing uridine 5'-diphospho-N-acetyl-α-D-glucosamine from uridine monophosphate and N-acetyl-glucosamine in the presence of the set of enzymes, polyphosphate, and adenosine triphosphate, wherein the set of enzymes is covalently or adsorptively immobilized on a reusable, mechanically stable solid support.

2. The method according to claim 1, wherein the set of enzymes is co-immobilized on the solid support.

3. The method according to claim 1, wherein the set of enzymes is covalently immobilized on a reusable, mechanically stable solid support.

4. The method according to claim 1, wherein the solid support is composed of beads or resins comprising a polymer with epoxide functional groups, with amino epoxide functional groups, with ethylenediamine functional groups, with amino C2 functional groups, with amino C6 functional groups, with anionic/amino C6 spacer functional groups.

5. The method according to claim 1, wherein the solid support is a polymer functionalized with epoxy groups.

6. The method according to claim 1, wherein the set of enzymes further comprises a pyrophosphatase.

7. The method according to claim 1, wherein the set of enzymes is directly co-immobilized on a solid support from fermentation broth, crude cell lysate, purified cell lysate or cell homogenate.

8. The method according to claim 1, wherein the set of enzymes further comprises a one-domain polyphosphate kinase 2 and/or wherein the set of enzymes further comprises a two-domain polyphosphate kinase 2.

9. The method according to claim 1, wherein the concentration of adenosine triphosphate in the solution provided in A) is in the range of 0.001 moles to 0.9 moles per mole N-acetyl-D-glucosamine.

10. The method according to claim 1, wherein the concentration of uridine monophosphate and N-acetyl-D-glucosamine in the solution provided in A) is in the range of 0.2 mM to 15,000 mM.

11. The method according to claim 1, wherein the uridine 5'-diphospho-N-acetyl-α-D-glucosamine is produced in a single reaction mixture.

12. The method according to claim 1, wherein the uridine monophosphate in A) is obtained from (i) uridine, adenosine triphosphate and a uridine kinase; or (ii) uracil, 5-phospho-α-D-ribose 1-diphosphate and an uracil phosphoribosyltransferase; or (iii) from orotic acid, 5-phospho-α-D-ribose 1-diphosphate, an orotate phosphoribosyltransferase and a UMP transferase.

13. The method according to claim 1, further comprising
producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetylglucosamine and a saccharide, glycopeptide, glycoprotein, protein, peptide, bioconjugate or small molecule by forming an O-glycosidic bond between uridine 5'-diphosphoN-acetylglucosamine and an available hydroxyl group of the saccharide, glycopeptide, glycoprotein, protein, peptide, bioconjugate or small molecule in the presence of an N-acetylglucosaminyltransferase.

14. The method according to claim 13, wherein the saccharide, glycopeptide, glycoprotein, protein, peptide, bioconjugate or small molecule is an antibody or a monoclonal antibody; or a human milk oligosaccharide or a bioconjugate.

15. The method according to claim 13, further comprising recycling of uridine diphosphate formed from the producing a GlcNAcylated saccharide, a GlcNAcylated glycopeptide, a GlcNAcylated glycoprotein, a GlcNAcylated protein, a GlcNAcylated peptide, a GlcNAcylated bioconjugate or a GlcNAcylated small molecule from uridine 5'-diphospho-N-acetylglucosamine and a saccharide, glycopeptide, glycoprotein, protein, peptide, bioconjugate or small molecule by forming an O-glycosidic bond between uridine 5'-diphospho-N-acetylglucosamine and an available hydroxyl group of the saccharide, glycopeptide, glycoprotein, protein, peptide, bioconjugate or small molecule in the presence of an N-acetylglucosaminyltransferase to obtain uridine triphosphate.

16. The method according to claim 13, wherein the saccharide, glycopeptide, glycoprotein, protein, peptide, bioconjugate or small molecule is a carbohydrate conjugate vaccine or an antibody drug conjugate.

* * * * *

SEQUENCE LISTING

<160> NUMBER OF SEQ ID NOS: 10

<210> SEQ ID NO 1
<211> LENGTH: 359
<212> TYPE: PRT
<213> ORGANISM: Bifido-bacterium longum
<220> FEATURE:
<221> NAME/KEY: PEPTIDE
<222> LOCATION: (1)..(359)
<223> OTHER INFORMATION: N-acetylhexosamine 1-kinase

<400> SEQUENCE: 1

```
Met Thr Glu Ser Asn Glu Asp Leu Phe Gly Ile Ala Ser His Phe Ala
1               5                   10                  15

Leu Glu Gly Ala Val Thr Gly Ile Glu Pro Tyr Gly Asp Gly His Ile
            20                  25                  30

Asn Thr Thr Tyr Leu Val Thr Thr Asp Gly Pro Arg Tyr Ile Leu Gln
        35                  40                  45

Gln Met Asn Thr Ser Ile Phe Pro Asp Thr Val Asn Leu Met Arg Asn
    50                  55                  60

Val Glu Leu Val Thr Ser Thr Leu Lys Ala Gln Gly Lys Glu Thr Leu
65                  70                  75                  80

Asp Ile Val Pro Thr Thr Ser Gly Ala Thr Trp Ala Glu Ile Asp Gly
                85                  90                  95

Gly Ala Trp Arg Val Tyr Lys Phe Ile Glu His Thr Val Ser Tyr Asn
            100                 105                 110

Leu Val Pro Asn Pro Asp Val Phe Arg Glu Ala Gly Ser Ala Phe Gly
        115                 120                 125

Asp Phe Gln Asn Phe Leu Ser Glu Phe Asp Ala Ser Gln Leu Thr Glu
    130                 135                 140

Thr Ile Ala His Phe His Asp Thr Pro His Arg Phe Glu Asp Phe Lys
145                 150                 155                 160

Ala Ala Leu Ala Ala Asp Lys Leu Gly Arg Ala Ala Ala Cys Gln Pro
                165                 170                 175

Glu Ile Asp Phe Tyr Leu Ser His Ala Asp Gln Tyr Ala Val Val Met
            180                 185                 190

Asp Gly Leu Arg Asp Gly Ser Ile Pro Leu Arg Val Thr His Asn Asp
        195                 200                 205

Thr Lys Leu Asn Asn Ile Leu Met Asp Ala Thr Thr Gly Lys Ala Arg
    210                 215                 220

Ala Ile Ile Asp Leu Asp Thr Ile Met Pro Gly Ser Met Leu Phe Asp
225                 230                 235                 240

Phe Gly Asp Ser Ile Arg Phe Gly Ala Ser Thr Ala Leu Glu Asp Glu
                245                 250                 255
```

Lys Asp Leu Ser Lys Val His Phe Ser Thr Glu Leu Phe Arg Ala Tyr
            260                 265                 270

Thr Glu Gly Phe Val Gly Glu Leu Arg Gly Ser Ile Thr Ala Arg Glu
        275                 280                 285

Ala Glu Leu Leu Pro Phe Ser Gly Asn Leu Leu Thr Met Glu Cys Gly
    290                 295                 300

Met Arg Phe Leu Ala Asp Tyr Leu Gly Asp Ile Tyr Phe Ala Thr
305                 310                 315                 320

Lys Tyr Pro Glu His Asn Leu Val Arg Thr Arg Thr Gln Ile Lys Leu
                325                 330                 335

Val Gln Glu Met Glu Gln Lys Ala Ser Glu Thr Arg Ala Ile Val Ala
            340                 345                 350

Asp Ile Met Glu Ala Ala Arg
            355

<210> SEQ ID NO 2
<211> LENGTH: 202
<212> TYPE: PRT
<213> ORGANISM: Arabidopsis thaliana
<220> FEATURE:
<221> NAME/KEY: PEPTIDE
<222> LOCATION: (1)..(202)
<223> OTHER INFORMATION: uridine monophosphate kinase

<400> SEQUENCE: 2

Met Gly Ser Val Asp Ala Ala Asn Gly Ser Gly Lys Lys Pro Thr Val
1               5                   10                  15

Ile Phe Val Leu Gly Gly Pro Gly Ser Gly Lys Gly Thr Gln Cys Ala
            20                  25                  30

Tyr Ile Val Glu His Tyr Gly Tyr Thr His Leu Ser Ala Gly Asp Leu
        35                  40                  45

Leu Arg Ala Glu Ile Lys Ser Gly Ser Glu Asn Gly Thr Met Ile Gln
    50                  55                  60

Asn Met Ile Lys Glu Gly Lys Ile Val Pro Ser Glu Val Thr Ile Lys
65                  70                  75                  80

Leu Leu Gln Lys Ala Ile Gln Glu Asn Gly Asn Asp Lys Phe Leu Ile
                85                  90                  95

Asp Gly Phe Pro Arg Asn Glu Glu Asn Arg Ala Ala Phe Glu Lys Val
            100                 105                 110

Thr Glu Ile Glu Pro Lys Phe Val Leu Phe Phe Asp Cys Pro Glu Glu
        115                 120                 125

Glu Met Glu Lys Arg Leu Leu Gly Arg Asn Gln Gly Arg Glu Asp Asp
    130                 135                 140

Asn Ile Glu Thr Ile Arg Lys Arg Phe Lys Val Phe Leu Glu Ser Ser
145                 150                 155                 160

Leu Pro Val Ile His Tyr Tyr Glu Ala Lys Gly Lys Val Arg Lys Ile
                165                 170                 175

Asn Ala Ala Lys Pro Ile Glu Ala Val Phe Glu Glu Val Lys Ala Ile
            180                 185                 190

Phe Ser Pro Glu Ala Glu Lys Val Glu Ala
        195                 200

<210> SEQ ID NO 3
<211> LENGTH: 301
<212> TYPE: PRT
<213> ORGANISM: Ruegeria pomeroyi
<220> FEATURE:

```
<221> NAME/KEY: PEPTIDE
<222> LOCATION: (1)..(301)
<223> OTHER INFORMATION: polyphosphate kinase 3

<400> SEQUENCE: 3
```

Met Asn Arg Asn Gly Ser Thr Lys Asp Pro Arg Arg Met Thr Gly Ala
1               5                   10                  15

Ala Thr Gly Glu Ile Ser Arg Tyr Phe Asn Asp Lys Ala Pro Lys Asp
            20                  25                  30

Ile Arg Arg Ala Ile Glu Lys Ala Asp Lys Asp Ile Leu Ser Thr
        35                  40                  45

Thr Tyr Pro Tyr Asp Ala Glu Met Thr Ala Lys Asp Tyr Arg Ala Gln
    50                  55                  60

Met Glu Ala Leu Gln Ile Glu Leu Val Lys Leu Gln Ala Trp Ile Lys
65              70                  75                  80

Gln Ser Gly Ala Arg Val Ala Leu Leu Phe Glu Gly Arg Asp Ala Ala
                85                  90                  95

Gly Lys Gly Gly Thr Ile Lys Arg Phe Arg Glu Asn Leu Asn Pro Arg
            100                 105                 110

Gly Ala Arg Val Val Ala Leu Ser Lys Pro Thr Glu Ala Glu Arg Ser
        115                 120                 125

Gln Trp Tyr Phe Gln Arg Tyr Ile Gln His Leu Pro Ser Ala Gly Glu
    130                 135                 140

Leu Val Phe Tyr Asp Arg Ser Trp Tyr Asn Arg Gly Val Val Glu His
145                 150                 155                 160

Val Phe Gly Trp Cys Asp Glu Glu Gln Arg Glu Arg Phe Phe Arg Gln
                165                 170                 175

Val Met Pro Phe Glu His Asp Leu Val Asp Asp Gly Ile His Leu Phe
            180                 185                 190

Lys Phe Trp Leu Asn Val Gly Arg Ala Glu Gln Leu Arg Arg Phe His
        195                 200                 205

Asp Arg Glu Arg Asp Pro Leu Lys Gln Trp Lys Leu Ser Pro Val Asp
    210                 215                 220

Ile Ala Gly Leu Asp Lys Trp Glu Ala Tyr Thr Thr Ala Ile Ser Gln
225                 230                 235                 240

Thr Leu Thr Arg Ser His Ser Asp Arg Ala Pro Trp Thr Val Ile Arg
                245                 250                 255

Ser Asp Asp Lys Lys Arg Ala Arg Leu Ala Ala Ile Arg Thr Val Leu
            260                 265                 270

Ser Gly Ile Asp Tyr Asp Asn Lys Asp Arg Ala Ala Val Gly Gln Pro
        275                 280                 285

Asp Ala Ala Ile Cys Gly Gly Pro Asp Ile Trp Asp Ala
    290                 295                 300

```
<210> SEQ ID NO 4
<211> LENGTH: 302
<212> TYPE: PRT
<213> ORGANISM: E. coli K-12 MG1655
<220> FEATURE:
<221> NAME/KEY: PEPTIDE
<222> LOCATION: (1)..(302)
<223> OTHER INFORMATION: glucose 1-phosphate uridylyltransferase

<400> SEQUENCE: 4
```

Met Ala Ala Ile Asn Thr Lys Val Lys Lys Ala Val Ile Pro Val Ala
1               5                   10                  15

Gly Leu Gly Thr Arg Met Leu Pro Ala Thr Lys Ala Ile Pro Lys Glu

-continued

```
                20                  25                  30
Met Leu Pro Leu Val Asp Lys Pro Leu Ile Gln Tyr Val Val Asn Glu
            35                  40                  45

Cys Ile Ala Ala Gly Ile Thr Glu Ile Val Leu Val Thr His Ser Ser
 50                  55                  60

Lys Asn Ser Ile Glu Asn His Phe Asp Thr Ser Phe Glu Leu Glu Ala
 65                  70                  75                  80

Met Leu Glu Lys Arg Val Lys Arg Gln Leu Leu Asp Glu Val Gln Ser
                 85                  90                  95

Ile Cys Pro Pro His Val Thr Ile Met Gln Val Arg Gln Gly Leu Ala
            100                 105                 110

Lys Gly Leu Gly His Ala Val Leu Cys Ala His Pro Val Val Gly Asp
        115                 120                 125

Glu Pro Val Ala Val Ile Leu Pro Asp Val Ile Leu Asp Glu Tyr Glu
    130                 135                 140

Ser Asp Leu Ser Gln Asp Asn Leu Ala Glu Met Ile Arg Arg Phe Asp
145                 150                 155                 160

Glu Thr Gly His Ser Gln Ile Met Val Glu Pro Val Ala Asp Val Thr
                165                 170                 175

Ala Tyr Gly Val Val Asp Cys Lys Gly Val Glu Leu Ala Pro Gly Glu
            180                 185                 190

Ser Val Pro Met Val Gly Val Val Glu Lys Pro Lys Ala Asp Val Ala
        195                 200                 205

Pro Ser Asn Leu Ala Ile Val Gly Arg Tyr Val Leu Ser Ala Asp Ile
    210                 215                 220

Trp Pro Leu Leu Ala Lys Thr Pro Pro Gly Ala Gly Asp Glu Ile Gln
225                 230                 235                 240

Leu Thr Asp Ala Ile Asp Met Leu Ile Glu Lys Glu Thr Val Glu Ala
                245                 250                 255

Tyr His Met Lys Gly Lys Ser His Asp Cys Gly Asn Lys Leu Gly Tyr
            260                 265                 270

Met Gln Ala Phe Val Glu Tyr Gly Ile Arg His Asn Thr Leu Gly Thr
        275                 280                 285

Glu Phe Lys Ala Trp Leu Glu Glu Met Gly Ile Lys Lys
    290                 295                 300
```

<210> SEQ ID NO 5
<211> LENGTH: 175
<212> TYPE: PRT
<213> ORGANISM: Pasteurella multocida subsp. multocida str. Pm70
<220> FEATURE:
<221> NAME/KEY: PEPTIDE
<222> LOCATION: (1)..(175)
<223> OTHER INFORMATION: inorganic diphosphatase

<400> SEQUENCE: 5

```
Met Gly Leu Glu Thr Val Pro Ala Gly Lys Ala Leu Pro Asp Asp Ile
 1               5                  10                  15

Tyr Val Val Ile Glu Ile Pro Ala Asn Ser Asp Pro Ile Lys Tyr Glu
                20                  25                  30

Val Asp Lys Glu Ser Gly Ala Leu Phe Val Asp Arg Phe Met Ala Thr
            35                  40                  45

Ala Met Phe Tyr Pro Ala Asn Tyr Gly Tyr Val Asn Asn Thr Leu Ser
        50                  55                  60

Leu Asp Gly Asp Pro Val Asp Val Leu Val Pro Thr Pro Tyr Pro Leu
 65                  70                  75                  80
```

```
Gln Pro Gly Ser Val Ile Arg Cys Arg Pro Val Gly Val Leu Lys Met
                85                  90                  95

Thr Asp Glu Ala Gly Ser Asp Ala Lys Val Val Ala Val Pro His Ser
            100                 105                 110

Lys Leu Thr Lys Glu Tyr Asp His Ile Lys Asp Val Asn Asp Leu Pro
        115                 120                 125

Ala Leu Leu Lys Ala Gln Ile Gln His Phe Phe Glu Ser Tyr Lys Ala
    130                 135                 140

Leu Glu Ala Gly Lys Trp Val Lys Val Asp Gly Trp Glu Gly Val Asp
145                 150                 155                 160

Ala Ala Arg Gln Glu Ile Leu Asp Ser Phe Glu Arg Ala Lys Lys
                165                 170                 175

<210> SEQ ID NO 6
<211> LENGTH: 304
<212> TYPE: PRT
<213> ORGANISM: Pseudomonas aeruginosa
<220> FEATURE:
<221> NAME/KEY: PEPTIDE
<222> LOCATION: (1)..(304)
<223> OTHER INFORMATION: 1-domain polyphosphate kinase 2

<400> SEQUENCE: 6

Met Asp Ser Tyr Gly Asp Thr Ser Gly Arg Ile Gly Arg Asp Trp Leu
1               5                   10                  15

Asp Arg His Asp Glu Glu Leu Glu Gln Glu Leu Leu Asp Asp Glu Leu
            20                  25                  30

Asn Leu Asp Glu Leu Phe Gly Pro Glu Gln Glu Asp Ala Pro Gly Glu
        35                  40                  45

Leu Ser Arg Arg Arg Tyr Phe Arg Glu Leu Phe Arg Leu Gln Arg Glu
    50                  55                  60

Leu Val Lys Leu Gln Asn Trp Val Val His Thr Gly His Lys Val Val
65                  70                  75                  80

Ile Leu Phe Glu Gly Arg Asp Ala Ala Gly Lys Gly Gly Val Ile Lys
                85                  90                  95

Arg Ile Thr Gln Arg Leu Asn Pro Arg Val Cys Arg Val Ala Ala Leu
            100                 105                 110

Pro Ala Pro Asn Asp Arg Glu Gln Thr Gln Trp Tyr Phe Gln Arg Tyr
        115                 120                 125

Val Ser His Leu Pro Ala Gly Gly Glu Ile Val Leu Phe Asp Arg Ser
    130                 135                 140

Trp Tyr Asn Arg Ala Gly Val Glu Arg Val Met Gly Phe Cys Asn Asp
145                 150                 155                 160

Glu Gln Tyr Glu Glu Phe Phe Arg Ser Val Pro Glu Phe Glu Lys Met
                165                 170                 175

Leu Ala Arg Ser Gly Ile Gln Leu Leu Lys Tyr Trp Phe Ser Ile Ser
            180                 185                 190

Asp Ala Glu Gln His Leu Arg Phe Leu Ser Arg Ile His Asp Pro Leu
        195                 200                 205

Lys Gln Trp Lys Leu Ser Pro Met Asp Leu Glu Ser Arg Arg Arg Trp
    210                 215                 220

Glu Ala Tyr Thr Lys Ala Lys Glu Thr Met Leu Glu Arg Thr His Ile
225                 230                 235                 240

Pro Glu Ala Pro Trp Trp Val Val Gln Ala Asp Asp Lys Lys Arg Ala
                245                 250                 255
```

```
Arg Leu Asn Cys Ile His His Leu Leu Gln Gln Met Pro Tyr Arg Glu
            260                 265                 270

Val Pro Gln Pro Pro Val His Leu Pro Glu Arg Leu Arg His Ala Asp
        275                 280                 285

Tyr Val Arg His Pro Thr Pro Gly Glu Ile Ile Val Pro Glu Val Tyr
    290                 295                 300

<210> SEQ ID NO 7
<211> LENGTH: 496
<212> TYPE: PRT
<213> ORGANISM: Pseudomonas aeruginosa
<220> FEATURE:
<221> NAME/KEY: PEPTIDE
<222> LOCATION: (1)..(496)
<223> OTHER INFORMATION: 2-domain polyphosphate kinase 2

<400> SEQUENCE: 7

Met Phe Glu Ser Ala Glu Val Gly His Ser Ile Asp Lys Asp Thr Tyr
1               5                   10                  15

Glu Lys Ala Val Ile Glu Leu Arg Glu Ala Leu Leu Glu Ala Gln Phe
            20                  25                  30

Glu Leu Lys Gln Gln Ala Arg Phe Pro Val Ile Ile Leu Ile Asn Gly
        35                  40                  45

Ile Glu Gly Ala Gly Lys Gly Glu Thr Val Lys Leu Leu Asn Glu Trp
    50                  55                  60

Met Asp Pro Arg Leu Ile Glu Val Gln Ser Phe Leu Arg Pro Ser Asp
65                  70                  75                  80

Glu Glu Leu Glu Arg Pro Gln Trp Arg Phe Trp Arg Arg Leu Pro
                85                  90                  95

Pro Lys Gly Arg Thr Gly Ile Phe Phe Gly Asn Trp Tyr Ser Gln Met
            100                 105                 110

Leu Tyr Ala Arg Val Glu Gly His Ile Lys Glu Ala Lys Leu Asp Gln
        115                 120                 125

Ala Ile Asp Ala Ala Glu Arg Phe Glu Arg Met Leu Cys Asp Glu Gly
    130                 135                 140

Ala Leu Leu Phe Lys Phe Trp Phe His Leu Ser Lys Lys Gln Leu Lys
145                 150                 155                 160

Glu Arg Leu Lys Ala Leu Glu Lys Asp Pro Gln His Ser Trp Lys Leu
                165                 170                 175

Ser Pro Leu Asp Trp Lys Gln Ser Glu Val Tyr Asp Arg Phe Val His
            180                 185                 190

Tyr Gly Glu Arg Val Leu Arg Arg Thr Ser Arg Asp Tyr Ala Pro Trp
        195                 200                 205

Tyr Val Val Glu Gly Ala Asp Glu Arg Tyr Arg Ala Leu Thr Val Gly
    210                 215                 220

Arg Ile Leu Leu Glu Gly Leu Gln Ala Ala Leu Ala Thr Lys Glu Arg
225                 230                 235                 240

Ala Lys Arg Gln Pro His Ala Ala Pro Leu Val Ser Ser Leu Asp Asn
                245                 250                 255

Arg Gly Leu Leu Asp Ser Leu Asp Leu Gly Gln Tyr Leu Asp Lys Asp
            260                 265                 270

Ala Tyr Lys Glu Gln Leu Ala Ala Glu Gln Ala Arg Leu Ala Gly Leu
        275                 280                 285

Ile Arg Asp Lys Arg Phe Arg Gln His Ser Leu Val Ala Val Phe Glu
    290                 295                 300

Gly Asn Asp Ala Ala Gly Lys Gly Gly Ala Ile Arg Arg Val Thr Asp
```

```
                  305                 310                 315                 320
Ala Leu Asp Pro Arg Gln Tyr His Ile Val Pro Ile Ala Ala Pro Thr
                325                 330                 335

Glu Glu Glu Arg Ala Gln Pro Tyr Leu Trp Arg Phe Trp Arg His Ile
                340                 345                 350

Pro Ala Arg Arg Gln Phe Thr Ile Phe Asp Arg Ser Trp Tyr Gly Arg
                355                 360                 365

Val Leu Val Glu Arg Ile Glu Gly Phe Cys Ala Pro Ala Asp Trp Leu
    370                 375                 380

Arg Ala Tyr Gly Glu Ile Asn Asp Phe Glu Glu Gln Leu Ser Glu Tyr
385                 390                 395                 400

Gly Ile Ile Val Val Lys Phe Trp Leu Ala Ile Asp Lys Gln Thr Gln
                405                 410                 415

Met Glu Arg Phe Lys Glu Arg Glu Lys Thr Pro Tyr Lys Arg Tyr Lys
                420                 425                 430

Ile Thr Glu Glu Asp Trp Arg Asn Arg Asp Lys Trp Asp Gln Tyr Val
                435                 440                 445

Asp Ala Val Gly Asp Met Val Asp Arg Thr Ser Thr Glu Ile Ala Pro
            450                 455                 460

Trp Thr Leu Val Glu Ala Asn Asp Lys Arg Phe Ala Arg Val Lys Val
465                 470                 475                 480

Leu Arg Thr Ile Asn Asp Ala Ile Glu Ala Ala Tyr Lys Lys Asp Lys
                485                 490                 495

<210> SEQ ID NO 8
<211> LENGTH: 458
<212> TYPE: PRT
<213> ORGANISM: Pasteurella multocida
<220> FEATURE:
<221> NAME/KEY: PEPTIDE
<222> LOCATION: (1)..(458)
<223> OTHER INFORMATION: UTP-GlcNAc-1-phosphate uridylyltransferase

<400> SEQUENCE: 8

Met Lys Glu Lys Ala Leu Ser Ile Val Ile Leu Ala Ala Gly Lys Gly
1               5                   10                  15

Thr Arg Met Tyr Ser Asp Leu Pro Lys Val Leu His Lys Ile Ala Gly
                20                  25                  30

Lys Pro Met Val Lys His Val Ile Asp Thr Val Lys Ser Ile His Ala
            35                  40                  45

Lys Asn Ile His Leu Val Tyr Gly His Gly Gly Glu Val Met Gln Thr
        50                  55                  60

Arg Leu Gln Asp Glu Pro Val Asn Trp Val Leu Gln Ala Glu Gln Leu
65                  70                  75                  80

Gly Thr Gly His Ala Met Gln Gln Ala Ala Pro Phe Phe Ala Asp Asp
                85                  90                  95

Glu Asn Ile Leu Met Leu Tyr Gly Asp Gly Pro Leu Ile Thr Ala Glu
                100                 105                 110

Thr Leu Gln Thr Leu Ile Ala Ala Lys Pro Glu His Gly Ile Ala Leu
            115                 120                 125

Leu Thr Val Val Leu Asp Asp Pro Thr Gly Tyr Gly Arg Ile Val Arg
        130                 135                 140

Glu Asn Gly Asn Val Val Ala Ile Val Glu Gln Lys Asp Ala Asn Ala
145                 150                 155                 160

Glu Gln Leu Lys Ile Gln Glu Ile Asn Thr Gly Leu Leu Val Ala Asp
                165                 170                 175
```

```
Gly Lys Ser Leu Lys Lys Trp Leu Ser Gln Leu Thr Asn Asn Asn Ala
            180                 185                 190

Gln Gly Glu Tyr Tyr Ile Thr Asp Val Ile Ala Leu Ala Asn Gln Asp
            195                 200                 205

Gly Cys Gln Val Val Ala Val Gln Ala Ser Asp Phe Met Glu Val Glu
210                 215                 220

Gly Val Asn Asn Arg Gln Gln Leu Ala Arg Leu Glu Arg Tyr Tyr Gln
225                 230                 235                 240

Arg Lys Gln Ala Asp Asn Leu Leu Ala Gly Val Ala Leu Ala Asp
            245                 250                 255

Pro Glu Arg Phe Asp Leu Arg Gly Glu Leu Ser His Gly Lys Asp Val
            260                 265                 270

Glu Ile Asp Val Asn Val Ile Ile Glu Gly Lys Val Ser Leu Gly His
            275                 280                 285

Arg Val Lys Ile Gly Ala Gly Cys Val Leu Lys Asn Cys Gln Ile Gly
            290                 295                 300

Asp Asp Val Glu Ile Lys Pro Tyr Ser Val Leu Glu Glu Ala Ile Val
305                 310                 315                 320

Gly Gln Ala Ala Gln Ile Gly Pro Phe Ser Arg Leu Arg Pro Gly Thr
            325                 330                 335

Ala Leu Ala Asp Asn Thr His Ile Gly Asn Phe Val Glu Ile Lys Lys
            340                 345                 350

Ala His Ile Gly Thr Gly Ser Lys Val Asn His Leu Ser Tyr Val Gly
            355                 360                 365

Asp Ala Glu Val Gly Met Gln Cys Asn Ile Gly Ala Gly Val Ile Thr
            370                 375                 380

Cys Asn Tyr Asp Gly Ala Asn Lys Phe Lys Thr Ile Ile Gly Asp Asn
385                 390                 395                 400

Val Phe Val Gly Ser Asp Val Gln Leu Val Ala Pro Val Thr Ile Glu
            405                 410                 415

Thr Gly Ala Thr Ile Gly Ala Gly Thr Thr Val Thr Lys Asp Val Ala
            420                 425                 430

Cys Asp Glu Leu Val Ile Ser Arg Val Pro Gln Arg His Ile Gln Gly
            435                 440                 445

Trp Gln Arg Pro Thr Lys Gln Thr Lys Lys
            450                 455
```

<210> SEQ ID NO 9
<211> LENGTH: 213
<212> TYPE: PRT
<213> ORGANISM: Escherichia coli
<220> FEATURE:
<221> NAME/KEY: PEPTIDE
<222> LOCATION: (1)..(213)
<223> OTHER INFORMATION: uridine/cytidine kinase

<400> SEQUENCE: 9

```
Met Thr Asp Gln Ser His Gln Cys Val Ile Ile Gly Ile Ala Gly Ala
1               5                   10                  15

Ser Ala Ser Gly Lys Ser Leu Ile Ala Ser Thr Leu Tyr Arg Glu Leu
            20                  25                  30

Arg Glu Gln Val Gly Asp Glu His Ile Gly Val Ile Pro Glu Asp Cys
        35                  40                  45

Tyr Tyr Lys Asp Gln Ser His Leu Ser Met Glu Glu Arg Val Lys Thr
    50                  55                  60
```

```
Asn Tyr Asp His Pro Ser Ala Met Asp His Ser Leu Leu Glu His
 65                  70                  75                  80

Leu Gln Ala Leu Lys Arg Gly Ser Ala Ile Asp Leu Pro Val Tyr Ser
                 85                  90                  95

Tyr Val Glu His Thr Arg Met Lys Glu Thr Val Thr Val Glu Pro Lys
            100                 105                 110

Lys Val Ile Ile Leu Glu Gly Ile Leu Leu Thr Asp Ala Arg Leu
        115                 120                 125

Arg Asp Glu Leu Asn Phe Ser Ile Phe Val Asp Thr Pro Leu Asp Ile
130                 135                 140

Cys Leu Met Arg Arg Ile Lys Arg Asp Val Asn Glu Arg Gly Arg Ser
145                 150                 155                 160

Met Asp Ser Val Met Ala Gln Tyr Gln Lys Thr Val Arg Pro Met Phe
                165                 170                 175

Leu Gln Phe Ile Glu Pro Ser Lys Gln Tyr Ala Asp Ile Ile Val Pro
            180                 185                 190

Arg Gly Gly Lys Asn Arg Ile Ala Ile Asp Ile Leu Lys Ala Lys Ile
        195                 200                 205

Ser Gln Phe Phe Glu
    210

<210> SEQ ID NO 10
<211> LENGTH: 333
<212> TYPE: PRT
<213> ORGANISM: Escherichia coli
<220> FEATURE:
<221> NAME/KEY: PEPTIDE
<222> LOCATION: (1)..(333)
<223> OTHER INFORMATION: beta-1,3-N-acetylglucosamine transferase

<400> SEQUENCE: 10

Met Gln Pro Leu Val Ser Val Leu Ile Cys Ala Tyr Asn Val Glu Lys
1               5                   10                  15

Tyr Phe Ala Gln Ser Leu Ala Ala Val Val Asn Gln Thr Trp Arg Asn
            20                  25                  30

Leu Asp Ile Leu Ile Val Asp Asp Gly Ser Thr Asp Gly Thr Leu Ala
        35                  40                  45

Ile Ala Gln Arg Phe Gln Glu Gln Asp Gly Arg Ile Arg Ile Leu Ala
    50                  55                  60

Gln Pro Arg Asn Ser Gly Leu Ile Pro Ser Leu Asn Ile Gly Leu Asp
65                  70                  75                  80

Glu Leu Ala Lys Ser Gly Gly Gly Glu Tyr Ile Ala Arg Thr Asp
            85                  90                  95

Ala Asp Asp Ile Ala Ala Pro Asp Trp Ile Glu Lys Ile Val Gly Glu
            100                 105                 110

Met Glu Lys Asp Arg Ser Ile Ile Ala Met Gly Ala Trp Leu Glu Val
        115                 120                 125

Leu Ser Glu Glu Lys Asp Gly Asn Arg Leu Ala Arg His His Glu His
130                 135                 140

Gly Lys Ile Trp Lys Lys Pro Thr Arg His Glu Asp Ile Ala Asp Phe
145                 150                 155                 160

Phe Pro Phe Gly Asn Pro Ile His Asn Asn Thr Met Ile Met Arg Arg
                165                 170                 175

Ser Val Ile Asp Gly Gly Leu Arg Tyr Asn Thr Glu Arg Asp Trp Ala
            180                 185                 190

Glu Asp Tyr Gln Phe Trp Tyr Asp Val Ser Lys Leu Gly Arg Leu Ala
```

-continued

| | | | | | 195 | | | | 200 | | | | 205 | | |
|---|---|---|---|---|---|---|---|---|---|---|---|---|---|---|---|
| Tyr | Tyr | Pro | Glu | Ala | Leu | Val | Lys | Tyr | Arg | Leu | His | Ala | Asn | Gln | Val |
| | 210 | | | | | 215 | | | | | 220 | | | | |
| Ser | Ser | Lys | Tyr | Ser | Ile | Arg | Gln | His | Glu | Ile | Ala | Gln | Gly | Ile | Gln |
| 225 | | | | | 230 | | | | | 235 | | | | | 240 |
| Lys | Thr | Ala | Arg | Asn | Asp | Phe | Leu | Gln | Ser | Met | Gly | Phe | Lys | Thr | Arg |
| | | | | 245 | | | | | 250 | | | | | 255 | |
| Phe | Asp | Ser | Leu | Glu | Tyr | Arg | Gln | Ile | Lys | Ala | Val | Ala | Tyr | Glu | Leu |
| | | | 260 | | | | | 265 | | | | | 270 | | |
| Leu | Glu | Lys | His | Leu | Pro | Glu | Glu | Asp | Phe | Glu | Leu | Ala | Arg | Arg | Phe |
| | | | 275 | | | | | 280 | | | | | 285 | | |
| Leu | Tyr | Gln | Cys | Phe | Lys | Arg | Thr | Asp | Thr | Leu | Pro | Ala | Gly | Ala | Trp |
| | | 290 | | | | 295 | | | | | 300 | | | | |
| Leu | Asp | Phe | Ala | Ala | Asp | Gly | Arg | Met | Arg | Arg | Leu | Phe | Thr | Leu | Arg |
| 305 | | | | | 310 | | | | | 315 | | | | | 320 |
| Gln | Tyr | Phe | Gly | Ile | Leu | His | Arg | Leu | Leu | Lys | Asn | Arg | | | |
| | | | | 325 | | | | | 330 | | | | | | |